(12) United States Patent
Ohmura et al.

(10) Patent No.: US 7,747,345 B2
(45) Date of Patent: Jun. 29, 2010

(54) AUTOMATIC DRUG DISPENSER AND DRUG FEEDER

(75) Inventors: Shiro Ohmura, Tokyo (JP); Yoshihito Ohmura, Tokyo (JP); Syunji Ohgaya, Kanagawa (JP); Hiroo Fujiwara, Tokyo (JP)

(73) Assignee: Tosho Inc., Tokyo (JP)

( * ) Notice: Subject to any disclaimer, the term of this patent is extended or adjusted under 35 U.S.C. 154(b) by 381 days.

(21) Appl. No.: 10/584,979

(22) PCT Filed: Dec. 22, 2004

(86) PCT No.: PCT/JP2004/019236

§ 371 (c)(1), (2), (4) Date: Oct. 17, 2006

(87) PCT Pub. No.: WO2005/065627

PCT Pub. Date: Jul. 21, 2005

(65) Prior Publication Data

US 2007/0150092 A1    Jun. 28, 2007

(30) Foreign Application Priority Data

| Jan. 5, 2004 | (JP) | ............................. 2004-000408 |
| Mar. 3, 2004 | (JP) | ............................. 2004-059186 |
| Jun. 1, 2004 | (JP) | ............................. 2004-163791 |
| Jun. 1, 2004 | (JP) | ............................. 2004-163796 |
| Sep. 2, 2004 | (JP) | ............................. 2004-255100 |

(51) Int. Cl.
G06F 17/00 (2006.01)

(52) U.S. Cl. ................. 700/231; 700/236; 700/242

(58) Field of Classification Search ......... 700/231–244; 221/1–312 C
See application file for complete search history.

(56) References Cited

U.S. PATENT DOCUMENTS 5,930,145 A * 7/1999 Yuyama et al. .............. 700/231
6,471,088 B1 * 10/2002 Uema et al. .................... 221/4

(Continued)

FOREIGN PATENT DOCUMENTS

CN      1408614      4/2003

(Continued)

OTHER PUBLICATIONS

IPR of PCT/JP2004/019236, Apr. 26, 2005, Tosho Inc. et al.

(Continued)

*Primary Examiner*—Gene Crawford
*Assistant Examiner*—Michael K Collins
(74) *Attorney, Agent, or Firm*—Matthew B. Dernier, Esq.; Gibson & Dernier LLP

(57) ABSTRACT

An automatic drug dispenser includes: a drug cassette which ejectably accommodates drugs; a base unit which detachably supports the drug cassette and drives a motor to eject drugs; a drug feeder storage which is designed to store a large number of base units; a reading device which is provided in each of the base units and reads identification information assigned to the drug cassette; and a checking means which compares a result of reading with pre-stored check data, wherein a microprocessor is mounted in each of the base units, and the checking means, the check data and history information related to the cassette are built in each microprocessor in a distributed manner.

14 Claims, 40 Drawing Sheets

U.S. PATENT DOCUMENTS

| | | | |
|---|---|---|---|
| 6,580,968 B1 * | 6/2003 | Yuyama et al. | 700/241 |
| 6,690,998 B1 * | 2/2004 | Yuyama | 700/242 |
| 2003/0074223 A1 * | 4/2003 | Hickle et al. | 705/2 |
| 2003/0074868 A1 * | 4/2003 | Yasuoka et al. | 53/493 |
| 2004/0176873 A1 * | 9/2004 | Kim | 700/231 |
| 2005/0234591 A1 * | 10/2005 | Kim | 700/231 |

FOREIGN PATENT DOCUMENTS

| | | |
|---|---|---|
| JP | H5-7601 | 2/1993 |
| JP | H5-7602 | 2/1993 |
| JP | 06-080103 | 3/1994 |
| JP | 11-206855 | 8/1999 |
| JP | 11206855 A * | 8/1999 |
| JP | 2002-153541 | 5/2002 |
| JP | 2002-154637 | 5/2002 |
| JP | 2002-272812 | 9/2002 |
| JP | 2002-370703 | 12/2002 |
| JP | 2003-237714 | 8/2003 |
| JP | 2004-238066 | 8/2004 |

OTHER PUBLICATIONS

Int'l Search Report Apr. 26, 2005.

* cited by examiner

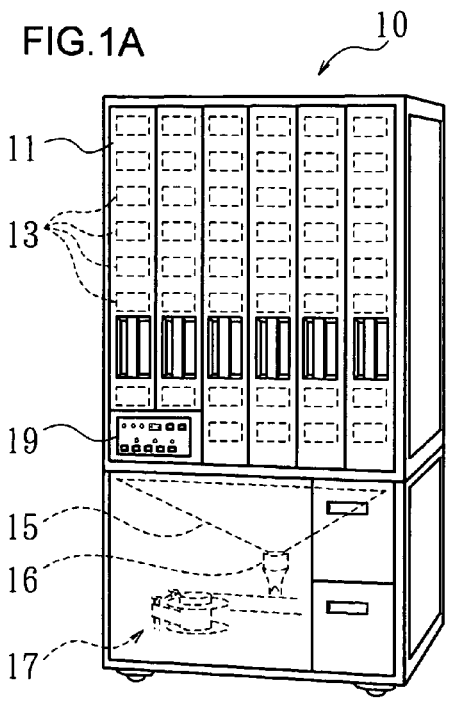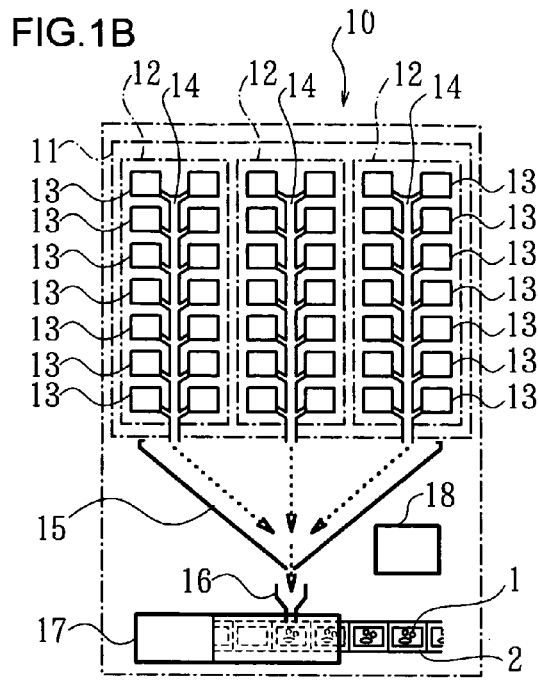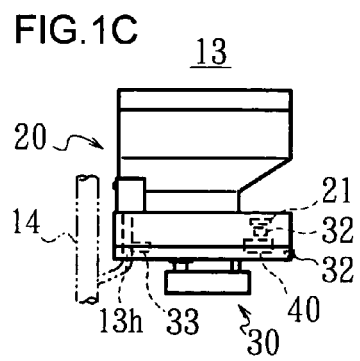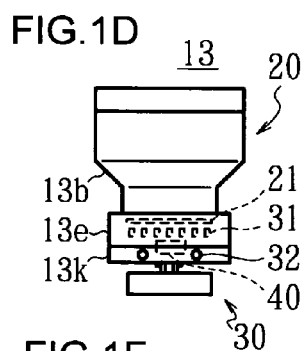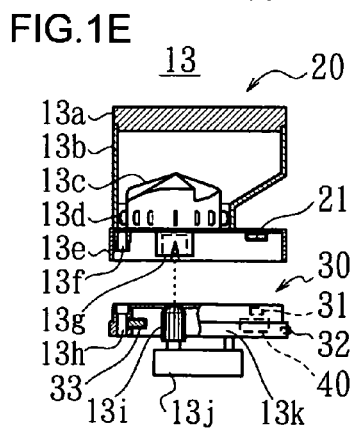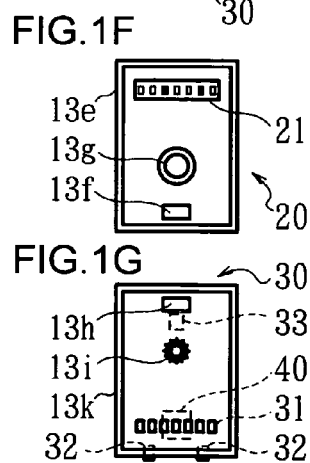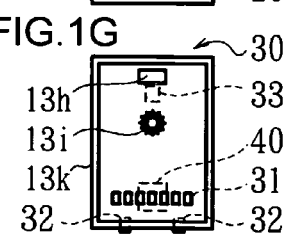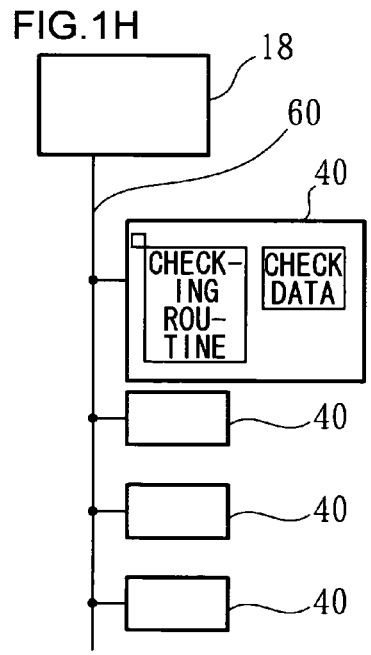

FIG.3A FIRST DECISION TABLE

| MIXING-IN | YES | | | | NO | | | |
|---|---|---|---|---|---|---|---|---|
| EXCESS | YES | | NO | | YES | | NO | |
| ATTACH-MENT/DETACH-MENT | YES | – | YES | – | YES | – | YES | – |
| RANK | B | – | B | – | B | – | C | – |

FIG.3B SECOND DECISION TABLE

| MIXING-IN | YES | | | | NO | | | |
|---|---|---|---|---|---|---|---|---|
| EXCESS | YES | | NO | | YES | | NO | |
| ATTACH-MENT/DETACH-MENT | – | NO | – | NO | – | NO | – | NO |
| RANK | – | A | – | B | – | B | – | E |

FIG.4A
DRUG DISPENSING HISTORY INFORMATION

| TIME | MIXING-IN/ EXCESS | RANK |
|---|---|---|
| 1234 | MIXING-IN | A |
| 2345 | EXCESS | AA |
| 3456 | MIXING-IN | A |
| ⋮ | ⋮ | ⋮ |

FIG.4B ATTACHMENT/DETACHMENT HISTORY INFORMATION

| TIME | CASSETTE ATTACHMENT/ DETACHMENT | RANK |
|---|---|---|
| 1221 | ATTACHMENT | E |
| 2323 | DETACHMENT | C |
| 3210 | ATTACHMENT | E |
| ⋮ | ⋮ | ⋮ |

FIG.5A
FABRICATION HISTORY INFORMATION
| TIME | PROCESS ID | PERSONNEL ID |
|------|------------|--------------|
| 0012 | 1 | 95 |
| 0333 | 2 | 42 |
| 0454 | 3 | 67 |
| ⋮ | ⋮ | ⋮ |
FIG.5B
SELECTION HISTORY INFORMATION
| TIME | DOSAGE FORM | CAPSULE | COMPAT-IBILITY |
|------|-------------|---------|----------------|
| 0111 | F | | 110 |
| 0123 | | ○ | NO |
| 0135 | R | | 125 |
| ⋮ | ⋮ | ⋮ | ⋮ |
FIG.5C
TABLET : TYPE F
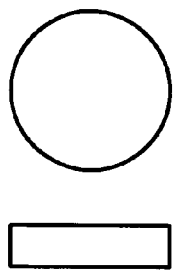
FIG.5D
TABLET : TYPE FR
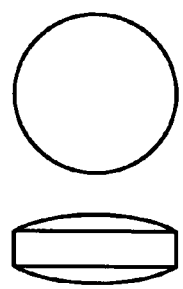
FIG.5E
TABLET : TYPE R
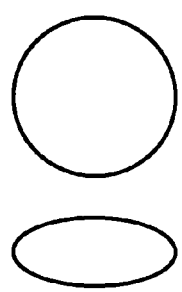

FIG.16A

DRUG MASTER TABLE

| DRUG CODE | DRUG INFORMATION | MACHINE 1 ID | CHECK DATA (CASSETTE IDENTIFICATION INFORMATION) | FEEDER STORAGE ADDRESS (COLUMN ADDRESS) (ROW ADDRESS) (BOARD ADDRESS) | CASSETTE STATE | AC FLAG |
|---|---|---|---|---|---|---|
| | | | CHECK DATA (CASSETTE IDENTIFICATION INFORMATION) | FEEDER STORAGE ADDRESS (COLUMN ADDRESS) (ROW ADDRESS) (BOARD ADDRESS) | CASSETTE STATE | AC FLAG |
| | | ⋮ | ⋮ | ⋮ | ⋮ | ⋮ |
| | | MACHINE N ID | CHECK DATA (CASSETTE IDENTIFICATION INFORMATION) | FEEDER STORAGE ADDRESS (COLUMN ADDRESS) (ROW ADDRESS) (BOARD ADDRESS) | CASSETTE STATE | AC FLAG |

FIG.16B

DRUG EJECTION INSTRUCTION (TO 413)

| MACHINE n ID | FEEDER STORAGE ADDRESS (COLUMN ADDRESS) (ROW ADDRESS) (BOARD ADDRESS) | TABLET COUNT ETC. | AC OFF |
|---|---|---|---|

FIG.16C

DRUG EJECTION INSTRUCTION (TO 530)

| MACHINE n ID | CHECK DATA (CASSETTE IDENTIFICATION INFORMATION) | TABLET COUNT ETC. | AC ON |
|---|---|---|---|

FIG.21A
FIG.21B
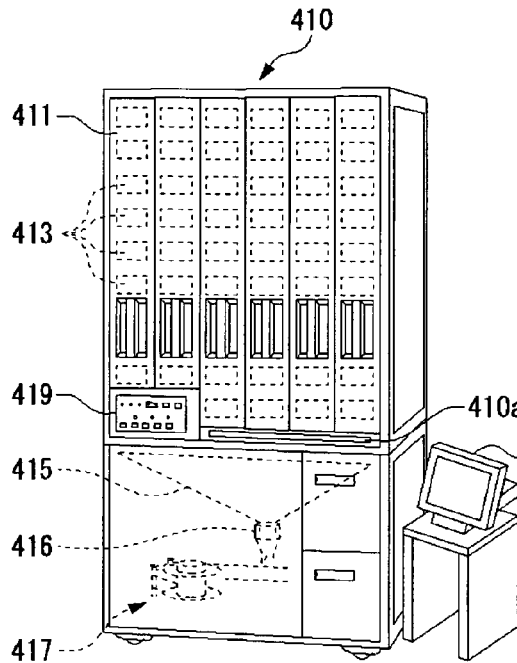
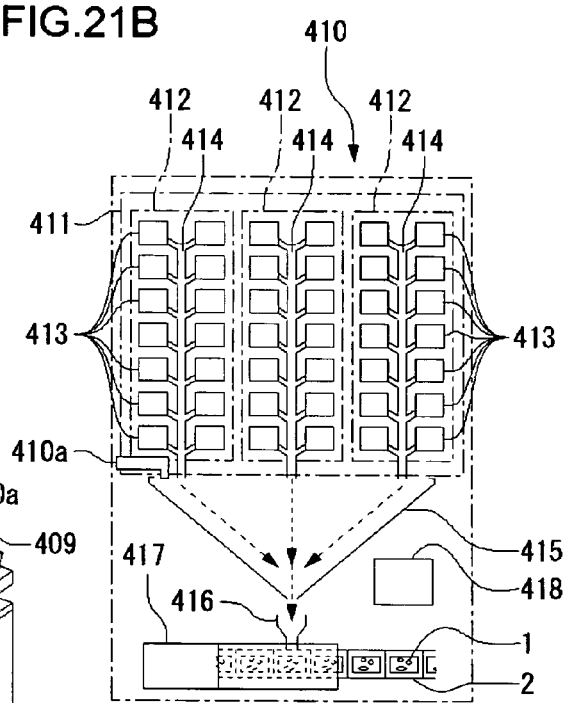
FIG.21C
FIG.21D
FIG.21E
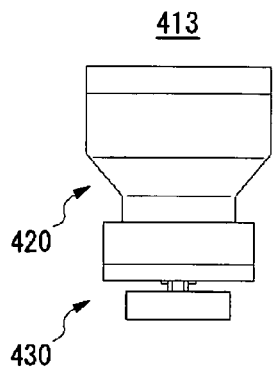
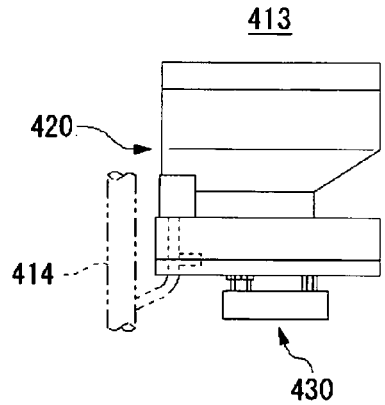
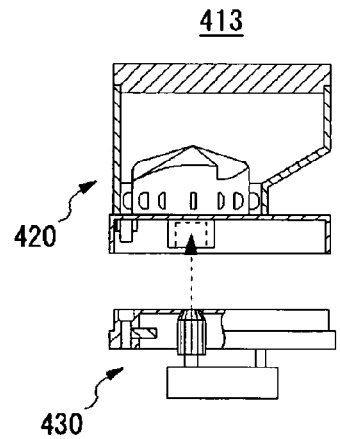
FIG.21F
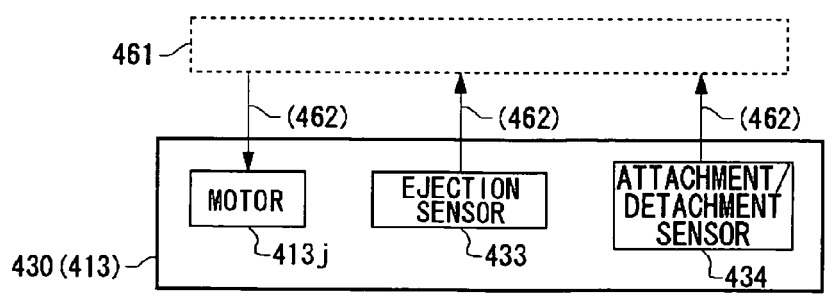

FIG.23A

DRUG MASTER TABLE

| DRUG CODE | DRUG INFORMATION | MACHINE 1 ID | CHECK DATA (CASSETTE IDENTIFICATION INFORMATION) | FEEDER STORAGE ADDRESS (COLUMN ADDRESS) (ROW ADDRESS) (BOARD ADDRESS) | CASSETTE STATE | |
|---|---|---|---|---|---|---|
| | | | CHECK DATA (CASSETTE IDENTIFICATION INFORMATION) | FEEDER STORAGE ADDRESS (COLUMN ADDRESS) (ROW ADDRESS) (BOARD ADDRESS) | CASSETTE STATE | |
| | | ⋮ | ⋮ | ⋮ | ⋮ | ⋮ |
| | | MACHINE N ID | CHECK DATA (CASSETTE IDENTIFICATION INFORMATION) | FEEDER STORAGE ADDRESS (COLUMN ADDRESS) (ROW ADDRESS) (BOARD ADDRESS) | CASSETTE STATE | |

(FREE AREA FOR FUTURE EXPANSION)

FIG.23B

DRUG EJECTION INSTRUCTION

| MACHINE n ID | FEEDER STORAGE ADDRESS (COLUMN ADDRESS) (ROW ADDRESS) (BOARD ADDRESS) | TABLET COUNT ETC. |
|---|---|---|

FIG.27A

DRUG MASTER TABLE

| DRUG CODE | DRUG INFORMATION | MACHINE 1 ID | CHECK DATA (CASSETTE IDENTIFICATION INFORMATION) | FEEDER STORAGE ADDRESS (COLUMN ADDRESS) (ROW ADDRESS) (BOARD ADDRESS) | CASSETTE STATE | AC FLAG |
|---|---|---|---|---|---|---|
| | | | CHECK DATA (CASSETTE IDENTIFICATION INFORMATION) | FEEDER STORAGE ADDRESS (COLUMN ADDRESS) (ROW ADDRESS) (BOARD ADDRESS) | CASSETTE STATE | AC FLAG |
| | | ⋮ | ⋮ | ⋮ | ⋮ | ⋮ |
| | | MACHINE N ID | CHECK DATA (CASSETTE IDENTIFICATION INFORMATION) | FEEDER STORAGE ADDRESS (COLUMN ADDRESS) (ROW ADDRESS) (BOARD ADDRESS) | CASSETTE STATE | AC FLAG |

FIG.27B

DRUG EJECTION INSTRUCTION (TO 613)

| MACHINE n ID | FEEDER STORAGE ADDRESS (COLUMN ADDRESS) (ROW ADDRESS) (BOARD ADDRESS) | TABLET COUNT ETC. | AC OFF |
|---|---|---|---|

FIG.27C

DRUG EJECTION INSTRUCTION (TO 730)

| MACHINE n ID | CHECK DATA (CASSETTE IDENTIFICATION INFORMATION) | TABLET COUNT ETC. | AC ON |
|---|---|---|---|

FIG.34A

DRUG MASTER TABLE

| DRUG CODE | DRUG INFORMATION | MACHINE 1 ID | CHECK DATA (CASSETTE IDENTIFICATION INFORMATION) | FEEDER STORAGE ADDRESS (COLUMN ADDRESS) (ROW ADDRESS) (BOARD ADDRESS) | CASSETTE STATE | |
|---|---|---|---|---|---|---|
| | | | CHECK DATA (CASSETTE IDENTIFICATION INFORMATION) | FEEDER STORAGE ADDRESS (COLUMN ADDRESS) (ROW ADDRESS) (BOARD ADDRESS) | CASSETTE STATE | |
| | | ⋮ | ⋮ | ⋮ | ⋮ | ⋮ |
| | | MACHINE N ID | CHECK DATA (CASSETTE IDENTIFICATION INFORMATION) | FEEDER STORAGE ADDRESS (COLUMN ADDRESS) (ROW ADDRESS) (BOARD ADDRESS) | CASSETTE STATE | |

(FREE AREA FOR FUTURE EXPANSION)

FIG.34B

DRUG EJECTION INSTRUCTION

| MACHINE n ID | FEEDER STORAGE ADDRESS (COLUMN ADDRESS) (ROW ADDRESS) (BOARD ADDRESS) | TABLET COUNT ETC. |
|---|---|---|

AUTOMATIC DRUG DISPENSER AND DRUG FEEDER

BACKGROUND OF THE INVENTION

1. Field of the Invention

The present invention relates to an automatic drug dispenser for automatically ejecting various drugs.

2. Description of the Related Art

In an automatic drug dispenser such as a tablet packing machine and an injection dispensing machine, drugs are accommodated in drug cassettes such as tablet feeders according to their categories. A desired amount of drug is taken out in accordance with a prescription or an instruction for dispensing based on the prescription. In a majority of types of dispensers, drug cassettes are detachable to facilitate refilling of drug cassettes with drugs. Means are provided to ensure that drug containers are attached only to their counterparts so as to prevent a container from being attached to an improper destination.

Such means may be a mechanical one that takes advantage of alignment between a key (projection) and a slot (hole). The following approach of reading identification information has been in the mainstream from the perspectives of cost, flexibility, expandability and miniaturization. In this approach, different drug cassettes are assigned different identification numbers. The number is read electronically or magnetically so that the result of reading is checked against preset check data. An alarm is issued in the event of a matching failure. Some drug dispensing systems are so arranged as to further ensure that the drug cassettes are properly positioned, while employing the aforementioned approach of reading identification information. This is achieved by conducting multiple checks that differ in the range of checking (see, for example, patent document No. 1).

[Patent document No. 1]

JP2002-272812 A

[Patent document No. 2]

JP2002-153541 A

[Patent document No. 3]

JP2002-154637

[Patent document No. 4]

Japanese Utility Model Publication 5-7601

[Patent document No. 5]

Japanese Utility Model Publication 5-7602

[Patent document No. 6]

JP06-080103

[Patent document No. 7]

JP11-206855 (first page)

[Patent document No. 8]

JP2003-31871

As the number of drug types is increased, the number of drug feeders stored is also increased. When there are as many as several hundred or more feeders, initial setting and preparation of check data are not easy.

The configuration of an ejecting member of the drug feeder should be adapted to the configuration of the drug (dosage form). Since the variety of dosage form is quite extensive, it is not easy to make available a full line-up of drug feeders adapted to the various dosage forms.

Accordingly, a technical problem to be solved is to improve an automatic drug dispenser so that preparation of check data and adaptation to dosage forms are easy, even if there are a large number of drug feeders of diverse configurations.

SUMMARY OF THE INVENTION

An automatic drug dispenser according to at least one embodiment comprises: a drug cassette which ejectably accommodates drugs; a base unit which detachably supports the drug cassette and drives a motor to eject drugs; a drug feeder storage which is designed to store a large number of base units; a reading device which is provided in each of the base units and reads identification information assigned to the drug cassette; and a checking means which compares a result of reading with pre-stored check data, wherein a set of a microprocessor and a memory, or a microprocessor with a built-in memory is mounted in each of the base units, and the checking means and the check data are built in each microprocessor in a distributed manner.

An automatic dispenser according to at least another embodiment may comprise: a drug cassette which ejectably accommodates drugs; a base unit which detachably supports the drug cassette and drives a motor to eject drugs; a drug feeder storage which accommodates a large number of base units; a reading device which is provided in each of the base units and reads identification information assigned to the drug cassette; and a checking means which compares a result of reading with pre-stored check data, wherein a set of a microprocessor and a memory, or a microprocessor with a built-in memory is mounted in each of the base units, and wherein, in addition to the checking means which compares pre-stored check data stored in the memory with a result of reading by the reading device, a check bypassing means which temporarily suspends checking function is built in the microprocessor.

An automatic dispenser according to at least still another embodiment may comprise: a drug cassette which ejectably accommodates drugs; a base unit which detachably supports the drug cassette and drives a motor to eject drugs; a drug feeder storage which accommodates a large number of base units; a reading device which is provided in each of the base units and reads identification information assigned to the drug cassette; a checking means which compares a result of reading with pre-stored check data; and a drug dispensing controller which prepares a drug ejection instruction by referring to prescription data or drug dispensing data derived therefrom and which uses the instruction for motor-driven ejection by the base unit, wherein the base units are classified in a first group comprising a relatively large number of base units and a second group comprising a relatively smaller number of base units, and wherein the drug dispensing controller preparing the drug ejection instruction includes, in the drug ejection instruction addressed to the first group, a drug feeder storage address related to the drug feeder storage, and includes, in the drug ejection instruction addressed to the second group, the check data.

A drug feeder according to the at least yet another embodiment may comprise: a drug cassette which ejectably accommodates drugs; a base unit which detachably supports the drug cassette and drives a motor to eject the drugs, wherein a reading device which reads identification information assigned to the drug cassette is provided in the base unit, a set of a microprocessor and a memory, or a microprocessor with a built-in memory is mounted in the base unit, wherein a checking means which compares check data stored in the memory with a result of reading by the reading device is built in the microprocessor, and wherein a check bypassing means which temporarily suspends checking function is built in the microprocessor.

According to the present invention, efficient and automated drug dispensing is achieved.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIG. 1A is a perspective view showing the appearance of a tablet packing machine according to a first embodiment of the present invention;

FIG. 1B is a schematic view showing the internal structure of the tablet packing machine according to the first embodiment;

FIG. 1C is a view showing the left side of one of a large number of drug feeders built in the tablet packing machine according to the first embodiment;

FIG. 1D is a front view of the drug feeder according to the first embodiment;

FIG. 1E is a longitudinal sectional view showing the left side of the drug feeder according to the first embodiment;

FIG. 1F is a bottom view of a drug cassette according to the first embodiment;

FIG. 1G is a top view of a base unit according to the first embodiment;

FIG. 1H is a block diagram related to communication inside the dispenser;

FIGS. 3A and 3B are decision tables for ranking information collected according to the first embodiment;

FIG. 4A shows the data structure of drug dispensing history information constituting history information according to the first embodiment;

FIG. 4B shows the data structure of attachment/detachment history information constituting the history information according to the first embodiment;

FIG. 5A shows the data structure of fabrication history information constituting the history information according to the first embodiment;

FIG. 5B shows the data structure of selection history information constituting the history information according to the first embodiment;

FIGS. 5C, 5D, and 5E are a top view and a front view of a tablet according to the first embodiment;

FIG. 16A shows the structure of a record in a drug master table;

FIG. 16B shows an instruction addressed to the first group and includes a drug feeder storage address;

FIG. 16C shows an instruction addressed to the second group and includes check data;

FIG. 21A is a perspective view showing the appearance of the tablet packing machine;

FIG. 21B is a schematic view showing the internal structure of the tablet packing machine;

FIG. 21C is a left side view of the drug feeder;

FIG. 21D is a front view of the drug feeder;

FIG. 21E is a longitudinal sectional view showing the left side of the drug feeder;

FIG. 21F is a control block diagram related to active components of the drug feeder;

FIG. 23A shows the structure of a record in a drug master table;

FIG. 23B shows the structure of an electronic message for an instruction for ejecting drugs;

FIG. 27A shows the structure of a record in a drug master table;

FIG. 27B shows an instruction addressed to the first group and includes a drug feeder storage address;

FIG. 27C shows an instruction addressed to the second group and includes check data;

FIG. 34A shows the structure of a record in a drug master table;

FIG. 34B shows the structure of an electronic message for an instruction for ejecting drugs;

DETAILED DESCRIPTION OF THE INVENTION

Figure 2:
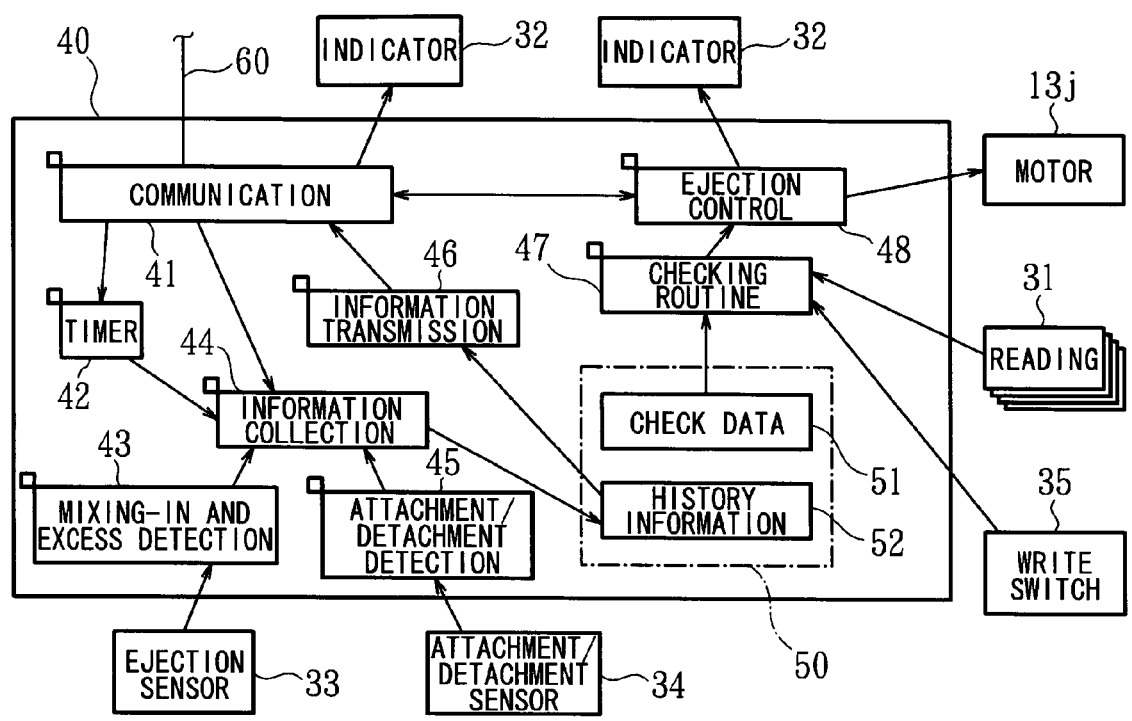
FIG. 2 is a functional block diagram of a microprocessor according to the first embodiment.

A description of the present invention will be given by highlighting five illustrative embodiments.

First Embodiment

The first embodiment relates to an automatic drug dispenser for accommodating various drugs and automatically ejecting a desired drug for purposes including packing, in accordance with a prescription or an instruction for dispensing and, more particularly, to an automatic drug dispenser in which it is checked if a drug cassette that ejectably stores a drug matches a base unit when the cassette is attached to or detached from the base unit.

A summary of the first embodiment will be given.

(1) An automatic drug dispenser according to a first embodiment comprises: a drug cassette which ejectably accommodates drugs; a base unit which detachably supports the drug cassette and drives a motor to eject drugs; a drug feeder storage which is designed to store a large number of base units; a reading device which is provided in each of the base units and reads identification information assigned to the drug cassette; and a checking means which compares a result of reading with pre-stored data, wherein a set of a microprocessor and a memory, or a microprocessor with a built-in memory is mounted in each of the base units, and the checking means and the check data are built in each microprocessor in a distributed manner.

(2) The automatic drug dispenser of (1) according to the first embodiment may further be characterized in that, if the result of comparison indicates matching failure, the same information as output when the associated drug cassette is empty is caused to be output, by suspending motor-driven ejection by the associated base unit.

(3) The automatic drug dispenser of (1) or (2) according to the first embodiment may further comprise an overwriting means which overwrites the check data with the identification information read by the reading device.

(4) The automatic drug dispenser of any one of (1) through (3) according to the first embodiment may be characterized in that the microprocessor is provided with a communication means, each of the base units is provided with a plurality of indicators of different colors such that at least one of the indicators displays a drug ejection enabled state and at least one other of the indicators displays a communication enabled state indicating that communication is enabled in the microprocessor.

(5) The automatic drug dispenser of any one of (1) through (4) according to the first embodiment may be characterized in that the microprocessor stores, in a memory, drug dispensing history information related to the operating condition of drug ejection by the associated base unit.

(6) The automatic drug dispenser of any one of (1) through (5) according to the first embodiment may be characterized in that the microprocessor stores, in a memory, attachment/detachment history information related to the attachment and detachment of a drug cassette to the associated base unit.

(7) The automatic drug dispenser of (5) or (6) according to the first embodiment may be characterized in that the microprocessor ranks, for storage, history information (drug dispensing history information and/or attachment/detachment history information) according to whether the information is related to normal operation or abnormal operation.

(8) The automatic drug dispenser of any of (1) through (7) according to the first embodiment may be characterized in that the microprocessor stores, in a memory, selection history information related to the selection of specification of the associated drug cassette.

(9) The automatic drug dispenser of any one of (1) through (8) according to the first embodiment may be characterized in that the microprocessor stores, in a memory, fabrication history information related to the fabrication process of the associated drug cassette.

(10) The automatic drug dispenser of any one of (5) through (9) according to the first embodiment may be characterized in that the microprocessor comprises a transmitting means which transmits the history information stored in the memory outside the dispenser.

In the automatic drug dispenser of (1), a microprocessor or the like with a built-in checking means and check data is mounted on a base unit to which a drug cassette is attached, in addition to a reading device for reading identification information assigned to the drug cassette. With this, the checking means and the check data are distributed among a large number of drug feeders so that a determination as to whether the drug cassette is properly attached can be made at each associated base unit.

By allowing a drug cassette to be checked for identification at the base unit of each drug feeder, correspondence between subjects of checking is directly confirmed by visual observation. Accordingly, preparation of check data is easier than otherwise. Thus, according to this aspect of the invention, there is provided an automatic drug dispenser in which preparation of check data is easy even if there are a large number of drug feeders.

In an automatic drug dispenser of (2), the base unit suspends the motor-driven ejection by the base unit in the event of a matching failure. In association with this, information indicating that the drug cassette is empty is output. Control for suspending motor-driven ejection is easily exercised feeder by feeder. The base units of the drug feeders operate independently in, for example, outputting information indicating emptiness of the associated drug cassette. This results in a simple, easy-to-maintain system in comparison to a system with integrated, centralized control of the base units of the respective drug feeders.

With this, prevention of malfunction and issuance of an alarm on the basis of the result of checking are easily implemented by expanding the functions of the microprocessor installed in each drug feeder in a distributed manner.

In an automatic drug dispenser of (3), the identification information read by the reading device from the drug cassette attached to the base unit is used to overwrite the check data, by executing the overwriting means.

By enabling the check data to be set up in a state in which the corresponding drug cassette and base unit are actually combined, preparation of the check data is further facilitated.

In an automatic drug dispenser of (4), a drug ejection enabled state in which ejection of the drug is enabled and a communication enabled state in which communication in the microprocessor is enabled are indicated by different colors and at respective locations. With this, visual confirmation of abnormality is facilitated.

In an automatic drug dispenser of (5), drug dispensing history information related to the operating condition of drug ejection is stored in each drug feeder. With this, it is easy to collect data that will be of use to confirm incompatibility between the dosage form and the drug cassette that may cause a trouble with ejecting operation.

This will allow a user to examine whether or not a trouble with the ejecting operation of a drug feeder is due to incompatibility between the dosage form and the drug cassette, by examining the drug dispensing history information stored in the drug feeder. If the trouble is due to incompatibility, it is possible to identify a cause and a countermeasure, allowing the user to switch to a drug cassette more suitable to the dosage form.

Thus, according to this aspect of the invention, it is possible to implement an automatic drug dispenser in which not only preparation of check data is easy but also compatibility with dosage form is easily established, even if there are a variety of drug feeders.

In an automatic drug dispenser of (6), attachment/detachment history information related to the attachment and detachment of a drug cassette is stored in each drug feeder. With this, the condition related to attachment and detachment of the drug cassette is easily referred to when examining the compatibility between the dosage form and the drug cassette. This will allow a user to examine whether or not a trouble with a drug feeder is due to incompatibility between the dosage form and the drug cassette, by examining the attachment/detachment history information stored. If the trouble is due to incompatibility, it is possible to identify a cause and a countermeasure, allowing the user to switch to a drug cassette more suitable to the dosage form. Thus, according to this aspect of the invention, it is possible to implement an automatic drug dispenser in which not only preparation of check data is easy but also compatibility with the dosage form is easily established, even if there are a variety of drug feeders.

In an automatic drug dispenser of (7), it is immediately known whether the drug dispensing history information or the attachment/detachment history information stored is related to a normal operation or an abnormal operation, by referring to the information. This will allow a user to examine whether or not a trouble with a drug feeder is due to incompatibility between the dosage form and the drug cassette, by examining the history information stored. If the trouble is due to incompatibility, it is possible to identify a cause and a countermeasure, allowing the user to switch to a drug cassette more suitable to the dosage form. Thus, according to this aspect of the invention, it is possible to implement an automatic drug dispenser in which not only preparation of check data is easy but also compatibility with the dosage form is easily established, even if there are a variety of drug feeders.

In an automatic drug dispenser of (8), selection history information related to the selection of specification of a drug cassette is stored in each drug feeder. With this, it is easy to refer to the specification of a drug cassette when examining compatibility between the dosage form and the drug cassette. This will allow a user to examine whether or not a trouble with a drug feeder is due to incompatibility between the dosage form and the drug cassette, by examining the selection history information stored. If the trouble is due to incompatibility, it is possible to identify a cause and a countermeasure, allowing the user to switch to a drug cassette more suitable to the dosage form. Thus, according to this aspect of the invention, it is possible to implement an automatic drug dispenser in which not only preparation of check data is easy but also compatibility with the dosage form is easily established, even if there are a variety of drug feeders.

In an automatic drug dispenser of (9), fabrication history information related to the fabrication process of a drug cassette is stored in each drug feeder. With this, it is easy to refer to the information related to the fabrication of the drug cassette when examining compatibility between the dosage form and the drug cassette. This will allow a user to examine whether or not a trouble with a drug feeder is due to incompatibility between the dosage form and the drug cassette, by examining the fabrication history information stored. If the trouble is due to incompatibility, it is possible to identify a cause and a countermeasure, allowing the user to switch to a drug cassette more suitable to the dosage form. Thus, according to this aspect of the invention, it is possible to implement an automatic drug dispenser in which not only preparation of check data is easy but also compatibility with the dosage form is easily established, even if there are a variety of drug feeders.

In an automatic drug dispenser of (10), various history information stored in the drug feeders in a distributed manner is transmitted outside the drug feeders. This allows a controller or the like responsible for operation control and data management of the automatic drug dispenser as a whole to collect the various history information for integrated management.

This will allow a cause and a countermeasure to be identified not only from a local perspective but also from an overall perspective. Therefore, it is possible to implement an automatic drug dispenser in which not only preparation of check data is easy but also compatibility with the dosage form is easily established, even if there are a variety of drug feeders.

A description will now be given of embodiments of the inventive automatic drug dispenser. First, a specific structure of a tablet packing machine 10, a typical embodiment of the inventive automatic drug dispenser, will be described with reference to the associated drawings. FIG. 1A is a perspective view showing the appearance of a tablet packing machine; FIG. 1B is a schematic view showing the internal structure of the tablet packing machine; FIG. 1C is a view showing the left side of one of a large number of drug feeders built in the tablet packing machine; FIG. 1D is a front view of the drug feeder; FIG. 1E is a longitudinal sectional view showing the left side of the drug feeder; FIG. 1F is a bottom view of a drug cassette; FIG. 1G is a top view of a base unit; and FIG. 1H is a block diagram related to communication inside the dispenser.

FIG. 2 is a functional block diagram of a microprocessor; FIGS. 3A and 3B are decision tables for ranking information collected. FIG. 4A shows the data structure of drug dispensing history information; FIG. 4B shows the data structure of attachment/detachment history information; FIG. 5A shows the data structure of fabrication history information; and FIG. 5B shows the data structure of selection history information. Each of FIGS. 5C-5C is a pair of top view and front view of a tablet, showing a dosage form that serves as a criterion for selecting a drug cassette.

The tablet packing machine 10 (see FIGS. 1A, 1B) comprises: a large number of drug feeders 13 accommodating various drugs 1 (disk-shaped drugs, ball-shaped drugs, capsules, cylinder-shaped drugs, tablets and the like) according to their categories; drug collecting mechanisms 14 and 15 for collecting the drugs 1 ejected from the drug feeders 13; a packaging apparatus 17 for packaging the drugs 1 received from the drug collecting mechanisms 14 and 15; and a controller 18 (main controller) embodied by a microprocessor system or the like.

Under the control of the controller 18, a desired number of drugs 1 are ejected from the associated drug feeders 13 in accordance with prescription data or drug dispensing instruction data derived therefrom. The drug collecting mechanisms 14 and 15 collect the drugs 1 thus ejected and feed them to a drug input unit 16 (collected drug input inlet) provided downstream so that the drugs 1 are packed in the packaging apparatus 17. The drugs 1 are packed in packing strip 2 (packing paper) as they are compartmentalized according to a unit to be taken at a time or a unit to be administered at a time.

In further detail, the tablet packing machine 10 houses a drug storage 11 (a drug rack unit and a drug container storage) at the upper end of the machine and also houses the packaging apparatus 17 at the lower end thereof. Conduit pipes 14 (ducts, chutes, guide passages, upper drug collecting channels) and collecting members 15 (hopper-like members, funnel form members, lower drug collecting channels) constituting the drug collecting mechanism communicate between the drug storage 11 and the packaging apparatus 17. In the drug storage 11, multiple individually slidable drug feeder storages 12 (drug storages) are arranged horizontally. In each of the drug feeder storages 12, several to several tens of detachable drug feeders 13 are arranged vertically and horizontally.

Each drug feeder 13 (see FIGS. 1C-1G) is generally partitioned into a drug cassette 20 ejectably accommodating a large number of drugs 1, and a base unit 30 detachably supporting the drug cassette 20 and driving a motor to eject drugs. The drug feeder 13 is designed to eject a designated number of drugs 1.

The drug cassette 20 is configured such that a container unit 13$b$ (a cup, a drug containing unit, a drug container) with a lid 13$a$ and an aligner 13$c$ (a rotor, an aligning member, an ejection member), which has partition walls 13$d$ (molded blades, blade-like projections, aligning members) provided at the circumference of the board, are secured to a casing board 13$e$ (joint unit for attachment and detachment). When the aligner 13$c$ is rotated via a cylindrical unit 13$g$ (detachable power transmitting member), the drugs 1 inside the container unit 13$b$ enter a space between the partition walls 13$d$ one after another so as to be aligned. The drugs 1 then fall one by one from an ejection outlet 13$f$.

The base unit 30 is provided with a base 13$k$ (basic securing member) fitted to the drug feeder storage 12, a motor 13$j$ (actuator) fixed to the base 13$k$, a spline shaft 13$i$ (detachable power transmitting member) joined to the rotating shaft of the motor 13$j$. In order to facilitate the attachment and detachment of the drug cassette 20, the base unit 30 is configured such that the spline shaft 13$i$ is engaged with the cylindrical unit 13$g$ as the cassette is attached so that, in the engaged state, the rotation of the motor 13$j$ is transmitted to the cylindrical unit 13$g$ via the spline shaft 13$i$. A through hole 13$h$ (drug falling passage) is formed in the base 13$k$ so as to communicate with the ejection outlet 13$f$ while the drug cassette 20 is being attached to the base unit 30.

A conduit pipe 14 is built in the drug feeder storage 12 so as to extend virtually through the center thereof in a vertical direction (see FIG. 1B). The ejection outlet 13$f$ of each drug feeder 13 communicates with the nearby conduit pipe 14 via the through hole 13$h$ of the base 13$k$ and a extension pipe etc. appropriately provided. The drug 1 ejected from the drug feeder 13 is led to the conduit pipe 14 via the through hole 13$h$ and then guided to the collecting member 15 after a free fall through the conduit pipe 14. The conduit pipe 14 is provided in each drug feeder storage 12. Thus, the conduit pipes 14 of the collecting mechanism constitute multiple guiding parts that run parallel with each other between a large number of drug feeders 13.

The collecting member 15 is built in the tablet packing machine at a location below the drug storage 11 and above the packaging apparatus 17. The upper-end opening thereof opens wide enough to cover the lower ends of all conduit pipes 14, while the lower-end opening thereof is narrowed down toward the drug input unit 16 of the packaging apparatus 17. All of the drugs 1 guided by the conduit pipes 14 are collected toward the lower-end opening before being forwarded to the packaging apparatus 17. Thus, the collecting member 15 of the collecting mechanism represents a common channel leading from the conduit pipes 14 to the packaging apparatus 17.

Under the control of the controller 18, the drugs 1 ejected from several of the drug feeders 13 fall to the collecting member 15 via the conduit pipes 14, in accordance with the operation in an operation panel 19 based on an instruction such as a prescription describing dosage, use, etc., or in accordance with a drug dispensing instruction given via an appropriate input device or a prescription ordering system (not shown). The drugs 1 ejected are collected by the collecting member 15 and ejected into the drug input inlet 16 of the packaging apparatus 17 through an exit at the bottom of the collecting member 15. The drugs 1 passing through the drug collecting channel are packed in packing strip 2 by a packaging apparatus 17. The packaging apparatus 17 feeds the packing strip 2 a predetermined length at a time and packs the drugs by heat sealing the strip. As described, the drugs 1 are automatically packed by being fed from associated drug feeders 13 to the packaging apparatus 17 via the collecting mechanisms 14 and 15 one by one or in units of multiple tablets.

Each drug feeder 13 is also provided with a checking means for reading and checking identification information in order to verify whether the drug cassette 20 attached is proper (see FIGS. 1C-1G). More specifically, the drug cassette 20 is provided with an identification information bearing member 21 for holding identification information. The base unit 30 is provided with a reading device 31 for reading identification information from the identification information bearing member 21 and with a microprocessor 40 of a one-chip type provided with a built-in memory. The identification information bearing member 21 is a sticker with a scanned surface on which, for example, a total of eleven white or black marks are arranged in a single row. The sticker is pasted to the underside of the drug cassette 20. The reading device 31 is configured such that as many reflective photosensors as the number of marks on the identification information bearing member 21 are also arranged in a single row. The reading device 31 is provided on top of the base unit 30. In a state in which the drug cassette 20 is attached to the base unit 30, the reading device 31 and the identification information bearing member 21 are opposite to each other to facilitate reading.

To allow each of the drug feeders 13 to check the identification information by using the result of reading by the reading device 31, the reading device 31 is connected to the microprocessor 40. A memory in the microprocessor 40 stores check data. The microprocessor 40 has a checking routine installed therein to check the result of reading by the reading device 31 against the check data (see FIG. 1H). The microprocessor 40 is further provided with a communication means comprising a communication circuit and a communication routine. The communication means is connected to an internal communication means 60 for wired or wireless LAN communication. In this way, the microprocessor 40 is capable of communicating with the controller 18.

Moreover, the base unit 30 is provided with multiple easily viewable indicators 32 (for example, green LEDs and red LEDs) to indicate the communication enabled state and drug ejection disabled state, etc. (see FIGS. 1C-1G). An ejection sensor 33 for detecting the drug 1 as it passes the through hole 13h is also provided. Further, although not shown in FIGS. 1A-1H, the base unit 30 is provided with an attachment/detachment sensor 34, such as a mechanical switch, for detecting whether the drug cassette 20 is attached to the base unit 30. A write switch 35 operated by maintenance personnel when initializing or updating check data is also provided where it is concealed in a small hole or the like. These components (32, 33, 34, 35) are also connected to the microprocessor 40 and are subject to its control.

To describe it in further detail, the memory 50 of the microprocessor 40 stores check data 51 and history information 52. Installed in the microprocessor 40 are: a communication routine 41 as a communication means; a timer routine 42 as a time management means for generating a time stamp; a mixing-in and excess detecting routine 43 as a drug dispensing abnormality detecting means for detecting trouble in drug ejection such as mixing-in or excess of drugs; an information collecting routine as a history information storage means; an attachment and detachment detecting routine 45 as a cassette attachment and detachment detecting means; an information transmitting routine 46 as a transmitting means; a checking routine 47 as a checking means and an overwriting means; and an ejection control routine 48 as a motor-driven ejection control means.

The communication routine 41 is for receiving an instruction from the controller 18 via the internal communication means 60 and transmitting status and data to the controller 18. Instructions received include a drug ejection instruction, a history information upload instruction, a history information download instruction and a time setting instruction. The drug ejection instruction includes the number of tablets to be ejected (numerical data) and is delivered to the ejection control routine 48. The history information upload instruction designates information to be uploaded, as selected from: drug dispensing history information; attachment/detachment history information; fabrication history information; and selection history information described later. More specifically, the history information upload instruction designates one of, all of or some of these types of information. The designated information is delivered to the information transmitting routine 46.

The history information download instruction includes fabrication history information and/or selection history information. The communication routine 41 delivers the information to the information collecting routine 44. The time setting instruction is prepared such that the controller 18 includes in the instruction appropriate serial data indicating time managed by a clock in the controller 18. The time setting instruction is periodically sent to the microprocessors 40 all at once. The communication routine 41 delivers the received time setting instruction to the timer routine 42. The communication routine 41 turns on a green indicator constituting the indicators 32 if communication is enabled. If not, the green indicator 32 is prevented from being turned on.

The timer routine 42 locally manages time (runs a clock) by using a clock built in the microprocessor 40 or an external clock, or by using periodical interrupts. The timer routine 42 generates a time stamp by referring to the time and supplies the time stamp to the information collecting routine 44. Moreover, when the time setting instruction is delivered from the communication routine 41, the timer routine 42 adjusts time which is managed by the timer routine 42 for generation of a time stamp.

The mixing-in and excess detecting routine 43 prepares selected drug dispensing history information related to the operating condition of motor-driven ejection by the base unit 30 in which the microprocessor 40 is provided, selection being made according to whether the information should be stored. More specifically, the mixing-in and excess detecting routine 43 receives a detection output from the ejection sensor 33 and transfers the same to the ejection control routine 48. The mixing-in and excess detecting routine 43 further checks the result of ejection detection for compatibility with the driving condition of the motor 13j as detected by the control routine 48. If the ejection of the drug 1 is detected in the absence of the driving of the motor 13j, a determination that undesired "mixing-in" occurs. The mixing-in and excess detecting routine 43 generates drug dispensing history information that includes information indicating the incident and the time provided by the timer routine 42. The mixing-in and excess detecting routine 43 delivers the time and the information to the information collecting routine 44 for storage.

If the number of drugs 1 ejected exceeds the number designated by the drug ejection instruction when the motor 13j is driven, the mixing-in and excess detecting routine 43 determines that undesirable "excess" occurs. The mixing-in and excess detecting routine 43 generates drug dispensing history information that includes information indicating the incident and the time provided by the timer routine 42. The mixing-in and excess detecting routine 43 delivers the time and the information to the information collecting routine 44 for storage. When the number of drugs 1 ejected when the motor 13j is driven is equal to the number designated by the drug ejection instruction, it means that incompatibility does not occur. In this case, the mixing-in and excess detecting routine 43 does nothing. If the ejection of a drug other than the drug designated by the drug ejection instruction is detected when the motor 13j is driven, the mixing-in and excess detecting routine 43 determines that undesired "mixing-in" occurs. The mixing-in and excess detecting routine 43 generates drug dispensing history information that includes information indicating the incident and the time provided by the timer routine 42. The mixing-in and excess detecting routine 43 delivers the time and the information to the information collecting routine 44 for storage.

The attachment/detachment detecting routine 45 prepares, for storage, attachment/detachment history information related to the attachment and detachment of the drug cassette 20 to the base unit 30 in which the microprocessor 40 is provided. More specifically, the attachment/detachment detecting routine 45 receives a detection output from the attachment/detachment sensor 34 so as to detect that the cassette 20 is attached to or detached from the base unit 30, by referring to a variation in the detected value or by referring to a significant signal output at attachment or detachment. The attachment/detachment detecting routine 45 generates attachment/detachment history information that includes information indicating the incident and the time provided by the timer routine 42. The attachment/detachment detecting routine 45 delivers the time and the information to the information collecting routine 44 for storage.

If the history information download instruction received from the communication routine 41 includes fabrication history information, the information collecting routine 44 appends the included information to the history information 52. If the history information download instruction includes selection history information, the information collecting routine 44 appends the included information to the history information 52. If the history information download instruction includes time (time stamp data), the history information is stored as it is. If not, the time provided by the timer routine 42 is appended before storing the history information.

The information collecting routine 44 also stores data in the history information 52 when drug dispensing history information is received from the mixing-in and excess detecting routine 43 or when attachment/detachment history information is received from the attachment/detachment detecting routine 45. In this case, prior to the storage in the history information 52, the information is ranked to make it easy to understand whether the information stored is related to normal operation, abnormal operation or intermediate therebetween. The rank is appended to the information before appending the information to the history information 52. The criteria for ranking and the data structure of drug dispensing history information, attachment/detachment history information, fabrication history information and selection history information will be described later in detail with reference to the drawings.

Upon receipt of the history information upload instruction from the communication routine 41, the information transmitting routine 46 delivers the designated items of the history information 52 stored in the memory 50 and also requests the communication routine 41 to transmit the delivered information outside as a response. If the history information 52 includes multiple items stored as records, record by record transmission is repeated for sequential transmission of history information, unless otherwise specified by the history information upload instruction. If a record number or time zone is designated, only the associated history information item is transmitted.

Upon receipt of the drug ejection instruction from the communication routine 41, the ejection control routine 48 causes the motor 13j to be rotated. When the ejection sensor 33 detects that as many drugs 1 as designated by the drug ejection instruction have been ejected, the ejection control routine 48 suspends the rotation of the motor 13j. If the action of ejection cannot be completed in a predefined time, it is determined that ejection is disabled. In this case, a red indicator constituting the indicators 32 is turned on. Otherwise, the red indicator constituting the indicators 32 is prevented from being turned on so as to indicate a drug ejection enabled state. When a transition occurs from an ejection enabled state to an ejection disabled state, or when a transition occurs from an ejection disabled state to an ejection enabled state, a status report that includes the state and state transition is generated at an appropriate point of time specified by an apparatus parameter or the like relative to status report. The communication routine 41 is requested to transmit the status report outside.

At the time of attaching the drug cassette 20 to the base unit 30 and, optionally, at an appropriate point of time during an operation for attaching the cassette as well, the checking routine 47 compares the check data 51 stored in the memory 50 with the result of reading by the reading device 31. The check data 51 is formed, for example, as 11-bit data, like the marks on the identification information bearing member 21, so that it is immediately known whether or not the data matches the result of reading by the reading device 31 by comparison. If the result of comparison indicates matching failure, the checking routine 47 uses a flag or the like to instructs the ejection control routine 48 to suspend motor-driven ejection by the associated base unit 30. The ejection control routine 48 receiving the instruction prevents the rotation of the motor 13*j* even if it receives the drug ejection instruction from the communication routine 41.

If the result of scanning the identification information bearing member 21 and the check data 51 in the memory 50 match, the checking routine 47 cancels an instruction for suspending motor-driven ejection given to the ejection control routine 48. In association with this, the ejection control routine 48 resumes the rotation of the motor 13*j* in accordance with the drug ejection instruction from the communication routine 41. In this way, undesired ejection of the drug 1 is prevented in case an incompatible cassette 20 is attached to the base unit 30. Such a state is handled as one of ejection disabled state, which is indicated by the red indicator 32 accordingly. Further, a status report is provided via the internal communication means 60. Thus, the drug feeder 13 is designed to output the same information as output when the drug cassette 20 is empty.

The check data 51 is written in the memory 50 using a data writing tool such as a general-purpose ROM writer or a dedicated writer. A stand-alone memory 50 may be temporarily installed in the tool to write specified data in a specified address. It will be convenient and error free, though, to attach a compatible drug cassette 20 to the base unit 30 and transfer the identification information to the memory 50. For this purpose, the checking routine 47 also serves the function of a means for overwriting the check data 51, in addition to serving as the checking means. When the write switch 35 is operated, the reading device 31 reads the identification information from the identification information bearing member 21 of the drug cassette 20 then attached to base unit 30 so that the check data 51 is overwritten with the identification information thus read.

A detailed description will now be given of criteria for ranking undertaken by the information collecting routine 44 and the data structure of the various types of history information. The criteria for ranking will first be described (see FIGS. 3A and 3B). Specifically, two decision tables are used depending on the situation. The first decision table (see FIG. 3A) is used when the attachment/detachment history information is available immediately before mixing-in or excess occurs. The second decision table (see FIG. 3B) is used when the attachment/detachment history information is not available immediately before mixing-in or excess occurs. In either case, the rank is determined in accordance with whether mixing-in occurs, excess occurs and attachment/detachment of a cassette occurs. The ranks may be labeled as A, B, C, D and E, where A indicates a highly critical and emergent abnormality, E indicates a normality that helps analyzes abnormality and B-D indicate intermediate.

The drug dispensing history information (see FIG. 4A) constituting the history information 52 is data that relates to the operating condition of motor-driven ejection by the associated base unit 30. More specifically, a record of drug dispensing history information comprises a time stamp, abnormal operation data indicating mixing-in or excess and the rank determined by the aforementioned criteria. Records are stored in the order of occurrence.

The attachment/detachment history information (see FIG. 4B) constituting the history information 52 is data that relates to the attachment and detachment of the drug cassette 20 to and from the corresponding base unit 30. More specifically, a record of attachment/detachment history information comprises a time stamp, attachment/detachment data indicating whether the cassette is attached or detached and the rank determined by the aforementioned criteria. Records are stored in the order of occurrence.

The fabrication history information (FIG. 5A) constituting the history information 52 is data that relates to fabrication processes of the corresponding drug cassette 20. More specifically, a record of fabrication history information comprises a time stamp indicating time when a fabrication process is undertaken, a process ID defined for each stages of the fabrication process and the ID of personnel in charge of the process. Records are stored in the order of occurrence. The factory history information is written in a factory of a manufacturer and so a dedicated tool is used for that purpose. For example, when the tool is connected to the internal communication means 60 in conjunction with the drug feeder 13, the tool transmits a series of history information download instructions to the communication routine 41 of the microprocessor 40 in the drug feeder 13, via the internal communication means 60.

The selection history information constituting the history information 52 (FIG. 5B) is data that relates to the selection of the specification of the corresponding drug cassette 20. More specifically, a record of selection history information comprises a time stamp indicating time when a specification is selected or re-selected, dosage form data indicating the dosage form of the drug 1 contained in the drug cassette 20 by a symbol, capsule data indicating whether the drug 1 is contained in a capsule and compatibility data indicating whether the aligner 13*c* and the partition walls 13*d* match any of those listed in a standard list and, if so, a number in the list. Records are stored in time series each time a specification is selected. When the selection history information is written in a factor of a manufacturer, a dedicated tool is used as described above. When a user writes the data after the tablet packing machine 10 is delivered to the user, the operation panel 19 is used. A program (not shown) for supporting the operation is installed in the microprocessor 40.

Some typical examples of tablet configurations listed in the dosage form data will be given. A disk-shaped tablet with a regular thickness is referred to as "type F" (see FIG. 5C). A tablet which is basically disk-shaped but is thicker toward the center is referred to as "type FR" (see FIG. 5D). A tablet which appears round in a top view and elliptical in a front view is referred to as "type R" (see FIG. 5E).

It is assumed here that the information only indicates whether the drug 1 is contained in a capsule or not. Alternatively, the selection history information may include the configuration and material of a capsule.

The standard list for compatibility is worked out in details including the size as well as the dosage form of tablets and capsules. The list is designed so that each of the aligner 13*c* and the partition walls 13*d* is identified by a number in the list if it is a standard component. Since there are a variety of sizes and configurations of the aligner 13*c* and the partition walls 13*d*, the standard list reflecting those naturally contains a large number of sublists. The standard list itself is not stored in the memory 50. What is stored as part of the history information 52 in the memory 50 is a number in the list.

Features that characterize the fabrication of the tablet packing machine 10 according to the first embodiment, as well as the type of use and operation of the machine fabricated will now be described. The type of use and operation will be described in relation to a normal state, an occasion of drug refill and an occasion of re-selection of the drug cassette 20.

A difference from the related-art fabrication of the tablet packing machine 10, particularly in relation to the drug feeder 13, is that the identification information bearing member 21 is pasted to the drug cassette 20, the base unit 30 is provided with the reading device 31, the indicators 32, the ejection sensor 33, the attachment/detachment sensor 34 and the microprocessor 40. The checking means and the check data are built in the microprocessor 40 and the memory 50 in a distributed manner. Other routines mentioned above are also installed in the microprocessor 40. The internal communication means 60 is connected to the microprocessor 40.

Further, in the process of fabricating the base unit 30 and the drug cassette 20 attached to the base unit 30, time and personnel ID are recorded in a process management document or the like each time a process is completed. When the microprocessor 40 of the base unit 30 is communication-enabled and is enabled to process a history information download instruction, a dedicated tool is used to write the fabrication history information in the memory 50. Subsequently, the fabrication history information is written using the dedicated tool each time a process is completed. When the aligner 13c of the like is selected in fabricating the drug cassette 20, the associated selection history information is written in the memory 50 of the microprocessor 40 in the associated base unit 30 using a dedicated tool.

After the tablet packing machine 10 is fabricated, the tablet packing machine 10 is installed at a hospital dispensary or the like. In a normal state, the controller 18 refers to prescription data or drug dispensing instruction data derived from the prescription data so as to send a drug ejection instruction to the microprocessor 40 of the base unit 30 in the associated drug feeder 13. A designated number of drugs 1 are ejected from the associated drug cassette 20. The ejected drugs are collected by the drug collecting mechanism 14 and 15 and packed in the packing strip 2 by the packaging apparatus 17. Drug ejection and packing are as described are repeated automatically.

A time setting instruction is also repeatedly sent from the controller 18 via the internal communication means 60 so that the microprocessor 40 receiving the instruction adjusts time. In a normal state in which communication and drug ejection are properly performed, the green indicator 32 is lighted and the red indicator 32 is prevented from being lighted in each of the drug feeders 13. Therefore, it is possible to visually confirm that no abnormality occurs in the drug feeders 13. When, for example, the internal communication means 60 is malfunctioning, resulting in communication being disabled and in the suspension of operation of the tablet packing machine 10, the green indicator 32 is prevented from being lighted. With this, the cause of the trouble is easily identified.

When any of the drug cassettes 20 is empty, the state is detected by the ejection control routine 48 of the microprocessor 40 in the base unit 30 to which the drug cassette 20 is attached. The result of detection is reported to the controller 18 via the communication routine 41. The red indicator 32 is also lighted. Thus, the fact that there is an empty drug cassette 20 and the location thereof can be properly known by personnel by an alarm sounded by the controller 18 and/or the lighting of the indicator 32. If the drug to fill the cassette is not immediately available, an instruction as to whether packing should proceed without the drug or automatic drug dispensing based on the outstanding prescription should be terminated is given to the controller 18 via the operation panel 19 or the like. When the drug to fill the cassette is immediately available, the cassette is refilled.

In refilling the drug cassette 20 with the drug 1, the empty drug cassette 20 is removed from the base unit 30. The drugs 1 are contained in the container unit 13b. Thereafter, the drug cassette 20 is reattached to the base unit 30. Both when attaching the drug cassette 20 and when detaching the same, the detecting routine 45 and the information collecting routine 44 of the microprocessor 40 of the base unit 30 to which the drug cassette 30 is attached append attachment/detachment history information to the history information 52 record by record. Further, when the drug cassette 20 is reattached, the identification information is read from the identification information bearing member 21 by the reading device 31. The checking routine 47 compares the result of reading with the check data 51.

If the result of comparison indicates matching failure, the ejection control routine 48 maintains an ejection disabled state in accordance with a notification from the checking routine 47. Accordingly, there is no fear that inappropriate drugs may be ejected for dispensing, even if a non-compatible drug cassette 20 is attached. In the event that the red indicator 32 is not prevented from being lighted when the drug cassette 20 is attached, compatibility of the drug cassette 20 is rechecked. An appropriate drug cassette 20 is attached to the base unit 30.

Once an appropriate drug cassette 20 is attached, the comparison will find that the result of scanning the information bearing member 21 matches the check data 51 from the memory 50. Ejecting operation control by the ejection control routine 48 is resumed. A report indicating that the drug feeder 13 has returned to a drug ejection enabled state is sent from the ejection control routine 48 to the controller 18. The red indicator 32 is also lighted. Ejection of drugs is then resumed.

In the related art, there may be cases where the drug cassette 20 with a selected aligner 13c proves to be incompatible with the drug contained in the cassette. For example, this may occur when the dosage form was not accurately known before the specification of the drug cassette 20 is determined, or when the dosage form was changed before the tablet packing machine 10 is put into actual use. In these cases, undesirable events such as mixing-in and excess may occur. Occurrence of such events is rare and at irregular intervals. It is therefore difficult to locate and identify such events even with monitoring. In a majority of cases, such events are identified by a check after the drug is dispensed.

In contrast, with the drug feeder 13 of the inventive tablet packing machine 10, an occurrence of abnormal ejection that involves mixing-in or excess is detected by the mixing-in and excess detecting routine 43. The information is ranked by the information collecting routine 44 so as to create a record of drug dispensing history information, which is then appended to the history information 52. When mixing-in or excess of drugs is found in a check performed after the drugs are dispensed, the situation in which the abnormality occurs is learned. This is achieved, in the case of a site, by operating the operation panel 19 of the tablet packing machine 10. In the case of a remote location such as a factory of a manufacturer, the history information upload instruction is sent to the microprocessor 40 of the drug feeder 13 via the controller 18, using an external communication means connected to the tablet packing machine 10 such as the Internet or a lease line.

Each of the aforementioned actions prompts the history information 52 in the memory 50 to be sent by the information transmitting routine 46 via the internal communication means 60. In the case of a site, the drug dispensing history information and the attachment/detachment history information are displayed on a screen of the operation panel 19. In the case of a remote location, the drug dispensing history information and the attachment/detachment history information are displayed on a browser screen or the like. The information displayed may be referred to identify a cause of the mixing-in or excess. If necessary, the selection history information and the fabrication history information are also displayed on a screen to help the personnel to arrive at a solution. Since the situation is known easily and readily at a site or at a remote location, maintenance personnel arriving at the site can quickly act upon the situation. When the personnel at the site cannot make a proper decision or has difficulty in addressing the situation, an advice, instruction or assistance is transmitted from a remote location to the site. Since the site and the remote location can pursue a common task, sharing common understanding based on the same information, the task can proceed promptly and properly in a favorably coordinated manner.

When the aligner 13c or the like of the drug cassette 20 is re-selected, the new drug cassette 20 is attached to the destination base unit 30 and the write switch 35 is operated. This causes the identification information to be read by the reading device 31 from the identification information bearing member 21. The check data 51 is overwritten with the result of reading by the checking routine 47. With this, the drug cassette 20 is made compatible with the destination base unit 30. Further, the operation panel 19 is operated so as to append the selection history information including the specification data of the re-selected drug cassette 20 to the history information 52 in the memory 50 of the associated microprocessor 40.

Thus, when the drug cassette 20 is exchanged or the specification of the drug cassette 20 is changed after the tablet packing machine 10 is put into operation, associated updating of the check data 51 and storage of the history information 52 are easily and properly performed at the site.

The added information is also displayed on a screen for reference when the situation of operation is assessed or the specification is changed subsequently.

[Other Points of Note]

The drug feeders 13 may not necessarily be arranged vertically and horizontally to form a matrix as described above. A cylindrical arrangement may alternatively be employed.

The drug feeder storage 12 may be movable. The microprocessor 40 may not necessarily be of a one-chip type. The memory 50 may be externally provided. While it is preferable that the memory 50 be non-volatile, it may alternatively be a memory provided with a battery.

The writing of the check data 51 by operating the write switch 35 may not necessarily be done at the site but may be done during the fabrication in a factory.

In the described example, the mixing-in and excess detecting routine 43 receives the result of detection by the ejection sensor 33 and notifies the ejection control routine 48 accordingly. Conversely, the ejection control routine 48 may detect abnormality in the motor 13j and notifies the mixing-in and excess detecting routine 43 accordingly. Alternatively, a dedicated routine may be provided to receive the result of detection by the ejection sensor 33 and may used to notify both the mixing-in and excess detecting routine 43 and the ejection control routine 48 accordingly.

Second Embodiment

The second embodiment relates to an apparatus wherein a drug product of a dosage form (for example, tablet and capsule) that allows piece-by-piece handling (in this specification, such a drug product is referred to as a "drug") is contained in a container. The apparatus feeds a prescribed number of drugs outside the container in accordance with a control signal.

In a hospital dispensary or a prescription pharmacy outside a hospital, prescribed types and quantity (dose at a time, dosing interval, dosing period in number of days, etc.) of drugs are given to a patient in accordance with a prescription prepared by a doctor. In a dispensary or a pharmacy dispensing drugs such as tablets and capsules, a drug feeder (also referred to as a "tablet feeder") is used as an apparatus for automatically selecting drugs designated in each prescription from a large stock of drugs (see, for example, patent documents 2-5).

The drug feeder 13 is provided with a container for containing drugs and is a mechanism designed to feed contained drugs piece by piece in accordance with a control signal consistent with a prescription.

As shown in FIG. 7 of patent document No. 3, a drug feeder (reference numeral 13 in the figure) is an assembly comprising parallel-arranged units each capable of feeding one type of drug, the number of units being commensurate with the number of types of drugs to be stocked. The assembly is configured such that an arbitrary drug feeder is selectively operated by a controller. Drugs ejected from the drug feeder are collected by a chute (the duct 14 and the collecting member 15 in the figure) in one location. This enables a desired combination of drugs to be retrieved in accordance with a prescription. Below the chute is provided a packaging apparatus (reference numeral 17 in the figure) for individual packaging of drugs in a serial film package. The large number of drug feeders and the packaging apparatus integrally form a drug packing apparatus (tablet packing machine 10 in the figure).

In a hospital dispensary or the like, this drug packing apparatus enables a required amount of drugs to be fed from corresponding drug feeders only by inputting prescription data. It is possible to film-pack each one tablet or to automatically package and serve a multiple types of drugs to be taken at a time.

As shown in FIG. 10 of patent document No. 3, each drug feeder is provided with a feed mechanism for feeding contained drugs one by one. FIG. 11 shows a main part of a typical, favorable feed mechanism in a related-art drug feeder adapted to capsules.

As shown in FIG. 11, the related-art drug feeder is comprised of a container main body 100 and an aligner 200. The container main body 100 comprises a cell unit 110 for containing drugs and an aligner housing unit 120 adjacent to the bottom of the cell unit 110. Normally, the container 100 is formed of a semitransparent plastic so that the amount of drugs remaining in the container is visually observable.

In the illustrated example, the aligner housing unit 120 is of a cylindrical configuration with a vertical axis of rotation. The aligner 200 (particularly, a main body 210) is rotatably contained in the aligner housing unit 120. In the illustrated example, the main body 210 of the aligner 200 is of a cylinder configuration rotatably engageable with the aligner housing unit 120. The main body 210 is axially arranged to be aligned with the aligner housing unit 120. The top of the main body of the aligner is formed as a spirally projecting agitator unit 240. The agitator 240 projects into the cell unit 110 and operates to agitate capsules and guide them into gutters described later.

The underside of the aligner 200 is connected to an external driving apparatus (not shown) so as to be rotated, a rotation angle in each step of rotation being defined by a single gutter described later.

At least one gutter 220 is provided at the periphery of the aligner 200 so that the drug enters the gutter 220 via the cell unit 110. A partition 230 between the gutters is referred to in patent document No. 3 as a blade-like projection 13d.

The gutter 220 extends in a direction having a vertical component. As shown in FIG. 11, the depth and width of the gutter are determined such that the longest dimension (total length) L10 of a capsule is aligned with the direction of extension of the gutter, i.e. such that the capsule falls in a longitudinal direction.

The aligner housing unit 120 of the container main body is configured to have a height H10, which is greater than the total length of the gutter 220. With this, the gutter 220 is covered over its entire length by the wall of the aligner housing unit, producing a tubular passage surrounded on all sides, and properly functions as a gutter.

The total length of the gutter 220 is at least twice as large as the total length L10 of the capsule contained. At a position spaced apart from the bottom of the gutter 220 by the total length of the capsule, a partition plate 300 projects from selected locations on the interior wall of the aligner housing unit 120. The partition plate 300 partitions the gutter 220 into a preparatory aligning unit 221 in the top half and an aligning unit 222 in the bottom half.

More specifically, as shown in FIG. 11, the gutter 220 is designed to be of a length in which two successive capsules are completely entrenched therein. It is ensured that the lower aligning unit 222 is of a gutter length equal to the total length L10 of a capsule and the upper preparatory aligning unit 221 is of a gutter length equal to or greater than the total length L10 of a capsule. In the example of FIG. 11, the total length of the gutter 220 is twice the total length of a capsule. In a case where the gutter 220 is adapted to accommodate a small capsule, however, the gutter length of the preparatory aligning unit 221 may be greater than the total length of a capsule.

The significance of having the preparatory aligning unit 221 preceding the aligning unit will be described later.

A notch is provided in the center of all partitions at the periphery of the aligning unit so that the partition plate 300 can reach the neighborhood of the bottom of the gutter. With this, the aligner 200 can be rotated without being interfered by the partition plate 300.

Immediately beneath the gutter provided with a partition plate, a drug outlet 400 is provided at the bottom of the aligner housing unit. By providing a partition plate, it is ensured that the cell space, the gutter in the aligning unit and the drug outlet are not aligned to communicate with each other. Only those capsules in the aligning unit 221 that are introduced into a space immediately above the drug outlet (=immediately below the partition plate) fall under their own weight to the drug outlet 400 so as to fall to the external chute. Without the partition plate, the drug can freely fall into the aligning unit immediately above the drug outlet, there being no limit to the number of drugs ejected from the drug outlet.

The preparatory aligning unit is located between the cell unit of the container main body, the agitator unit of the aligner projecting into the cell unit, and the aligning unit which includes the drug outlet. The guiding action of the agitator enables the preparatory aligning unit to receive drugs from the cell unit properly and feed the drugs to the aligning unit. That is, the preparatory aligning unit is a standby aligning unit preceding the aligning unit.

As mentioned with reference to the partition plate, the top end of the gutter should be closed by the partition plate when the drug is introduced into a space immediately above the drug outlet. Accordingly, in an embodiment provided only with the aligning unit (i.e., an embodiment in which the preparatory aligning unit is absent), the chance of drugs in the cell falling into the gutter is reduced due to blockage by the partition plate. In contrast, by providing the preparatory aligning unit, drugs in the cell can fall into all gutters over the entire periphery of the aligner. As such, the chance of drugs in the cell falling into the gutters is not reduced. It is also for a probabilistic reason as mentioned above that the structure with the preparatory aligning unit is favorable in properly guiding drugs in the cell into the gutters.

For the purpose of feeding drugs in the cell to the preparatory aligning unit, the gutter width and/or gutter depth are designed such the minimum of the three dimensions (total length, total width and total thickness) of the associated drug can pass through the gutter. With this dimension control, it is ensured that the drug enters the gutter only in such a manner that the direction of the longest dimension (normally, the direction of the total length) is aligned with the longitudinal direction of the gutter. Like the aligning unit, the gutter of the preparatory aligning unit may suitably be formed in accordance with the size of one of the dimensions (total length, total width and total thickness) of the drug 1 with an intermediate size. The gutter width of the preparatory aligning unit is determined in accordance with the intermediate dimension. That is, if the gutter width is too large with respect to the intermediate dimension of the drug 1, the drug 1 will not be settled in the gutter of the preparatory aligning unit in a stable manner. Conversely, when the gutter width is too small with respect to the intermediate dimension of the drug 1, the drug 1 is prevented from entering the preparatory aligning unit properly.

Conventionally, the preparatory aligning unit is provided in a case where the drug is of an elongated configuration (for example, a capsule) in which the intermediate dimension is generally smaller than ½ of the maximum dimension.

As mentioned above, it is ensured in the related-art drug feeder that the total length of the gutter of the aligner is at least twice the total length of a drug of an elongated configuration, and the preparatory aligning unit with a gutter length greater than the total length of the drug is provided. Further, container main bodies with the aligner housing units of a variety of heights are formed to adapt to the total length of the gutter of the aligner.

Thus, various types of aligners and container main bodies with different dimensions adapted to a variety of total lengths of drugs are prepared and are appropriately combined to adapt to the total lengths of drugs. In this way, drug feeders corresponding to a variety of dimensions of capsules and tablets are produced.

The inventors of the present invention studied the structure of the related-art drug feeder as described above and found that there are two problems (A) and (B) to be resoled.

(A) The first problem is that the height of the aligner housing unit 120 would become excessively large in order to deliver a relatively elongated drug such as that of Japanese pharmacopoeia #000 (total length=about 22 mm), preventing formation of a compact feeder. This is because the structure of the related-art drug feeder requires that the total length of the gutter of the aligner and the height of the aligner housing unit be twice or larger than the total length of a drug so as to secure a space for the preparatory aligning unit.

(B) The second problem is that a wide variety of components constituting drug feeders (particularly, container main bodies) adapted to a variety of total lengths of drugs should be prepared because the total length of drug differs significantly from one drug type to another.

For example, in the case of #000 capsules (for illustrative purpose, the total length of 20 mm is assumed), the height of the aligner housing unit of the container main body should be 40 mm, twice the total length of the capsule. In the case of a #5 capsule (for illustrative purposes, the total length of 10 mm is assumed), the required height of the aligner containing unit would be 20 mm, twice the total length of the capsule.

Thus, the height of the aligner housing unit would be 40 mm or 20 mm depending on the capsule accommodated, the size at one extreme being twice that of the other. If tablets with a diameter of, for example, 5 mm are also to be fed, the size range of the aligner housing unit will further be increased.

Figure 12:
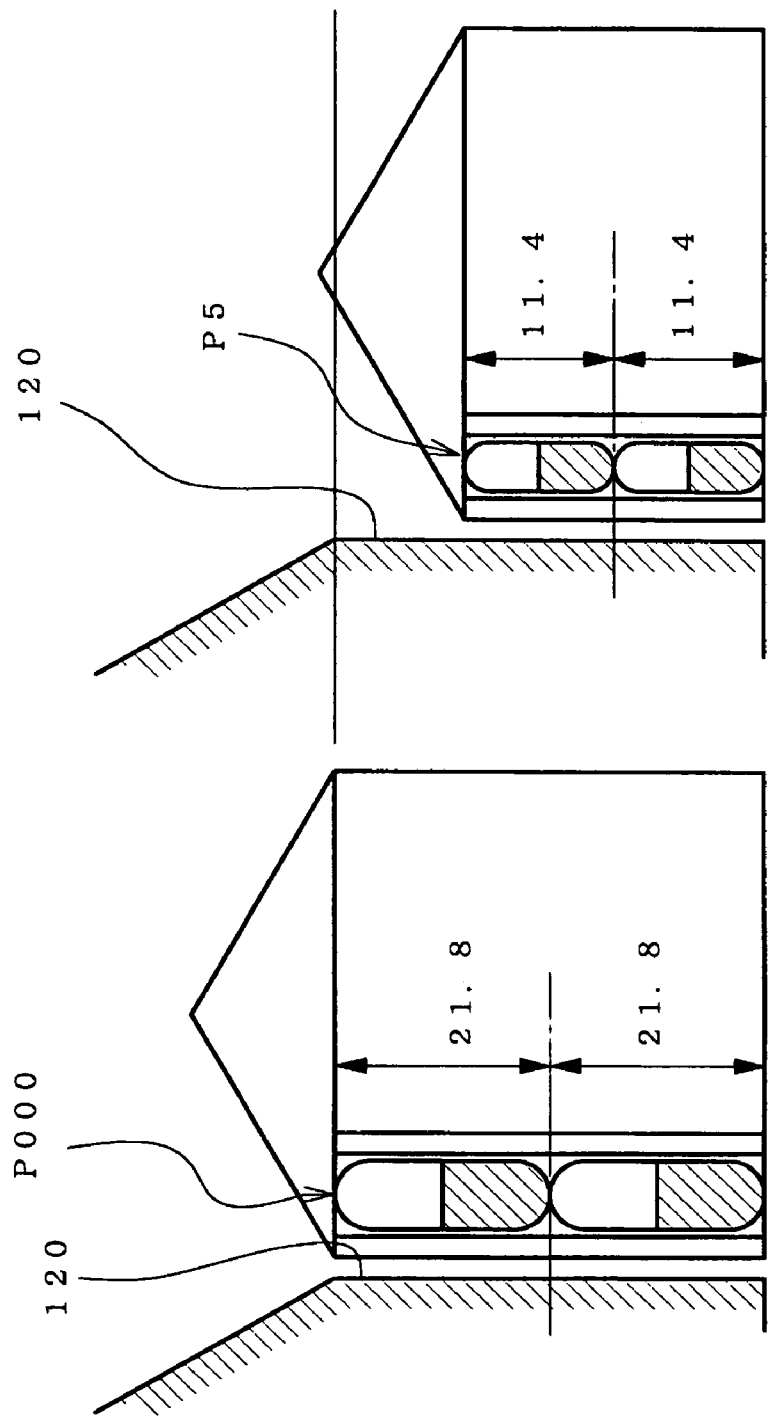
FIG. 12 relates to the second embodiment and illustrates a problem with the related-art drug feeder.

For example, it is possible to enforce diversion in which a container main body having an aligner housing unit adapted to relatively large-sized #000 is used to accommodate relatively small-sized #5 capsules. As shown in FIG. 12, such diversion, characterized by large size mismatch, results in the top end of the aligner housing unit 120 for #000 capsules (reference symbol P000) facing the wall being approximately 20 mm above the top end of the gutter of the aligner for #5 capsules (reference symbol P5). Since the cell opens upward at the top end of the aligner housing unit, this results in drug accommodating space being wasted.

The second embodiment, which will be described below, relates to a method of providing a drug feeder in which the aforementioned problem is solved and in which the container main body is made more compact in the height direction than in the related art. The second embodiment also relates to a method of providing an assembly of drug feeders in which it is possible to use a uniformly-sized container main body even if the total length differs from drug to drug.

A summary of the second embodiment will be given.

While the gutter length of the preparatory aligning unit is ensured to be at least equal to the total length of a drug in the related art, we have found that the function of preparatory aligning unit is fully served even if the gutter length is reduced to a size shorter than the total length of a drug.

The following features characterize the second embodiment.

(1) A drug feeder for containing and feeding a drug, comprising: a container main body and an aligner, wherein the container main body comprises: a cell unit which contains a drug; and an aligner housing unit which is adjacent to the bottom of the cell unit and which rotatably accommodates a main body of the aligner, at least one gutter into which a drug enters via the cell unit is provided at the periphery of the aligner, the gutter extends in a direction having a vertical component, and the depth and width of the gutter are determined such that the longest dimension of a drug is aligned with the direction of extension of the gutter, a partition plate projects from the interior wall of the aligner housing unit so as to partition the gutter into a preparatory aligning unit in the top half and an aligning unit in the bottom half, a drug outlet is provided in the aligner housing unit at a position below the partition plate so as to allow a drug in the aligning unit to fall, designating the longest dimension of a drug as its total length L, the gutter length of the aligning unit is substantially equal to the total length L, and the gutter length of the preparatory aligning unit is smaller than the total length L.

(2) The drug feeder as described in (1) above, in which the aligner is generally of a cylindrical forms and a space inside the aligner housing unit is of a cylindrical form having an inner diameter sufficiently large to rotatably accommodate the aligner.

(3) The drug feeder as described in (1) above, in which the drug is as described later in (A) or (B).

(4) An assembly of drug feeders which contain and feed a drug, wherein each drug feeder comprises a container main body and an aligner, each drug feeder is dedicated to a particular one of drug types that differ in dimensions so that each feeder contains and feeds only one type of drug, the container main body comprises: a cell unit which contains a drug; and an aligner housing unit which is adjacent to the bottom of the cell unit and which rotatably accommodates a main body of the aligner, at least one gutter into which a drug enter via the cell unit is provided at the periphery of the aligner, the gutter extends in a direction having a vertical component, and the depth and width of the gutter are determined such that the longest dimension of a drug is aligned with the direction of extension of the gutter, a partition plate projects from the interior wall of the aligner housing unit so as to partition the gutter into a preparatory aligning unit in the top half and an aligning unit in the bottom half, a drug outlet is provided in the aligner housing unit at a position below the partition plate so as to allow a drug in the aligning unit to fall, designating the longest dimension of a drug as its total length L, and given a drug Px having a total length Lx, which is equal to a maximum total length L of drugs of a variety of dimensions, the gutter of the aligning unit is of a length Ax, which is practically equal to the total length Lx, and the gutter of the preparatory aligning unit is of a length Bx, which is smaller than the total length Lx, and given a drug P other than the drug Px, the gutter of the aligning unit is of a length which is practically equal to the total length L of the drug P, and the gutter of the preparatory aligning unit is equal to or smaller than (Ax+Bx−L).

(5) The assembly of drug feeders as described in (4) above, in which the aligner is generally of a cylindrical form, and a space inside the aligner housing unit is of a cylindrical form having an inner diameter sufficiently large to rotatably accommodate the aligner.

(6) The assembly of drug feeders as described in (5) above, in which the container main body of the same form is used for drugs with different dimensions, and the height H of the cylinder of the aligner housing unit is less than twice the total length Lx of the drug Px.

(7) The assembly of drug feeders as described in (4) above, in which the drug Px is as described later in (A) or (B).

(8) The assembly of drug feeders as described in (4) above, in which the partition plate is formed as a component separate from the container main body and inserted into the cylindrical space from outside the container main body so as to be detachably secured in the container main body.

(A) A drug of a form with different dimensions in all three mutually perpendicular directions (x, y, z), in which, designating the largest dimension as a total length L and the remaining two dimensions as a total width W and a total thickness T, the total length L is at least twice the larger of the total width W and total thickness T.

(B) A drug of a form in which one of the dimensions in the three mutually perpendicular directions (x, y, z) is longer than the other two dimensions and the remaining two dimensions are equal to each other, and in which, designating the longest dimension as a total length L and the remaining two dimensions as a total width W and a total thickness T, the total length L is at least twice the total width W.

Hereinafter, a design feature adapted to a relatively large total length of drug (for example, Japanese pharmacopoeia #000-#0 capsules) will be referred to by a term "large-length" (for example, "large-length aligner"). A design feature adapted to a relatively small total length of drug (for example, #3-#5 capsules) will be referred to by a term "short-length".

The gutter length of the preparatory aligning unit provided in the aligner of the related-art drug feeder is such that [gutter length of preparatory aligning unit=total length of drug]. In the second embodiment, however, [gutter length of preparatory aligning unit<total length of drug]. This is based on our finding that the function of guiding drugs is properly served even if the gutter length of a preparatory aligning unit is shorter than the total length of a drug.

Broadly speaking, reduction in the gutter length of a preparatory aligning unit produces the following two effects.

Firstly, by enabling the height of an aligner and the height of an associated aligner housing unit of a container main body to be reduced, the total height of the container main body, i.e., the height of a drug feeder as a component is reduced accordingly. Alternatively, by maintaining the total height of the container main body unchanged from that of the related art while reducing the height of the aligner and aligner housing unit, the capacity of the cell is enlarged accordingly.

Secondly, by reducing the height of a large-length aligner and aligner housing unit and not reducing the height of a small-length aligner (i.e., not reducing the height of a preparatory aligning unit), size difference between the height of a large-length aligner housing unit and the height of a small-length aligner is reduced. As a result of this, the waste of accommodating space due to size difference as described in (B) above is reduced in scale even if a large-length container main body is used as a small-length container main body. In other words, a large-length container main body can also serve the purpose of a small-length container main body. By using a large-length container main body also as a small-length container main body, it is not necessary to prepare a stock of a large variety of container main bodies in the process of fabricating a drug packing apparatus, which is an assembly of drug feeders. This allows the use of only one kind of die to produce of a container main body and is favorable in that the cost of fabricating a drug packing apparatus is reduced.

The drug feeder according to the embodiment (1) described above and the assembly according to the embodiment (4) described above will be sequentially described by citing preferred embodiments of a drug feeder and an assembly thereof. In the following description, the longest dimension of a drug will be referred to as a total length L.

Figure 6:
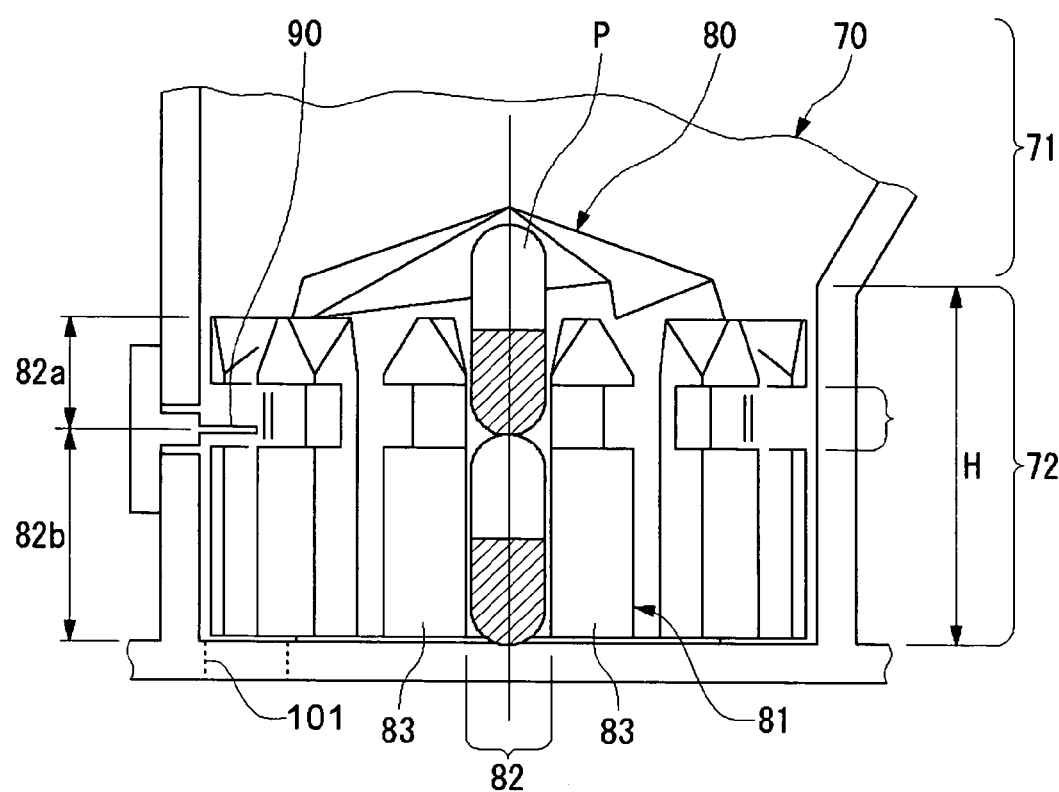
FIG. 6 shows the structure of a drug feeder according to a second embodiment of the present invention, where a container main body is illustrated using a sectional view and an aligner is illustrated using an outline drawing.

As shown in FIG. 6, the drug feeder according to the embodiment (1) comprises a container main body 70 and an aligner 80. Reference symbol P indicates a drug handled by the drug feeder (a capsule is illustrated as an example).

For the basic structure of the drug feeder (for example, the structure described in (a)-(f) below and the materials of feeder components) and for the workings and effects described in (g) below and obtained by such structures, the related-art structure described above using FIG. 11 or the description in patent documents 2-5 may be referred to.

(a) The container main body 70 comprises a cell unit 70 and an aligner housing unit 72 adjacent to the bottom thereof.

(b) At least a main body 81 of the aligner 80 is rotatably accommodated in the aligner housing unit 72.

(c) Gutters 82 are provided at the periphery of the aligner 80 to sandwich partition walls 83. The gutter 82 extends in a direction having a vertical component. In the example shown in FIG. 6, the gutter 82 extends in the vertical direction.

(d) The top of the aligner is formed as an agitator spirally projecting upwards. A connecting hole or a connecting shaft is provided on the underside of the aligner for connection to an external driving apparatus.

(e) A partition plate 90 projects from selected locations on the interior wall of the aligner housing unit 72 so as to partition the gutter 82 into a preparatory aligning unit 82a and an aligning unit 82b.

(f) A drug outlet 101 is provided in the aligner housing unit below the position of the partition plate so as to ensure that drugs in the aligning unit fall under their own weight.

(g) The workings and effects of the drug feeder provided by the basic structure in (a)-(f) are as follows: a large number of drugs randomly accommodated in the cell unit 71 descend to the gutter 82 of the aligner 80 and reach the aligning unit. As the aligner is rotated, only those drugs guided to positions immediately below the partition plate fall to an external chute via the drug outlet 101 under their own weight.

As described before, an important feature of the drug feeder according to this embodiment consists in the gutter length of the preparatory aligning unit.

As shown in FIG. 6, the gutter length of the preparatory aligning unit 62a according to the second embodiment is shorter than the total length L of the drug P. That is, the drug P entering the preparatory aligning unit 82a is not completely accommodated in the preparatory aligning unit as shown in FIG. 6, if there is a drug in the aligning unit below. A portion of the drug projects above the top of the gutter into the cell unit. The preparatory aligning unit such as this is not found in the related art but provides the function equivalent to that of the related-art preparatory aligning unit, if the gutter length is properly limited.

The gutter length of the aligning unit 82b is practically the same as the total length L of the drug P, as in the related art. The term "practically the same" refers to a requirement that the gutter length be practically equal to the length L such that a difference is within a range of error permitted to achieve the purpose of the drug feeder according to the second embodiment. The total length of a finished drug is not strictly as designed and the actual gutter length of the aligning unit 82b also has a manufacturing error.

As described earlier, our finding in the second embodiment is that the function of a preparatory aligning unit is properly served even if the gutter length of the preparatory aligning unit is configured to be shorter than the total length of a drug as described above. By configuring the gutter length of the preparatory aligning unit to be shorter as described above, the height of the aligner housing unit 72 is reduced accordingly, resulting in a drug feeder which is compact in height. Accordingly, the problem described above in (a) is solved. An added advantage is that the capacity of accommodating drugs is increased. Described above are the features of the embodiment (1).

The embodiment (1) requires that the gutter length of a preparatory aligning unit be smaller than the total length L of a drug. To achieve highly compact size of a drug feeder as a whole and to enable the configuration of a container main body to be shared as much as possible as described in the embodiment (4), it is preferable that the gutter length of a preparatory aligning unit be 80% or smaller, and preferably, 60& or smaller, than the total length L of a drug.

The minimum gutter length of a preparatory aligning unit is preferably 40% or greater and, more preferably, 45% or greater than the total length L of a drug handled, to ensure that the gutter provides the function as a preparatory aligning unit.

Drugs handled by the drug feeder according to the second embodiment, i.e. drugs contained in the cell unit for feeding may be of any type of solid drug product that can be fed one by one. For example, capsules, tablets (including uncoated tablets and sugar-coated tablets), pills and troches may be handled. Drugs handled may not necessarily be pharmaceuticals but may be what is categorized as food such as nutritional supplements.

Of all drugs, drugs having an elongated form as described in (A) and (B) above are most suitable to appreciate the feature of the drug feeder according to the second embodiment.

Figure 7A:
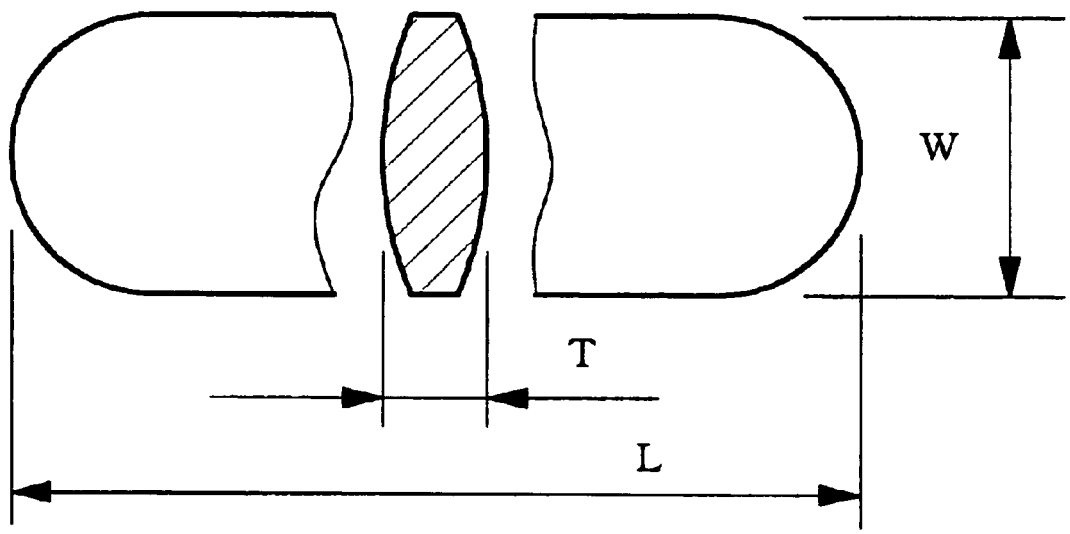
FIG. 7A shows the appearance of an elongated drug in which the total length L is at least twice the larger of the total width W and the total thickness T (in the illustrated example, the width W is larger than the thickness T)

As shown in FIG. 7A, the drug described in (A) above is an elongated drug in which the total length L is at least twice the larger of the total width W and the total thickness T (in the illustrated example, the width W is larger than the thickness T).

The form of drug shown in FIG. 7A is merely by way of example. The cross section indicated by shading is of a form having flat side edges and swollen toward the center. Alternatively, the cross section may be elliptical, rectangular, etc.

Figure 7B:
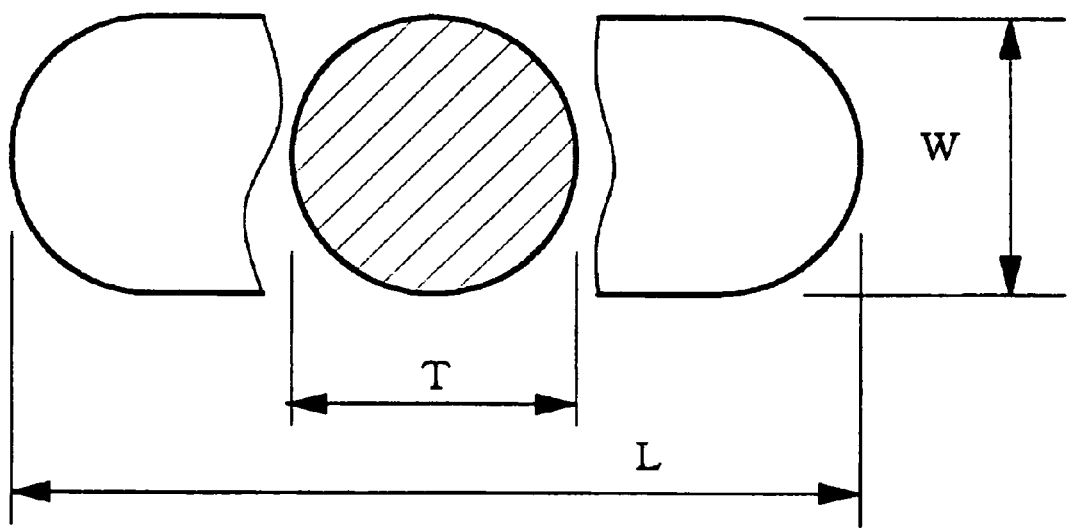
FIG. 7B shows the appearance of a drug in which a dimension indicated by L is longer than the other two dimensions T and W, where T is equal to W, and in which the total length L is at least twice the total width W (=the total thickness T)

As shown in FIG. 7B, the drug described in (B) above is a drug in which a dimension indicated by L is longer than the other two dimensions T and W, where T is equal to W, and in which the total length L is at least twice the total width W (=the total thickness T).

Capsules are typical examples of the drug of this type. The embodiment is not restricted to specific cross section or dimensions of a capsule. Capsules used for general-purposes include Japanese pharmacopoeia #000 capsules, #00 capsules and #0-#5 capsules. For example, a #000 capsule has a total length of about 22.02 mm, and a #5 capsule has a total length of about 9.40 mm.

The gutter 82 provided at the periphery of the aligner may be formed by machining a base material of the aligner or by joining ridged projection to the aligner to form a partition.

The requirement for the gutter 82 is that it extends in a direction having a vertical component so that drugs fall under their own weight. As shown in FIG. 6, the depth and width of the gutter 82 are determined such that the longest portion of a drug (in the case of a capsule, the total length L and, in the case of a disk-shaped drug, a diameter) is oriented in the direction of the extension of the gutter.

The basic form of the aligner is a body of revolution. Preferably, the aligner is of a cylindrical form in which the axis of rotation extends in a vertical direction. Alternatively, the aligner may be of a conical form with its vertex facing downward (see patent documents 4 and 5) or a conical form with its vertex facing upward. The direction of the axis of rotation preferably extends in a vertical direction. Alternatively, the direction may be changed as appropriate so long as drugs can fall to the drug outlet. As a result of employing the above-identified form, it is ensured that the gutter extends in a direction having a vertical component so that drugs fall under their own weight.

It is preferable that the space inside the aligner housing unit match the basic form of the aligner and the inner diameter of the space be sufficiently large to allow the aligner to be rotated. The posture of falling drugs may be determined in accordance with a distance between the interior wall surface of the aligner housing unit and the interior bottom surface of the gutter.

In the embodiment (1) described above, dimensions may be determined as required apart from the reduction in the size of the preparatory aligning unit. For example, the height of the aligner and the height of the aligner housing unit of the container main body may be determined as required so as to be most suitable for drugs.

If the need for standardization of the dimensions of components is disregarded and consideration is given only to the ideal form of a drug feeder as an isolated component, it is preferable the height of the aligner housing unit in the container main body (dimension H of FIG. 6) be practically equal to the total length of the gutter of the aligner (gutter length of the preparatory aligning unit 82*a*+gutter length of the aligning unit 82*b* of FIG. 6). More preferably, the dimension H is longer than the total length of the gutter of the aligner by 0 mm-5 mm, as shown in FIG. 6.

That is, an ideal relation between dimensions is such that H≧82*a*+82*b*.

A description will now be given of the embodiment (4) described above.

This embodiment requires that an assembly comprising multiple drug feeders according to the second example includes at least one drug feeder of the embodiment (1) above. From the perspective of standardization of the dimensions of the container main body, it is preferable that the aligner of the drug feeder of the embodiment (1) above be used for large-length drugs and the related-art aligner be used for small-length drugs. The basic mechanism and structure of each of the drug feeders required for feeding drugs are the same as those described with reference to the drug feeder of the embodiment (1) above.

Figure 8:
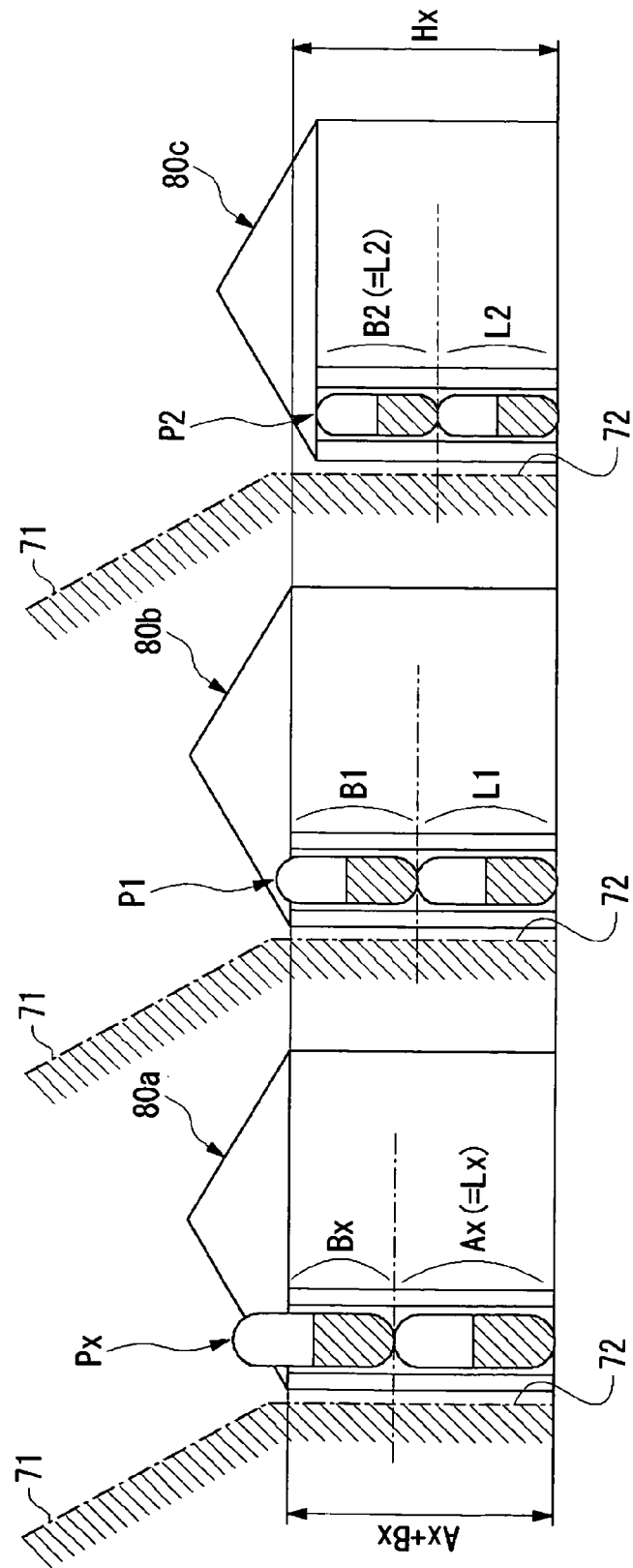
FIG. 8 schematically shows the relationship between selected dimensions occurring in the drug feeder according to the second embodiment.

FIG. 8 schematically shows the relationship between selected dimensions in aligners 80*a*, 80*b* and 80*c* of the drug feeder according to the embodiment (4), by taking examples of largest-length, medium-length and smallest-length drugs. As shown in FIG. 8, each of the drug feeders is dedicated to a particular one of drug types that differ in dimensions so that each feeder contains and feeds only one type of drug.

In forming an assembly comprising a multiple drug feeders according to the embodiment (4) above, the gutter length of the preparatory aligning unit of the aligner for largest-length drugs is reduced and the height of the aligner housing unit of the container main body is reduced accordingly. The gutter length of the preparatory aligning unit of the aligner for drugs shorter than a certain length is not reduced. A container main body for large-length drugs is also used in this case. With this, the size of the container main body is advantageously standardized and the problem of (B) is resolved.

More specifically, as shown in FIG. 8, the gutter of the preparatory aligning unit of the aligner 80*a* adapted for a drug Px having a total length Lx, which is a maximum total length L of drugs that differ in dimensions, is configured to have a length Bx, which is smaller than the total length Lx of the drug. The gutter of the aligning unit is of a length Ax, which is practically equal to the total length Lx of the drug, with the result that the gutter length of the largest-length aligner is such that Ax+Bx(=Lx+Bx)<2Lx.

The feature described above is the same as the feature of the drug feeder according to the embodiment (1) above. The amount of reduction of the gutter length of the largest-length preparatory aligning unit is as described in the embodiment (1) above.

The height Hx of the largest-length aligner housing unit is similarly reduced. The height Hx may be less than twice the total length Lx of the drug Px. Preferably, the height Hx is practically equal to Ax+Bx (=Lx+Bx), the total gutter length of the aligner or larger than the sum by about 0 mm-5 mm.

It is most preferable according to this embodiment that the reduced height Hx of the largest-length aligner housing unit be applied to other feeders so that the height Hx=Ax+Bx (=Lx+Bx) is uniformly used as the height of the aligner housing units of other container main bodies.

The total gutter length of the aligners for drugs (P1 and P2 of FIG. 8) shorter than the drug Px may preferably be designed as described (i) and (ii) below.

(i) In the case of drugs like the drug P1 of FIG. 8, which is slightly shorter than the largest-length drug Px (i.e. drugs in which twice the total length L1 of the drug is equal to or larger than the total length Ax+Bx of the largest-length gutter), the total length of the gutter of the aligner is designed to be Ax+Bx. In this case, the length B1 of the preparatory aligning unit is shorter than the total length L1 of the drug so that the resultant drug feeder is encompassed by the embodiment (1) above.

(ii) In the case of drugs like the drug P2 of FIG. 8, which is sufficiently shorter than the largest-length drug Px (i.e. drugs in which twice the total length L2 of the drug is smaller than the total length of the largest-length gutter Ax+Bx (=Lx+Bx)), the total length of the gutter of the aligner is made shorter than Ax+Bx but the size of the preparatory aligning unit is not reduced, the total length thereof remaining twice the length L2. In this structure, a difference between the height H (=Ax+Bx) of the aligner housing unit 72 of the container main body and the total length (=2×L2) of the gutter of the aligner 80c is not as large as in the related art. Thereby, the space of the cell unit is less wasted.

The total length of the gutter of the aligner 80b shown in FIG. 8 employed in the case of (i) above is Ax+Bx (=Lx+Bx), the same length as that of the aligner 80a. Unlike the aligner 80a, however, the gutter length of the aligning unit is L1 and the gutter length of the preparatory aligning unit is Bx+Lx−L1 (subtraction of the gutter length L1 of the aligning unit from the total length of Lx+Bx), to be more specific. That is, the level of reduction in the gutter length of the preparatory aligning unit is relatively small, with the result that the gutter length of the preparatory aligning unit is close to the total length L1 of the associated drug P1.

As mentioned in (i) and (ii) above, in a preferable embodiment, the total length of the gutter of the aligner associated with the drug shorter than the drug Px is equal to or smaller than Ax+Bx (=Lx+Bx). In that case, the gutter length of the preparatory aligning unit is equal to or smaller than (Ax+Bx−L), given that the total length of the drug is L.

If the total length of the drug is shorter than half the length (Ax+Bx) as in the case of drugs like the drug P2 shown in FIG. 8 (that is, in the case of a drug in which twice the total length of the drug is smaller than Ax+Bx), the total length of the gutter may be extended to Ax+Bx, if it is intended, for example, to standardize the size of a material worked to fabricate an aligner. In that case, the gutter length of the preparatory aligning unit is larger than the total length of the drug.

If the total length of a drug is sufficiently small as in the case of the drug P2 shown in FIG. 8 (for example, Japanese pharmacopoeia #5 capsules), collective behavior (such as manner in which the drugs fall into the aligner, resistance to movable components inside the container) of small-sized, lightweight drugs, occurring when the cell unit is filled with a large number of drugs, is different from that of the largest-length drug Px. As a result, the drugs may completely fall into the gutter even if only the aligning unit is provided. That is, the preparatory aligning unit may not be necessary. In such a case, the preparatory aligning unit may be omitted so that an aligner provided only with an aligning unit (a so-called single-tier blade) may be used. The aligner provided only with an aligning unit is favorable in that it is easy to machine and provides a larger space for accommodating drugs inside the container.

In order to achieve the structure according to embodiment (4) above, the preparatory aligning unit for drugs with the largest length of all types of drugs handled by the assembly is preferably designed to have the smallest possible gutter length. The total length of the gutter of the aligner as determined by the gutter length is given as (Ax+Bx), as described before. The height of the aligner housing unit is made to match the length (Ax+Bx). The dimensions of the container main bodies for other drug types are also determined according to the same sizing requirement.

For example, a Japanese pharmacopoeia #000 capsule (total length=about 22 mm) may be given as an example of the drug Px with the largest length Lx of all types of differently-sized drugs. When #000 capsules are handled, the gutter length of the preparatory aligning unit is preferably in the range of 40%-60% and, more preferably, 40%-50% of the total length of the capsule. By reducing the height of the aligner housing unit of the container main body accordingly, the container main body with the same dimensions is suitably used for drug feeders adapted for drugs shorter than the largest-length capsule.

As described above, the embodiment (4) above enables the use of a uniformly-sized container main body for an assembly of drug feeders. However, the specific detail of the total length of the gutter of the aligner (gutter length of the preparatory aligning unit/the gutter length of the aligning unit) differs depending on the total length of the drug. Therefore, the height of the partition plate provided in each container main body differs from feeder to feeder. Thus, even when the dimensions of the container main body are standardized, the height of the partition plate should be adjusted for each container main body.

By introducing a structure in which the position of the partition plate is changeable with a single operation, the container main body with uniform dimensions is suitably used for drugs with different total lengths.

Figure 9:
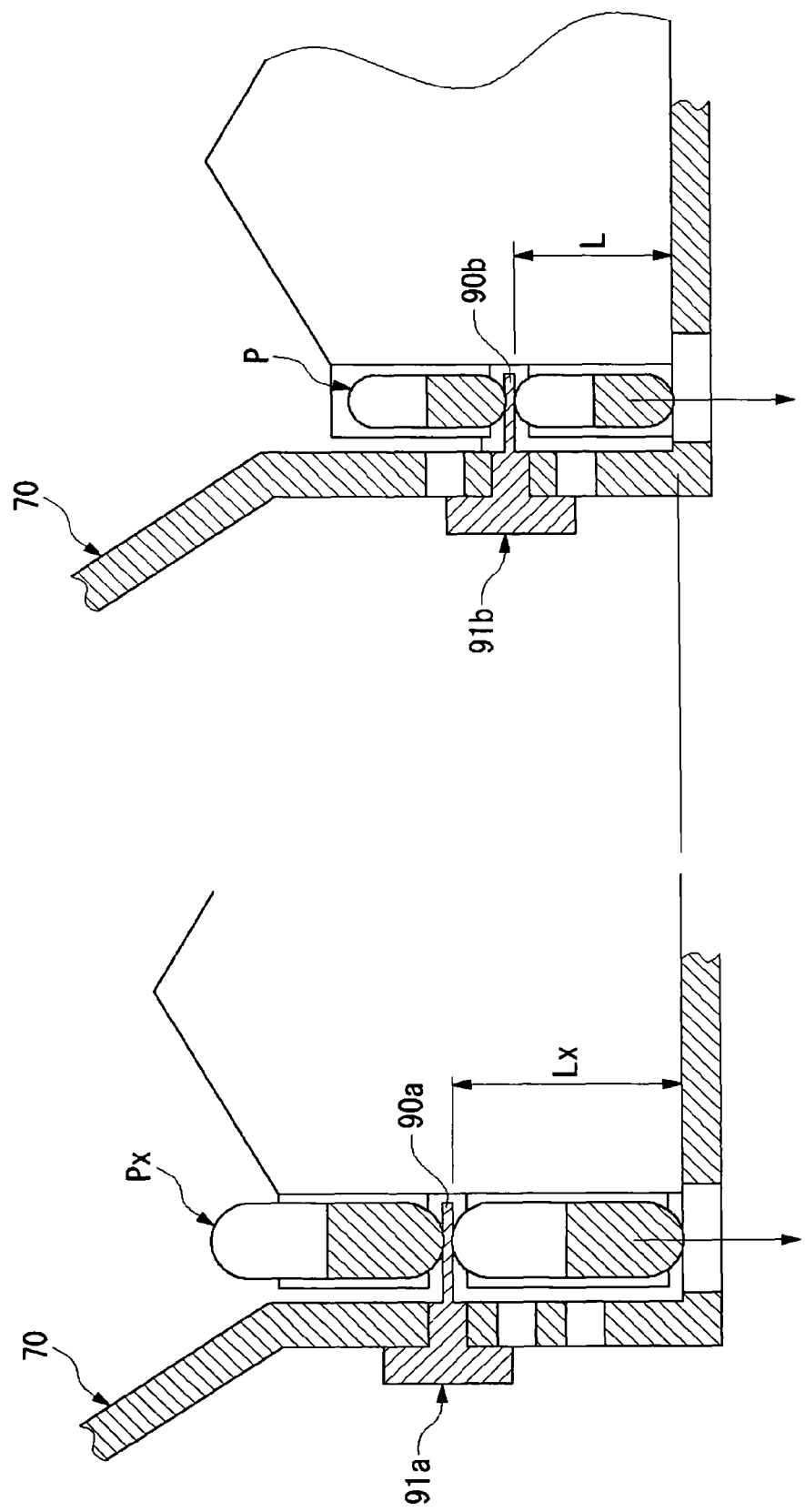
FIG. 9 is a sectional view showing an example of structure for changing the position of a partition in the drug feeder according to the second embodiment.

One possible structure that enables changing the position of the partition plate with a single operation is illustrated in FIG. 9. Parts 91a and 91b that include tongue-like partition plates 90a and 90b, respectively, are formed as parts separate from the container main body 70. The parts 91a and 91b are detachably secured in plug-in holes in the container main body 70. Each of the parts 91a and 91b is inserted from outside of the container main body 70 at a height commensurate with the total length of drug. With this, the partition plate is made to project into a space inside the aligner housing unit. The length of the partition plate may appropriately be determined in accordance with the depth of the gutter (size of the drug in a cross section).

Figure 10A:
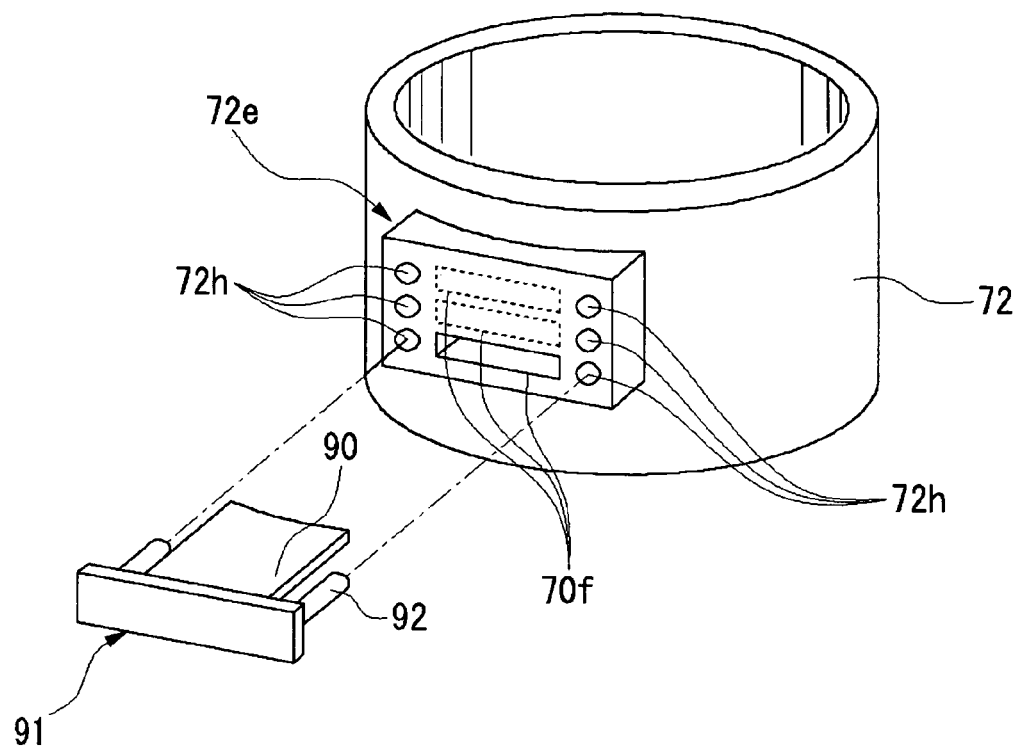
FIG. 10A shows a structure for changing the position of a partition with respect to the container main body.
Figure 11:
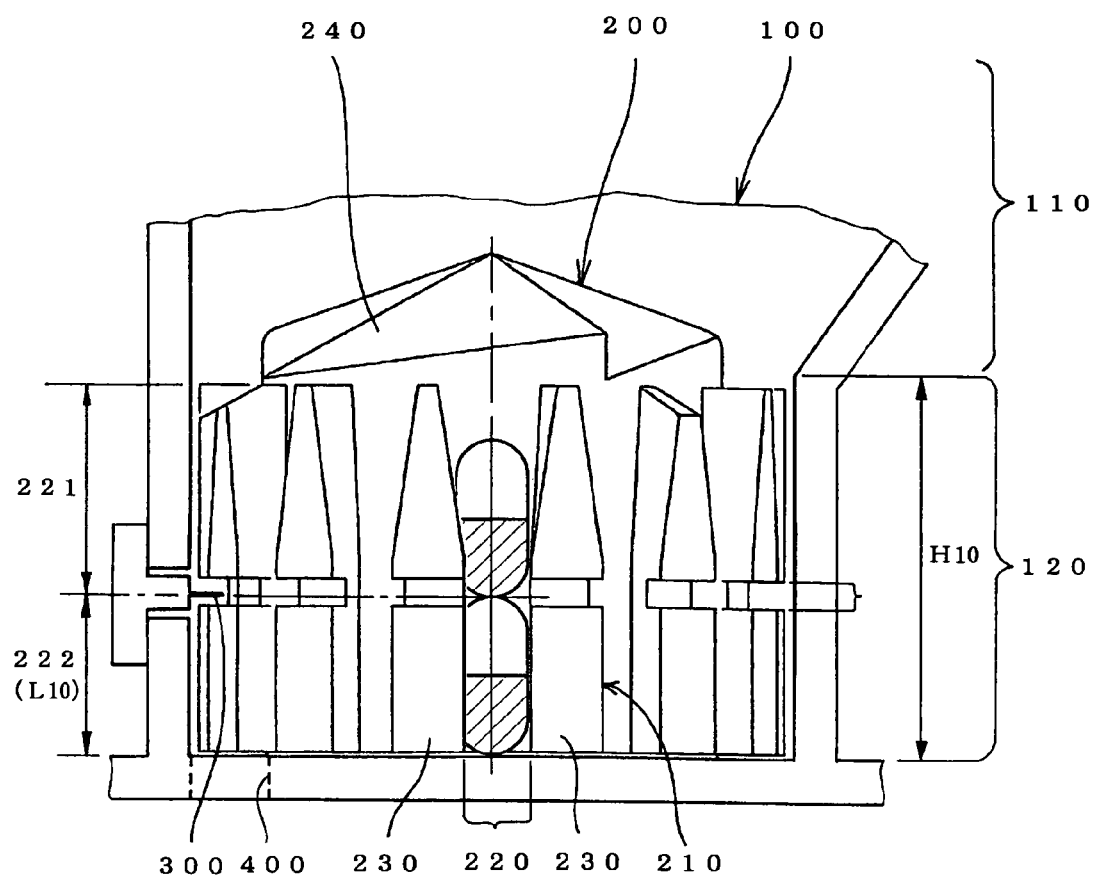
FIG. 11 relates to the second embodiment and shows the structure of the related-art drug feeder.

FIG. 10A schematically shows essential parts of a structure that enables changing the height of the partition plate in a given container main body. Multiple pairs each comprising a plug-in hole 72f and an associated positioning hole 72h are provided at appropriate positions on the outer wall of the aligner housing unit 72 of the container main body (the other portions of the container main body are omitted from illustration). The position of insertion of a partition plate 90 and a positioning pin 92 provided in the part 91 is variable. In this way, the partition plate is easily positioned and the position thereof is easily changed.

In the example shown in FIG. 10A, an assembly 72e that includes the plug-in hole 72f and the positioning hole 72h is also a separate component detachable from the aligner housing unit 72 of the container main body.

In the illustrated example, the plug-in hole 72 is provided at three levels but there is no restriction to the number of levels. Not all of the plug-in holes 72f need remain open. Only those plug-in holes that are necessary may be opened in a casting process, keeping the other holes being blocked.

In the example shown in FIG. 10A, the top and middle plug-in holes are blocked.

Figure 10B:
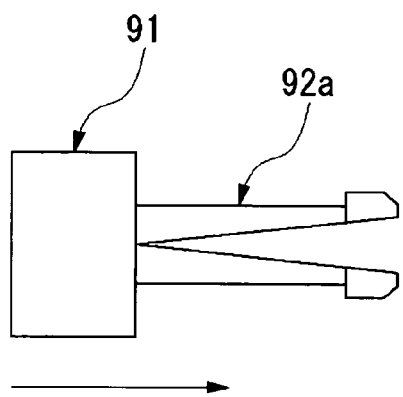
FIG. 10B shows the structure of a positioning pin for positioning the partition plate.

As shown in FIG. 10B, by configuring the positioning pin 92a as a split pin, the pin is secured merely by pressing it in a direction indicated by the arrow with a finger. As such, positioning and detachment are achieved in a single operation without using any tools.

The thickness of the partition plate may be changed depending on the drug type and a material for forming the partition plate may be appropriately selected from materials such as resin and metal (particularly, stainless steel).

For example, in the case of drugs other than capsules, i.e. in the case of drugs such as tablets (uncoated tablets and the like), which are characterized by a disk shape and a uniform thickness, the partition plate should be relatively accurately inserted into a space between two drugs successively introduced into the gutter of the aligner, without encountering any resistance, in order to isolate the two drugs vertically to respectively place them in the preparatory aligning unit and the aligning unit. Accordingly, the partition plate adapted for such a purpose should be light, thin and flexible and should be of high mechanical strength and resistance to fracture. A stainless plate with a thickness of about 0.3 mm-0.5 mm would be favorable for such a purpose.

Usually, capsules are cylindrical and the ends thereof are hemispherical. Therefore, a partition plate with a thickness of about 0.5 mm-1.0 mm can be introduced into a space between drugs relatively easily. Therefore, the partition plate for capsules may be a molded product formed of a resin material such as polypropylene (PP) or flexible polyethylene (PE).

An example will be given below of an assembly of drug feeders adapted for three types of capsules that differ in total length (large-length, medium-length and small-length), the assembly comprising three types of drug feeders (large-length, medium-length and small-length) for feeding respective capsules, and the uniformly-sized container main body being shared by the feeders.

The specification of each of the three types of capsules is as follows.

Large-length capsule (Japanese pharmacopoeia #000): total length=about 22.02 mm, trunk diameter=about 9.53 mm).

Medium-length capsule (Japanese pharmacopoeia #1): total length=about 16.71 mm, trunk diameter=about 6.61 mm).

Small-length capsule (Japanese pharmacopoeia #5): total length=about 9.40 mm, trunk diameter=about 4.66 mm).

The dimensions of the major portions of the aligners fabricated to adapt to the three types of capsules are as follows. (Large-length aligner)

As shown in FIG. 6, a cylindrical ingot member (outer trunk diameter=61 mm) having an agitator unit spirally projecting upward is formed of an acrylonitrile butadiene styrene (ABS) resin. The underside of the ingot member is provided with a hole for connecting with an output rotary shaft of an AC synchronous motor (external driving apparatus).

A total of ten vertical gutters (preparatory aligning unit+ aligning unit) are formed by machining at regular intervals around the entire periphery of the trunk of the ingot member such that a partition wall and a gutter alternate. The gutter width is 10.5 mm and the total length of the gutter is 32 mm. Between the aligning unit and the aligning unit lies a partition gutter with a width of 5 mm crossing the gutter in a circumferential direction.

The specific detail of the total length 32 mm of the gutter as designed is such that the gutter length of the aligning unit that should accommodate the total length of the capsule is about 22 mm and the gutter length of the preparatory aligning unit is 10 mm, the remainder of the total length. Accordingly, when two #000 capsules enter the gutter of the aligner, one of the capsules sticks out from the top end of the gutter by about 12 mm, a situation unique to the embodiment.

[Middle-Length Aligner]

A cylindrical ingot member like that of the large-length aligner is formed. A total of fifteen vertical gutters are formed by machining at regular intervals around the entire periphery of the trunk of the ingot member such that a partition wall and a gutter alternate. The gutter width is 8.0 mm and the total length of the gutter is 32 mm.

The specific detail of the total length 32 mm of the gutter as designed is such that the gutter length of the aligning unit that should accommodate the total length of the capsule is about 17 mm and the gutter length of the preparatory aligning unit is 15 mm, the remainder of the total length. Accordingly, when two #1 capsules enter the gutter of the aligner, one of the capsules sticks out from the top end of the gutter by about 2 mm.

In this embodiment, the preparatory aligning unit and the aligning unit are provided. In the case of Japanese pharmacopoeia #1 capsules, drug feeding performance that presents no real problem is achieved even if the preparatory aligning unit is omitted.

[Small-Length Aligner]

A cylindrical ingot member like that of the large-length aligner is formed. A total of seventeen vertical gutters are formed by machining at regular intervals around the entire periphery of the trunk of the ingot member such that a partition wall and a gutter alternate. The gutter width is 6.0 mm and the total length of the gutter is 32 mm.

The specific detail of the total length of the gutter as designed is such that the gutter length of the aligning unit that should accommodate the total length of the capsule is about 10 mm and the gutter length of the preparatory aligning unit is 22 mm, the remainder of the total length. Accordingly, three #5 capsules can enter the gutter of the aligner and the top end of one of the capsules is receded from the top end of the gutter by about 2 mm.

In this embodiment, the total length of the gutter is set at 32 mm and the preparatory aligning unit and the aligning unit are provided. The dimensions are such that #5 three capsules can successively enter the aligner. In the case of small-sized, lightweight drugs such as #5 capsules, drug feeding performance that presents no problem in actual use is often achieved even when the preparatory aligning unit is omitted.

[Container Main Body]

The container main body is formed of an acrylonitrile styrene (AS) resin. The configuration and dimensions of the container main body are adapted to the large-length aligner.

The space inside the aligner housing unit is designed as a cylinder with an inner diameter $\phi$ of 62 mm so as to ensure that the aligner is rotatable and appropriate gap is secured between the aligner housing unit and the aligner. The height of the aligner housing unit is designed to be 32 mm to adapt to the large-length aligner. As shown in FIG. 6, the container main body is designed such that the partition plate is inserted straight above the drug outlet from outside the container, at a height commensurate with the total length of the drug from the underside of the aligner. In this way, the gutter of the aligner is separable into the aligning unit and the preparatory aligning unit. The underside of the aligner serves as a reference to measure the dimensions of the aligner. As shown in FIGS. 9 and 10, the structure including the positioning pin and the positioning hole is attached to the outside of the aligner housing unit so that the position of the partition plate member can be changed in a single operation to adapt to the total length of the capsule.

The cell unit above the aligner housing unit and a seat unit below are integrally formed with the container main body. A detailed description of the configuration and dimensions of the cell unit and the seat unit as well as other minor details will be omitted.

The container main body as described above, provided with the aligner housing unit adapted to the large-length aligner, is also formed in drug feeders for the other drug types.

Three types of drug feeders are built by combining the uniformly-sized container main body with the large-length aligner, the medium-length aligner and the small-length aligner. The partition plate is set at appropriate positions and the external driving apparatus is fitted to the underside of the drug feeder.

Observation of the function of the preparatory aligning unit and drug feeding performance, made while the cell unit of the drug feeder is being filled with associated capsules and the external driving apparatus is being operated, revealed that the preparatory aligning unit of the large-length drug feeder, with a gutter length shorter than the total length of the drug by 12 mm, functioned properly by successfully guiding the capsules. The capsules entering the preparatory aligning unit fall into the aligning unit without being stuck at the entrance of the gutter. Situations such as failure of drugs to be ejected out of the drug feeder did not occur at all in an experiment in which one thousand drugs are successively fed.

In drug feeders for medium-length drugs and for small-length drugs, it is ensured that the top end of the aligner housing unit of the container main body and the top end of the preparatory aligning unit are at practically the same height. It is also found that these drug feeders are not significantly inferior in its capacity to accommodate drugs in comparison with feeders with a short-sized aligner housing unit adapted to the aligner provided only with the aligning unit to accommodate small-length drugs (note that a short-sized aligner housing unit creates an accordingly larger cell unit).

An advantage of the second embodiment is that the container main body is made more compact in height than in the related art. Further, the second embodiment allows the use of a uniformly-sized container main body to build an assembly of drug feeders even if drugs may vary in total length. Accordingly, the cost of fabricating a drug packing apparatus is reduced.

Third Embodiment

The third embodiment relates to an automatic drug dispenser for accommodating various drugs and automatically ejecting a desired drug for purposes including packing, in accordance with a prescription or an instruction for dispensing and, more particularly, to an automatic drug dispenser in which it is checked if a drug cassette that ejectably stores a drug matches a base unit when the cassette is attached to or detached from the base unit.

The third embodiment also relates to drug feeders built in the automatic drug dispenser.

Figure 22:
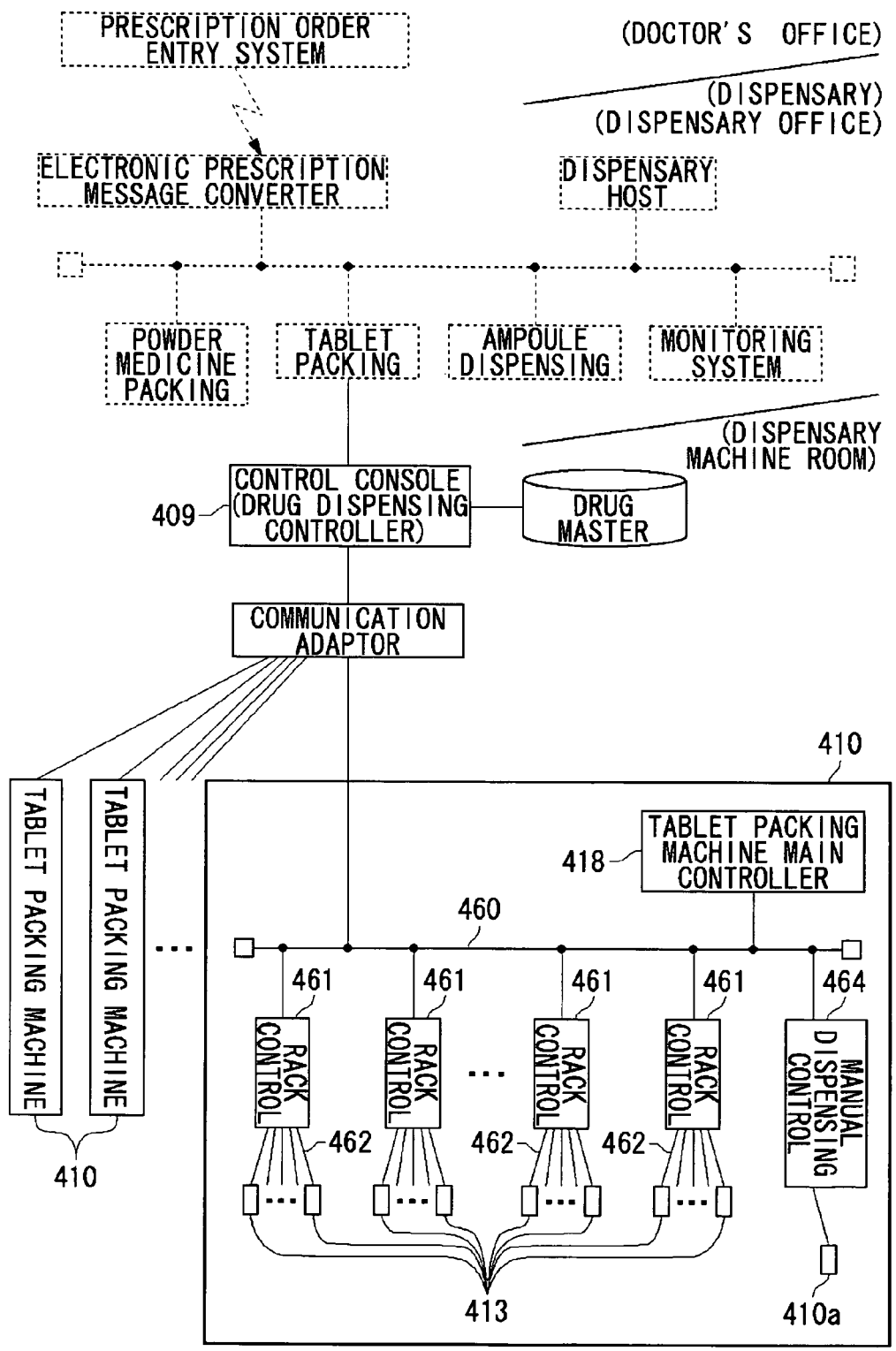
FIG. 22 is a block diagram showing the overall structure of the control system of the automatic drug dispenser.

First, a tablet packing machine 410, a typical embodiment of the inventive automatic drug dispenser, will be described. FIGS. 21A-21F show a mechanical structure of the tablet packing machine 410 and a large number of drug feeders 413 built in the machine. FIG. 21A is a perspective view showing the appearance of the tablet packing machine 410; FIG. 21B is a schematic view showing the internal structure of the tablet packing machine 410; FIG. 21C is a left side view of the drug feeder 413; FIG. 21D is a front view of the drug feeder; FIG. 21E is a longitudinal sectional view showing the left side of the drug feeder; FIG. 21F is a control block diagram related to active components of the drug feeder 413. FIG. 22 is a block diagram showing the overall structure of the control system of the automatic drug dispenser; and FIGS. 23A and 23B show the structure of control data. FIG. 23A shows the structure of a record in a drug master table; and FIG. 23B shows the structure of an electronic message for an instruction for ejecting drugs.

The tablet packing machine 410 (see FIGS. 21A and 21B) comprises: a large number of drug feeders 413 accommodating various drugs 1 (disk-shaped drugs, ball-shaped drugs, capsules, cylinder-shaped drugs, tablets and the like) according to their categories; drug collecting mechanisms 414 and 415 for collecting drugs 1 ejected from the drug feeders 13; a packaging apparatus 417 for packing the drugs 1 received from the drug collecting mechanisms 414 and 415; and a controller 418 (tablet packing machine main controller, main control apparatus of the packing machine main body) embodied by a microprocessor system or the like. Under the control of the controller 418, a desired number of drugs 1 are ejected from the associated drug feeders 413 in accordance with prescription data or drug dispensing instruction data derived therefrom. The drug collecting mechanisms 414 and 415 collect the drugs 1 thus ejected and feed the drugs 1 to a drug input unit 416 (collected drug input inlet) provided downstream so that the drugs 1 are packed in the packaging apparatus 417. The drugs 1 are packed in packing strip 2 (packing paper) as they are compartmentalized according to a unit to be taken at a time or a unit to be administered at a time.

More particularly, the tablet packing machine 410 houses a drug storage 411 (a drug rack unit and a drug container storage) at the upper end of the machine and houses the packaging apparatus 417 at the lower end thereof. Conduit pipes 414 (ducts, chutes, guide passages, upper drug collecting channels) and collecting members 415 (hopper-like members, funnelform members, lower drug collecting channels) constituting the drug collecting mechanism communicate between the drug storage 411 and the packaging apparatus 417. In the drug storage 411, multiple individually slidable drug feeder storages 412 (drug storages) are arranged horizontally. In each of the drug feeder storages 412, several to several tens of detachable drug feeders 413 are arranged vertically and horizontally. The storage position or the feeder storage address of each of the drug feeders 413 in the drug storage 411 is determined by a triplet comprising a column address, a row address and a board address. A column address indicates a position in the horizontal direction. More specifically, it indicates the ID number of the drug feeder storage 412. A row address indicates a position in the vertical direction. More specifically, it indicates the ID number of a rack board to which the drug feeder 413 is mounted. A board address indicates a position in the front-back direction or depth direction. More specifically, it indicates the order of the drug feeder 413 in the rack board. In a case where the drug feeders 413 are in a cylindrical arrangement (not shown), a feeder storage address is similarly determined if the ID number of the drug feeder storage 412 is unique.

Each drug feeder 413 (see FIGS. 21C-21E) is generally partitioned into a drug cassette 420 ejectably accommodating a large number of drugs 1, and a base unit 430 for detachably supporting the drug cassette 420 and driving a motor to eject drugs. The drug feeder 413 is designed to eject a designated number of drugs 1. Components built in the base unit 430 (see FIG. 21F) include a motor 413j provided as an actuator, an ejection sensor 433 provided as a means for detecting ejected drugs falling and an attachment/detachment sensor 434 provided as a means for detecting the attachment and detachment of a cassette. These components are connected to a rack control circuit 461 via individual intra-rack wirings 462 and are permanently fixed to the rack of the drug feeder storage 412. In contrast, the drug cassette 420 of the drug feeder 413 is detachable to facilitate refilling of the cassette with drugs.

Also built in the tablet packing machine 410 (see FIGS. 21A and 21B) are a manual dispensing unit 410a formed to be extractable from the housing in the forward direction and a manual drug dispensing apparatus provided with an actuating member (not shown) located in the housing to receive drugs from the manual dispensing unit 410a. Multiple vertically and horizontally arranged compartments are formed in the manual dispensing unit 410a. As such, the manual dispensing unit 410a is suitably used to manually dispense drugs per day multiple times, by compartmentalizing drugs so that each compartment contains drugs to be taken per day or each compartment contains drugs to be taken at each of different occasions in a day throughout a period in which drugs should be taken. The manual dispensing unit 410a is used to pack drugs not allocated to the drug feeders 413 together with the drugs allocated to the drug feeders 413. For example, intermittent driving of a conveyor inside the manual dispensing unit 410a sequentially ejects manually dispensed drugs (see, for example patent document No. 6).

A control console 409 (drug dispensing controller) is attached to the tablet packing machine 410 or provided as close as possible to it (see FIG. 21A) in order to integrally manage the automatic dispensing operation of the tablet packing machine 410. If the tablet packing machine 410 is a stand-alone, minimum system, the control console 409 and the tablet packing machine 410 are often integrally built. If the tablet packing machine 410 is a medium to large scale system comprising multiple machines, the control consol 409 manages multiple tablet packing machines 410; i.e. one-to-many or few-to-many management system is employed. Therefore, the control console 409 is often provided as an isolated, independent unit (see FIG. 22). In a stand-alone system in which the automatic drug dispenser is used in an isolated fashion, prescription data, prepared by converting the contents of prescription into electronic data, and drug dispensing data derived from the prescription data are input to the control console 409 via an input device (not shown). In a network-based system in which the control console 409 is connected to a prescription order entry system of a doctor's office or a host computer of a dispensary (see dotted lines in FIG. 22), prescription data prepared in the prescription order entry system, for example, are subject to data format conversion by an electronic prescription message converter in the middle of the network and are subject to data analysis by a dispensary host computer so as to be converted into drug dispensing data comprising data fit for automatic drug dispensing. Only the data related to the tablet packing machine 410 under the control of the control console 409 are forwarded to the control console 409.

For the purpose of preparing a drug ejection instruction on the basis of the prescription data or drug dispensing data derived therefrom, the control console 409 (see FIG. 22) comprises a computer storing a drug master table. For example, the control console 409 may comprise a laptop personal computer or a desktop personal computer. The control console 409 broadcasts the drug ejection instruction prepared in an electronic message format to the tablet packing machines 410 via a suitable communication adapter. The drug master table (see FIG. 23A) comprises a large number of records searchable using drug codes as primary keys. Each record includes drug information such as drug name and dosage form. The drug master table also includes items such as: "machine ID" for identifying the tablet packing machine 410; "check data" assigned to each base unit 430 and checked against cassette identification information attached to the drug cassette 420; "feeder storage address" described above comprising a column address, a row address and a board address; and "cassette state" indicating whether the cassette is attached and whether the cassette is operable. A free area for future expansion that remains cleared to zero and unused for future expansion of functions is reserved.

In order to cause the associated drug feeder 413 to eject associated drugs, an electronic message for a drug ejection instruction transmitted from the control console 409 to the tablet packing machine 410 (see FIG. 23B) includes the number of drugs designated by a prescription. the machine ID that identifies the tablet packing machine 410 (identified by one of integers 1-N) and the aforementioned feeder storage address (a drug feeder storage address related to the drug feeder storage) that identifies the drug feeder 413 in the tablet packing machine 410 are also included in the electronic message to designate the destination of the message.

For reception of the drug ejection instruction, an internal communication means 460 of the tablet packing machine 410 is extended outside so as to be connected to a communication adapter of the control console 409 (see FIG. 22). For example, the internal communication means 460 is a LAN conforming to the IEEE RS485 standard. The controller 418 is connected to the LAN. Also connected to the LAN via the intra-rack wiring 462 are the rack control circuit 461, which controls the drug feeders 413, and a manual dispensing control circuit 464, which controls the operation of the manual dispensing unit 410a. The rack control circuit 461 is provided for each rack inside the drug storage 411. Therefore, there are multiple rack control circuits 461 in each tablet packing machine 410.

A summary of the third embodiment will be given.

(1) An automatic dispenser according to the third embodiment comprises: a drug cassette which ejectably accommodates drugs; a base unit which detachably supports the drug cassette and drives a motor to eject drugs; a drug feeder storage which accommodates a large number of base units; a reading device which is provided in each of the base units and reads identification information assigned to the drug cassette; and a checking means which compares a result of reading with pre-stored check data, wherein a set of a microprocessor and a memory, or a microprocessor with a built-in memory is mounted in each of the base units, the checking means and the check data are built in each microprocessor in a distributed manner, and wherein a check bypassing means which temporarily suspends the checking function of the checking means is built in all or some of the microprocessors.

A drug feeder according to the third embodiment may comprise: a drug cassette which ejectably accommodates drugs; a base unit which detachably supports the drug cassette and drives a motor to eject the drugs, wherein a reading device which reads identification information assigned to the drug cassette is provided in the base unit, a set of a microprocessor and a memory, or a microprocessor with a built-in memory is mounted in the base unit, wherein a checking means which compares check data stored in the memory with a result of reading by the reading device is built in the microprocessor, and wherein a check bypassing means which temporarily suspends checking function is built in the microprocessor.

(2) The automatic drug dispenser of (1) according to the third embodiment may further be characterized in that an overwriting means which overwrites the check data with the identification information read by the reading device is built in all or some of the microprocessors.

(3) The automatic drug dispenser of (2) according to the third embodiment may further be characterized in that the base units are classified in a first group comprising a relatively large number of base units and a second group comprising a relatively smaller number of base units. The microprocessor mounted in the base unit of the first group activates the check bypassing means instead of activating the overwriting means. The microprocessor mounted in the base unit of the second group activates the overwriting means instead of activating the check bypassing means.

(4) The drug feeder of (1) and the automatic drug dispenser of (1) through (3) according to the third embodiment may be characterized in that the check bypassing means includes a means for saving the check data and a means for restoring the check data. Alternatively, the check bypassing means may include a means for updating a flag for switching between different operations of the check bypassing means.

(1) In the drug feeder and automatic drug dispenser of (1), distributed microprocessor arrangement not only enables the base unit of each drug feeder to execute the checking function but also is functionally expanded to process the temporary suspension of checking function. Accordingly, the base unit of each drug feeder is capable of the processing temporary suspension of the checking function as well as executing the checking function.

Thus, the above embodiment realizes a drug feeder and an automatic drug dispenser in which it is possible to test replacement of drug cassettes in a drug feeder in which a trouble occurs, without requiring rewriting of a drug master table.

In the automatic drug dispenser of (2), the check data is overwritten with the identification information read by the reading device from the drug cassette, by activating the overwriting means. By including provisions to set check data in a state in which the drug cassette and the corresponding base unit are combined, preparation of check data is facilitated. Since the provisions are implemented by distributed microprocessor arrangement. Therefore, replacement of the drug cassette to be attached to the base unit is conducted without requiring rewriting of the drug master table. That is, replacement of the drug cassette to be attached to the base unit, i.e. updating of the correspondence between the base unit and the drug cassette, is performed easily and accurately (hereinafter, such a feature will be referred to as interchangeability).

In the automatic drug dispenser of (3), the check data overwriting means or the check bypassing means may be selected for use depending on the grouping of the drug feeder.

In the related-art tablet packing machine, the manual dispensing unit already described is used to automatically pack drugs not accommodated in the drug storage. The manual dispensing operation should best be avoided as it is cumbersome and time-consuming. In one approach to reduce the frequency of manual dispensing operations, several drug cassettes for respective drug types may be prepared outside the drug storage so as to accommodate drugs which would have been dispensed manually in the related art. Such a drug cassette may be attached to the base unit of the tablet packing machine as the need arises to replace the existing drug cassette. Unlike the drug cassette (drug feeder) described above characterized by frequent use, such a drug cassette (drug feeder) is characterized by higher frequency of replacement at the base unit than the frequency of use. Therefore, interchangeability is given top priority.

In introducing the check data overwriting means and check bypassing means in the automatic drug dispenser of this type, the drug feeders are classified in two groups. A relatively large number of drug feeders in which safety is a top priority are classified in a first group. A smaller number of drug feeders in which interchangeability is a top priority are classified in a second group. The check data overwriting means, which enhances interchangeability, is built in the drug feeders belonging to the second group. The check bypassing means is built in the drug feeders belonging to the first group so that replacement or the like can be tested without detracting from safety. With this, safety and interchangeability based on drug cassette matching are achieved in a compatible manner.

In the drug feeder and automatic drug dispenser of (4), the check bypassing means is simply implemented by a combination of the saving means and the restoring means or a flag updating means.

Specific embodiments of the drug feeder and automatic dispenser of the third embodiment will be described below by explaining the third embodiment-1 and the third embodiment-2.

Figure 19:
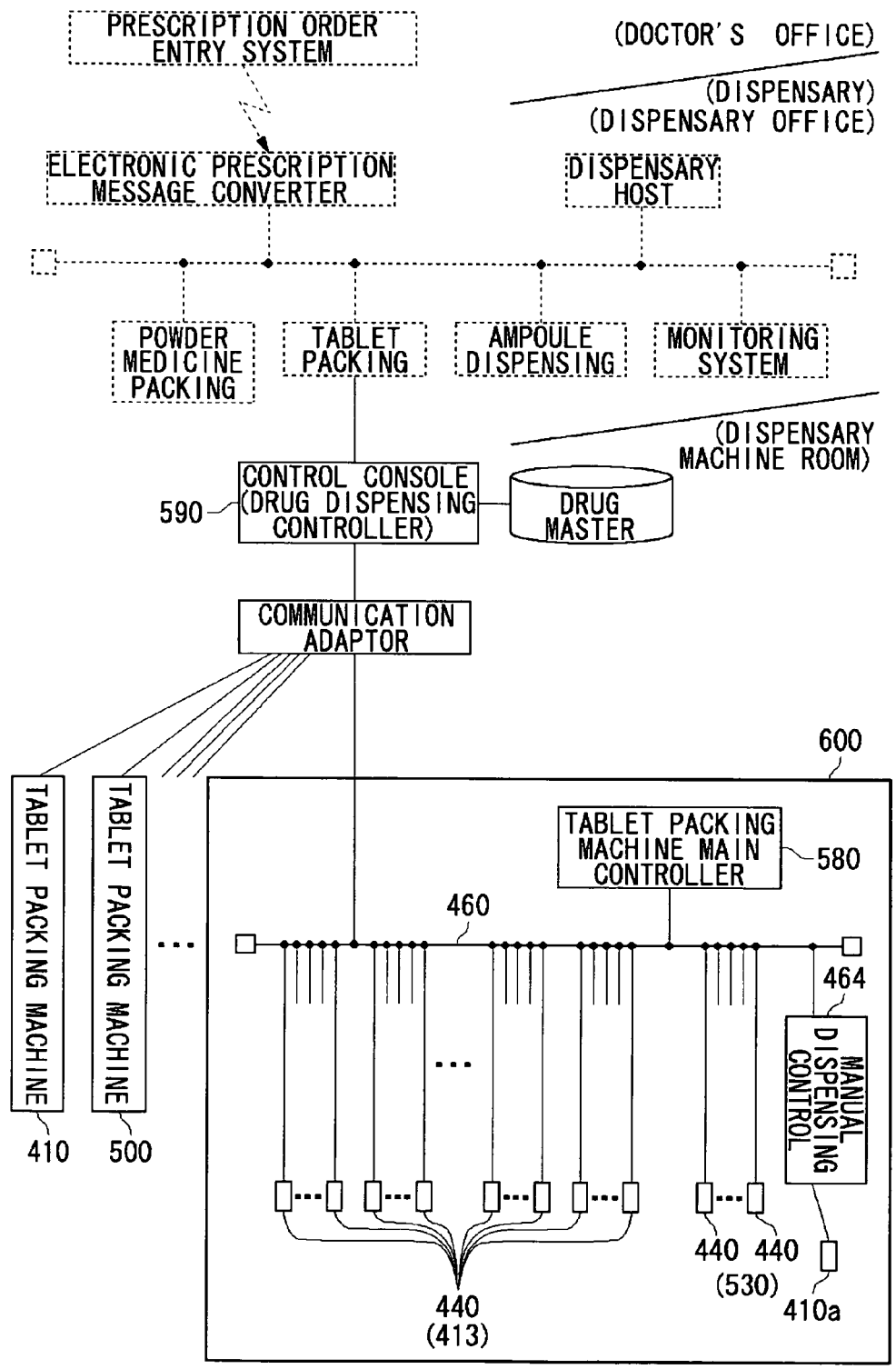
FIG. 19 is a block diagram showing the overall structure of a control system according to third embodiment-2.
Figure 20A:
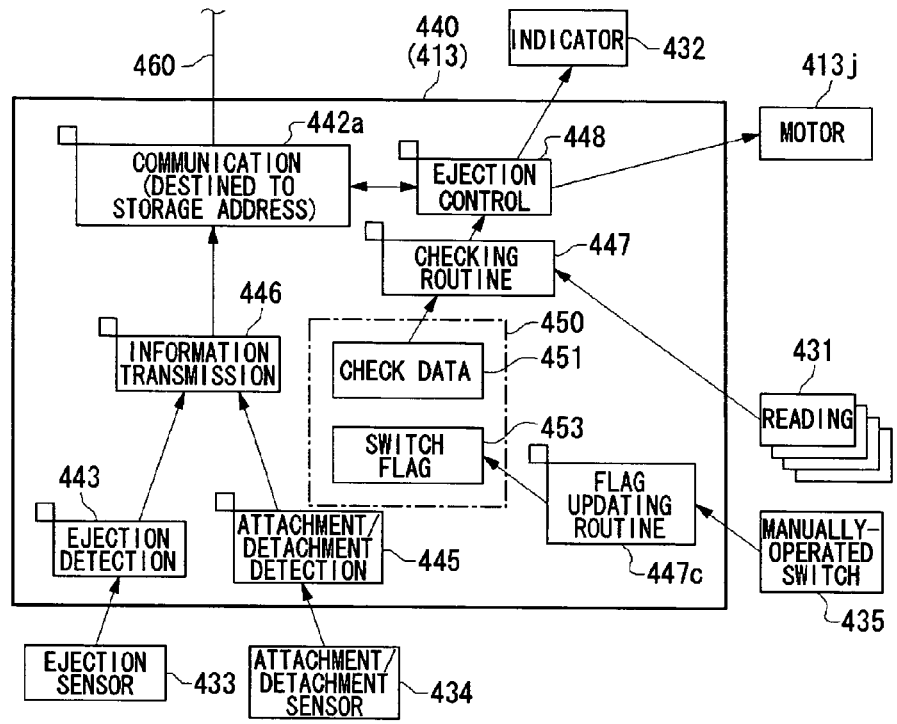
FIG. 20A is a functional block diagram of the microprocessor of the first group.
Figure 20B:
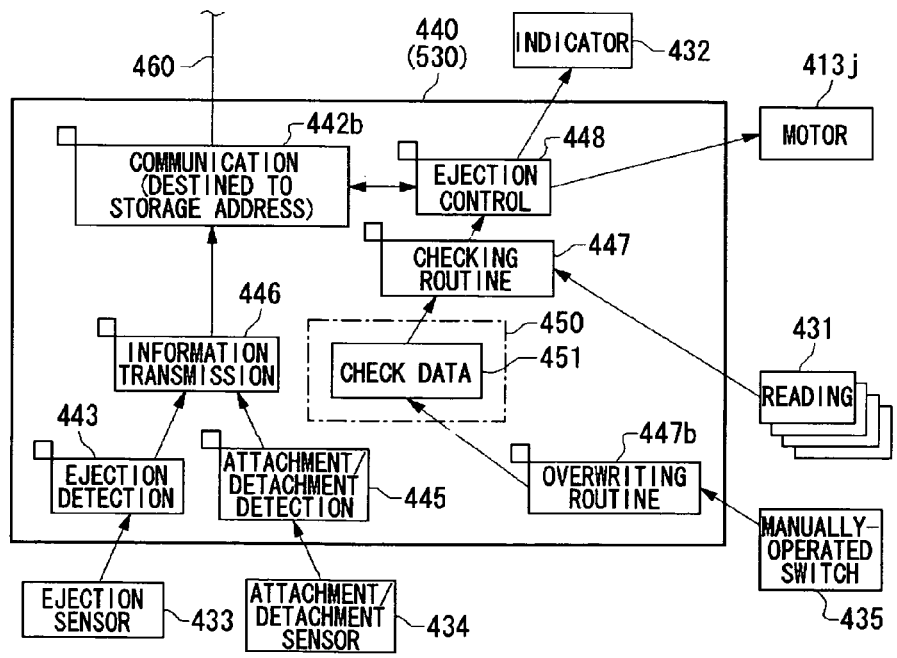
FIG. 20B is a functional block diagram of the microprocessor of the second group.

The third embodiment-1 shown in FIGS. 12 through 18G is an embodiment of all the features (1) through (4) above. The third embodiment-2 shown in FIGS. 19-20B is a variation thereof.

For brevity, fastening members such as bolts, joint members such as hinges, passage opening/closing members such as shutters, detailed circuit features such as motor drivers are omitted from the illustration. Those elements that are required in the invention and elements related thereto are mainly illustrated. Those constituting elements that are similar to the corresponding elements in the related art are designated by the same reference numerals. The following description mainly concerns a difference from the related art.

Third Embodiment-1

Figure 13A:
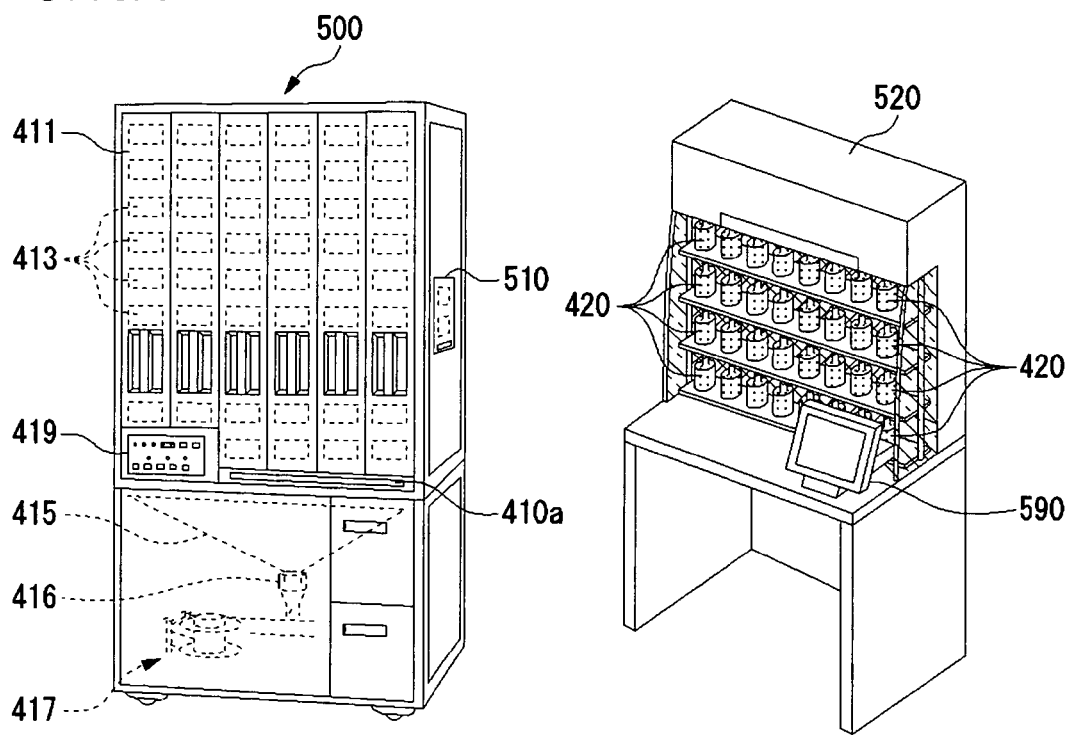
FIG. 13A is a perspective view of an automatic drug dispenser according to a third embodiment of the present invention.
Figure 13B:
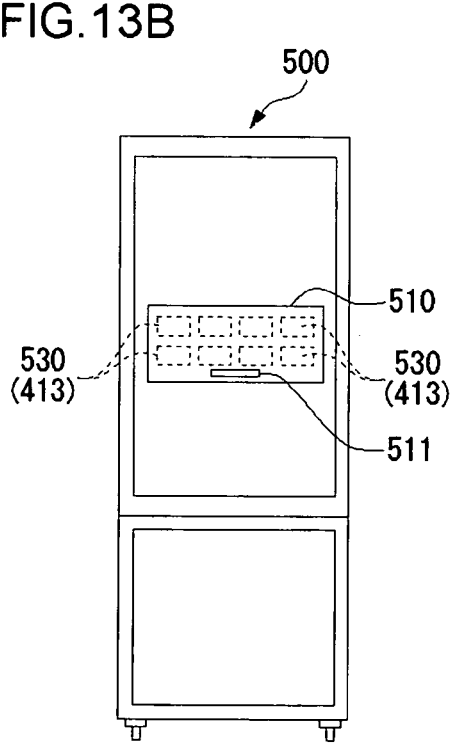
FIG. 13B is a right side view of a tablet packing machine according to the third embodiment.
Figure 13C:
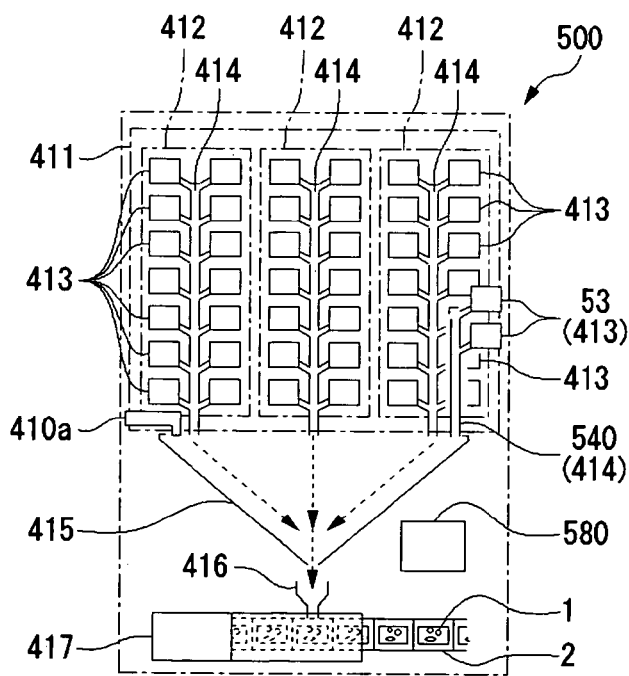
FIG. 13C is a schematic view showing the internal structure of the tablet packing machine according to the third embodiment.
Figure 14A:
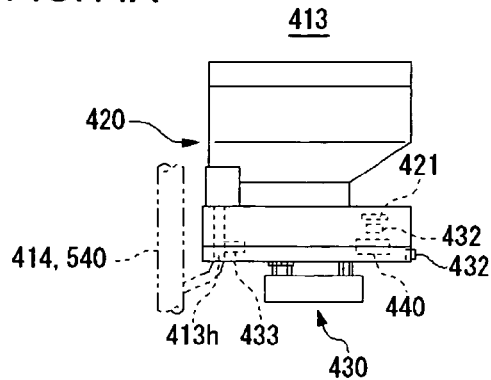
FIG. 14A is a left side view of a drug feeder according to the third embodiment.
Figure 14B:
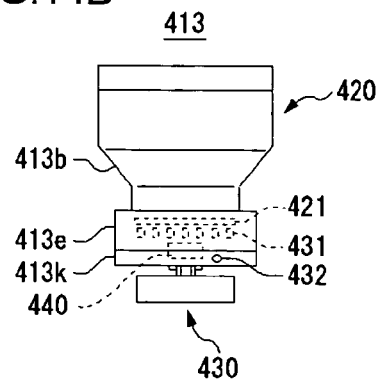
FIG. 14B is a front view of the drug feeder according to the third embodiment.
Figure 14C:
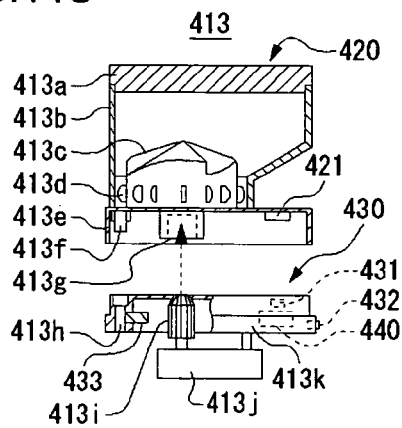
FIG. 14C is a longitudinal sectional view showing the left side of the drug feeder according to the third embodiment.
Figure 14D:
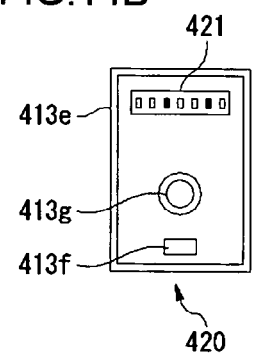
FIG. 14D is a bottom view of a drug cassette according to the third embodiment.
Figure 14E:
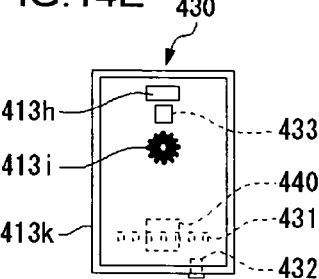
FIG. 14E is a top view of a base unit according to the third embodiment.
Figure 14F:
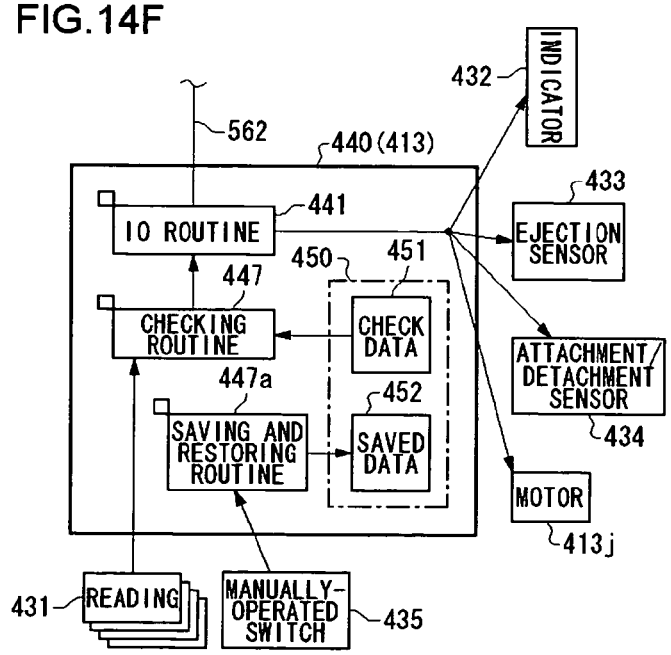
FIG. 14F is a functional block diagram of a microprocessor provided in each of a large number base units belonging to a first group.
Figure 14G:
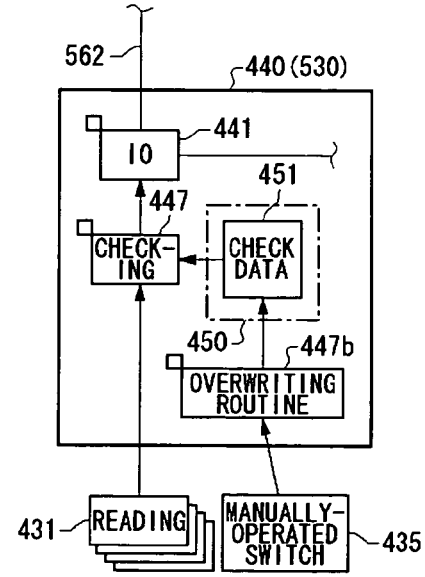
FIG. 14G is a functional block diagram of a microprocessor provided in a smaller number of base units belonging to a second group.

A description will now be given of the specific structure of the drug feeder and automatic drug dispenser according to the third embodiment-1 with reference to the drawings. FIGS. 13A-13C show the overall mechanical structure of the automatic drug dispenser. FIG. 13A is a perspective view; FIG. 13B is a right side view of a tablet packing machine 500; and FIG. 13C shows the internal structure of the tablet packing machine 500. FIGS. 14A-14G show the structure of each of a large number of drug feeders 413 and 530 built in the tablet packing machine 500. FIG. 14A is a left side view of the drug feeder; FIG. 14B is a front view of the drug feeder; FIG. 14C is a longitudinal sectional view showing the left side of the drug feeder; FIG. 14D is a bottom view of the drug cassette 420; FIG. 14E is a top view of the base unit 430; FIGS. 14F and 14G are block diagrams showing the primary functions of a microprocessor 440 provided in each of the base units 430 in a distributed fashion.

Figure 15:
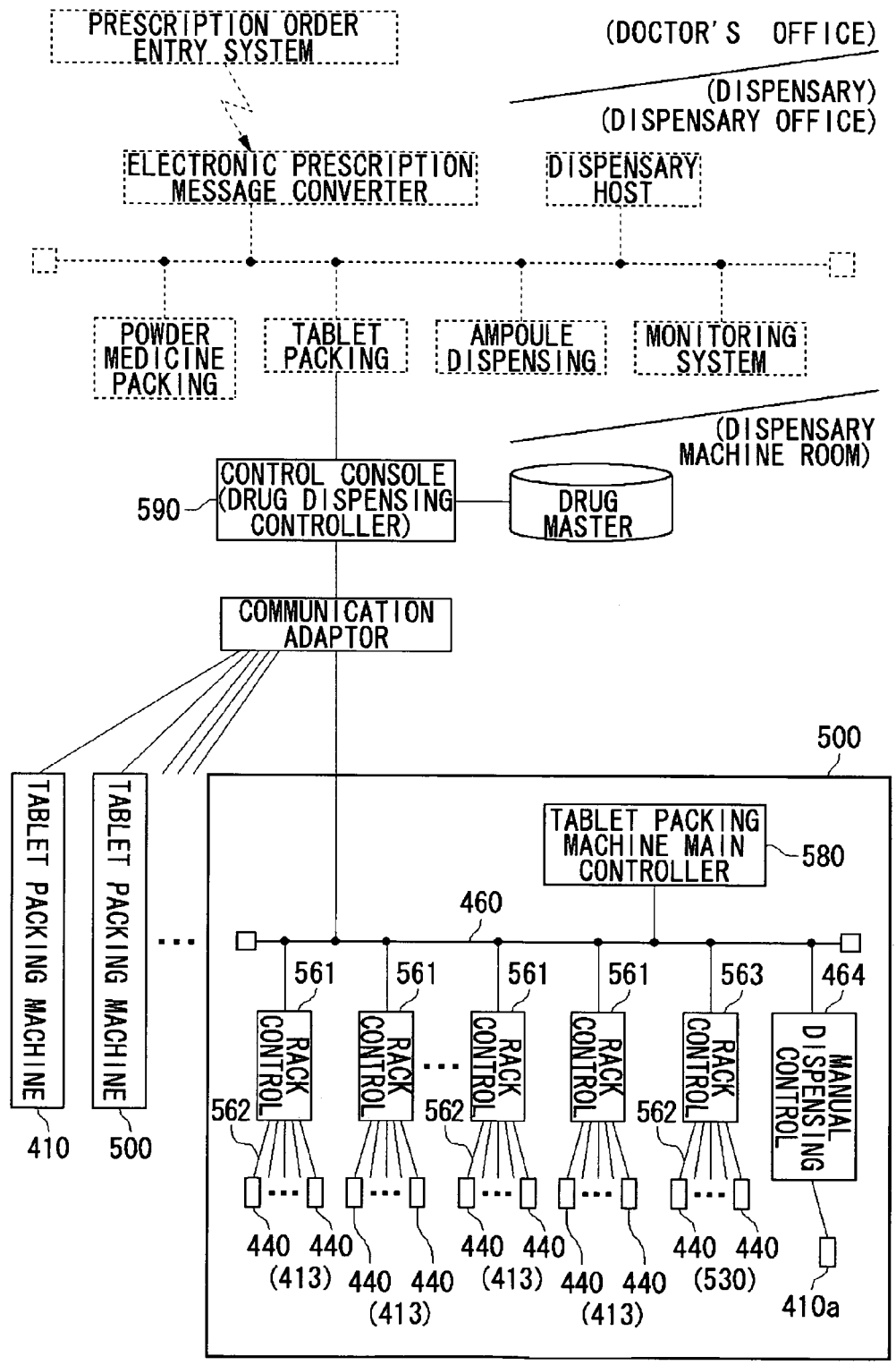
FIG. 15 is a block diagram showing the overall structure of the control system of the automatic drug dispenser.
Figure 17:
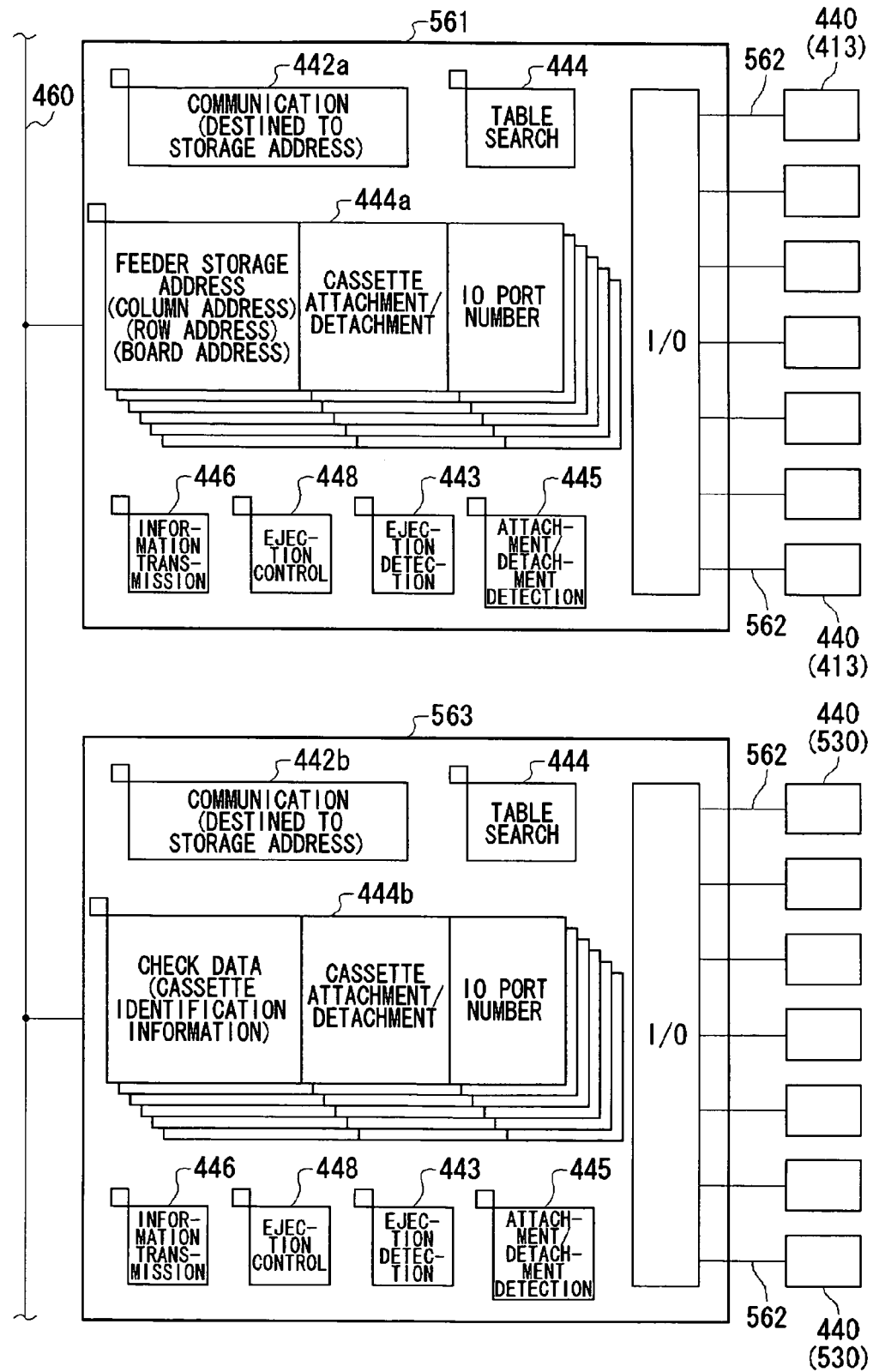
FIG. 17 is a functional block diagram of a tablet packing machine sub-controller in a control system.

More specifically, FIG. 14F is a functional block diagram of the microprocessor provided in each of a large number base units 430 belonging to the first group (i.e. the base unit 430 of the drug feeder 413 in the drug storage 411). FIG. 14G is a functional block diagram of the microprocessor 440 provided in each of a smaller number of base units 430 belonging to the second group (i.e. the base unit 430 of the drug feeder 530 in a feeder storage with cassette interchangeability 510). FIG. 15 is a block diagram showing the overall structure of the control system of the automatic drug dispenser; and FIGS. 16A through 16C show the structure of control data. FIG. 16A shows the structure of a record in a drug master table; and FIGS. 16B and 16C show the structure of an electronic message for an instruction for ejecting drugs. FIG. 16B shows an instruction addressed to the first group and includes the drug feeder storage address. FIG. 16C shows an instruction addressed to the second group and includes the check data. FIG. 17 is a functional block diagram of rack control circuits 561 and 563 (tablet packing machine sub-controller) in the control system.

Differences between the automatic drug dispenser of the third embodiment-1 and other automatic drug dispensers are that: a feeder storage with cassette interchangeability 510 and a stock rack 520 are added in the tablet packing machine 500, that the microprocessor 440 is mounted in the base unit 430 of each drug feeder 413, that the checking means and the check data are built in each microprocessor 440 in a distributed manner, and that a control console 590 (drug dispensing controller) is partially expanded in its functions to adapt to the grouping of the base units 430 of the drug feeders 413. In association with these features, the rack control circuit 461 is partially remodeled, resulting in the rack control circuit 561. Further, a new rack control circuit 563 is introduced. The controller 418 is partially remodeled so as to adapt to the grouping, resulting in a controller 580.

Features that are introduced in the tablet packing machine 500 will be described with reference to FIGS. 13A-13C. The feeder storage with cassette interchangeability 510 is built in an window opening formed on the right side of the drug storage 411. Normally, the opening is closed by a transparent door. As a user grips a door handle 511 to lift the transparent door, the opening is exposed so that the drug cassette 420 is introduced into or retrieved from the feeder storage with cassette interchangeability 510. The drug feeder storage 412 stores as many as several hundred drug feeders 413. In contrast, the feeder storage with cassette interchangeability 510 stores a smaller number of (for example, several tens of) drug feeders 530. The base unit 430 of each of a relatively large number of drug feeders 413 mounted in the drug feeder storage 412 is classified in the first group. The base unit 430 of each of a relatively smaller number of drug feeders 530 mounted in the feeder storage with cassette interchangeability 510 is classified in the second group.

The mechanical structure and basic function of the drug feeder 530 are the same as those of the drug feeder 413. Therefore, the drug feeder will be generically referred to using a reference numeral "413" where distinction is not necessary. Where distinction is necessary, reference numerals "413" and "530" will be used. The drug feeder 530 is provided with the drug cassette 420 which ejectably accommodates drugs and the base unit 430 which detachably supports the drug cassette 420 and drives a motor to eject the drugs. In accordance with an instruction for ejecting drugs from the control console 590, a designated number of drugs 1 are ejected from the drug cassette 420 so that the ejected drugs fall to the collecting member 415 via a conduit pipe 540 similar to the conduit pipe 414. A difference between the drug feeder 413 and the drug feeder 530 consists in an additional program related to the checking function, as described later.

The stock rack 520 is a simple rack separate from the tablet packing machine 500 and is capable of stocking a large number of (for example, several tens to several hundreds of) drug cassettes 420. The drug cassettes 420 are attached for use to the base unit 430 mounted in the feeder storage with cassette interchangeability 510. The drug cassettes 420 stocked in the stock rack 520 belong to the second group in the sense that they constitute the drug feeders 530 of the second group as they are mounted in the base unit 430. When removed from the base unit 430, the drug cassettes 420 are stocked in the stock rack 520 and are reserved for use. For this reason, the number of drug cassettes 420 in the second group is larger than the number of base units 430 if the stock rack 520 is taken into consideration in addition to the feeder storage with cassette interchangeability 510. In contrast, in the first group, the number of drug cassettes 420 accommodated in the drug storage 411 is equal to or smaller than the number of base units 430. The stock rack 520 may or may not serve as a workbench or a table on which to place the control console 590. The stock rack 520 may be provided in one-to-one relationship with the tablet packing machine 500. Alternatively, a smaller number of or a larger number of it may be provided than the number of tablet packing machines 500.

The drug feeders 413 and 530 each comprises the drug cassette 420, which is detachable, and the base unit 430, which is fixed (see FIGS. 14A through 14G). A detailed description of these components will be given, duplicating the description already given as necessary.

The drug cassette 420 is configured such that a container unit 413b with a lid 413a (a cup, a drug containing unit, a drug container) and an aligner 413c (a rotor, an aligning member, an ejection member), which has partition walls 413d (molded blades, blade-like projections, aligning members) provided at the circumference of the board, are secured to a casing board 413e (joint unit for attachment and detachment). When the aligner 413c is rotated via a cylindrical unit 413g (detachable power transmitting member), the drugs 1 inside the container unit 413b enter a space between the partition walls 413d one after another so as to be aligned. The drugs 1 then fall down one by one through an ejection outlet 413f.

The base unit 430 is provided with a base 413k (basic securing member) fitted to the drug feeder storage 412, a motor 413j (actuator) fixed to the base 13k, a spline shaft 413i (detachable power transmitting member) joined to the rotating shaft of the motor 413j. In order to facilitate the attachment and detachment of the drug cassette 420, the base unit 430 is configured such that the spline shaft 413i is engaged with the cylindrical unit 413g as the cassette is attached so that, in the engaged state, the rotation of the motor 413j is transmitted to the cylindrical unit 413g via the spline shaft 413i. A through hole 413h (drug falling passage) is formed in the base 413k so as to communicate with the ejection outlet 413f when the drug cassette 420 is attached to the base unit 430.

In the tablet packing machine 500 in which a large number of base units 430 such as described above are provided (see FIG. 13C), the conduit pipe 414 is built in the drug feeder storage 412 so as to extend vertically, and the conduit pipe 540 is built in the drug feeder storage with cassette interchangeability 510 so as to extend vertically. The ejection outlet 413f of the drug feeder 413, 530 communicates with the nearby conduit pipe 14 via the through hole 413h of the base 13k and an extension pipe appropriately provided. The drug 1 ejected from the drug feeder 413, 530 is respectively led to the conduit pipe 414, 540 via the through hoe 413h and then guided to the collecting member 415 after a free fall through the conduit pipe 414, 540. The collecting member 415 is built in the tablet packing machine at a location below the drug storage 411 and above the packaging apparatus 417. The upper-end opening thereof opens wide enough to cover the lower ends of all conduit pipes 414, while the lower-end opening thereof is narrowed down toward the drug input unit 416 of the packaging apparatus 417. The drugs 1 guided by the conduit pipes 414 and 540 are collected toward the lower-end opening before being forwarded to the packaging apparatus 417.

Shutter members (not shown) for temporarily retaining falling drugs are built in the conduit pipes 414 and 540 and in the drug collecting channels in the drug collecting mechanism 415. The drugs 1 to be packed together after being ejected from associated drug feeders 413 and 530 can be timed to fall to the collecting mechanism 415 simultaneously via the conduit pipes 414 and 540 or can be timed to be input to the drug input unit 416 of the packaging apparatus 417 simultaneously via an outlet at the lower end of the collecting mechanism 415. The drugs 1 passing through the drug collecting channel are packed in the packing strip 2 by the packaging apparatus 417. The packaging apparatus 417 feeds the packing strip 2 a predetermined length at a time and packs the drugs by heat sealing the strip. As described, the drugs are automatically packed such that the drugs 1 are fed from associated drug feeders 413 to the packaging apparatus 417 via the collecting mechanisms 414 and 415 one by one or in units of multiple tablets.

Each of the drug feeders 413 and 530 is also provided with a checking means for reading and checking identification information in order to verify whether the drug cassette 420 attached to the base unit 430 is proper (see FIGS. 14A through 14G). More specifically, the drug cassette 420 is provided with an identification information bearing member 421 for holding identification information. The base unit 430 is provided with a reading device 31 for reading identification information from the identification information bearing member 421 and a microprocessor 440 of a one-chip type provided with a built-in memory. The identification information bearing member 421 is a sticker with a scanned surface on which, for example, a total of eleven white or black marks are arranged in a single row. The sticker is pasted to the underside of the drug cassette 420. The reading device 431 is configured such that as many reflective photosensors as the number of marks on the identification information bearing member 421 are also arranged in a single row. The reading device 431 is provided on top of the base unit 430. In a state in which the drug cassette 420 is attached to the base unit 430, the reading device 431 and the identification information bearing member 421 are opposite to each other to facilitate reading.

To allow each of the drug feeders 413 and 530 or, more specifically, the base unit 430, to check the identification information by using the result of reading by the reading device 431, the reading device 431 is connected to the microprocessor 440. A memory 450 in the microprocessor 440 stores check data 451. The microprocessor 440 has a checking routine 447 installed therein to check the result of reading by the reading device 431 against the check data 451 (see FIGS. 14F and 14G). Also installed in the microprocessor 440 is an I/O routine 441 for signal exchange with the rack control circuits 561 and 563 via an intra-rack wiring 562, an expansion of the intra-rack wiring 462.

Further, the base unit 30 is provided with a lighted indicator 432 (for example, a green LED) for easy visual identification (see FIG. 14E). In the base unit 430 of the drug feeder 413 of the first group, the indicator 432 is used to show a communication enabled state or drug ejection disabled state. In the base unit 430 of the drug feeder 530 of the second group, the indicator 432 is used to provide guidance on the location of attachment of the replacement drug cassette 420. In the illustration, only one indicator 432 is provided in the base unit 430. Alternatively, the base unit 430 may be provided with multiple indicators 432 of different colors that are suitably used depending on the required function. Also provided in the base unit 430 are an ejection sensor 433 for detecting the drug 1 as it passes the through hole 413h, and an attachment/detachment sensor 434, such as a mechanical switch, for detecting whether the drug cassette 420 is attached to the base unit 430. A manually-operated switch 35 operated to activate the expanded function of the checking function is also provided where it is concealed in a small hole or the like.

These components (432, 433, 434, 435) are also connected to the microprocessor 440 and are subject to its control, similar to the reading device 431 and the motor 413j. The indicator 432, the ejection sensor 433, the attachment/detachment sensor 434 and the motor 413j are connected to the rack control circuits 561 and 563 via the microprocessor 440 as well as via the intra-rack wiring 562. Signal transfer processing by the I/O routine 441 enables the indicator 432, the ejection sensor 433, the attachment/detachment sensor 434 and the motor 413j to be subject to the control of the rack control circuits 561 and 563 by allowing these components to exchange signals with the rack control circuits 561 and 563, in substantially the same manner as when the components are directly controlled by the rack control circuit 461 via the intra-rack wiring 462. The result of reading by the reading device 431 is delivered to the checking routine 447 described above. The operational status of the manually-operated switch 435 is delivered to a saving and restoring routine 447a and an overwriting routine 447b described later.

To describe the function of the microprocessor 440 in detail (see FIGS. 14F and 14G), the checking routine 447 compares the check data 451 stored in the memory with the result of reading by the reading device 431 at the time of attaching the drug cassette 420 to the base unit 430 and, optionally, at an appropriate point of time during an operation for attaching the cassette as well. This is equally true of the drug feeder 413 and the drug feeder 530. The check data 451 is formed, for example, as 11-bit data, like the marks on the identification information bearing member 421, so that it is immediately known whether or not the data matches the result of reading by the reading device 31 by comparison. If the result of comparison indicates matching failure, the checking routine 447 sends out an associated signal to the rack control circuits 561 and 563 via the I/O routine 441 and the intra-wiring 562 in order to suspend motor-driven ejection by the associated base unit 430. If the result of scanning the identification information bearing member 421 and the check data 451 in the memory 450 match, the checking routine 447 sends out an associated signal to the rack control circuits 561 and 563 via the I/O routine 441 and the intra-rack wiring 562 so as to enable motor-driven ejection by the associated base unit 430.

The check data 451 is written in the memory 450 using a writing tool such as a general-purpose ROM writer or a dedicated writer. The stand-alone memory 450 may be temporarily installed in the tool to write specified data in a specified address. It is also possible to download the check data registered in the drug master table of the control console 590 to the microprocessor 440. In the case of the drug feeder 530 belonging to the second group in which top priority is given to interchangeability, it is convenient and error free to transfer to the memory 450 the identification information of the drug cassette 420 as it is attached to the base unit 430. Therefore, in addition to the checking routine 447, the overwriting routine 447b is installed in the microprocessor 440 of the base unit 430 of the drug feeder 530 (see FIG. 14G). When the manually-operated switch 435 is operated, the program allows the reading device 431 to read the identification information from the identification information bearing member 421 of the drug cassette 420 currently attached to the base unit 430 so that the check data 451 is overwritten with the identification information thus read.

In contrast, in the case of the drug feeder 413 belonging to the first group in which top priority is given to safety, the saving and restoring routine 447a for suspending the function of the checking means is installed in the microprocessor 440 of the base unit 430, in addition to the checking routine 447 (see FIG. 14F). An area used by the saving and restoring routine 447a to store saved data 452 is reserved in the memory 450. When the manually-operated switch 435 is operated, the saving and restoring routine 447a transfers current values of the check data 451 as the saved data 452 and then clears the check data 451 to zero. When the manually-operated switch 435 is operated a second time, the saving and restoring routine 447 overwrites the check data 451 with the values saved as the saved data 452. In association with this, the checking routine 447 does not perform a comparing process and a checking process while the check data 451 is cleared to zero.

Thus, in the tablet packing machine 500, in addition to the checking means, the check bypassing means is operably built in those of the microprocessors 440 respectively attached to a large number of base units 430 that are classified in the first group. The overwriting means is not built in the microprocessors 440 of this group. The overwriting means, in addition to the checking means, is operably built in those of the microprocessors 440 of the second group. The check bypassing means is not provided in the microprocessors 440 of this group. The check bypassing means includes means to save and restore the check data. The overwriting means overwrites the check data with the identification information read by the reading device.

The control console 590 (see FIG. 15) uses different drug ejection instructions depending on the grouping of the base unit 430. The functions of the control console 590 are expanded so as to be capable of integrally managing a mixed system in which the tablet packing machine 500 and the tablet packing machine 410 already described are colocated. More specifically, an "AC flag", an item of expanded functions, is assigned to a portion of the free area reserved for future expansion in each record in the drug master table. If the associated drug cassette 420 is for the drug feeder 413 of the first group, the AC flag is turned off. If the associated drug cassette 420 is for the drug feeder 530 of the second group, the AC flag is turned on (see FIG. 16A). The drug master table is expanded by a table editing program or the like as part of the initialization of the tablet packing machine 500 newly installed. The AC flag when turned off is designed to be of the same value occurring when the free area reserved for future expansion is cleared to zero so that table updating can be omitted in the existing tablet packing machine 410.

When creating a drug ejection instruction addressed to the drug feeder 413 of the first group, the control console 590 includes in the instruction the feeder storage address (the drug feeder storage address related to the drug feeder storage) retrieved from the drug master table, as is similarly done by the control console 409. The control console 590 further appends the AC flag turned off to the instruction (see FIG. 16B). A difference from the control console 409 is that, when creating a drug ejection instruction addressed to the drug feeder 530 of the second group, the control console 590 includes in the instruction the check data (data compared with the cassette identification information) retrieved from the drug master table, instead of the feeder storage address. The control console 590 further appends the AC flag turned on to the instruction.

Whether the drug cassette 420 belongs to the first group or the second group is determined by referring to the AC flag. While the contents of identification information assigned to the drug cassette 420 is not constrained by the grouping, it will be assumed here that values in the range between "1" and "500" are assigned to the first group and values in the range between "501" and "2000" are assigned to the second group, to facilitate checking of operations. The value "0" is not used as the identification information of the drug cassette 420 since it is also the value occurring when the check data 451 is cleared to zero to bypass the checking process. Although the majority of base units 430 are of the first group and there are smaller number of base units 430 of the second group, there may be a larger number of drug cassettes 420 of the second group than those of the first group because cassettes of the second group are used as replacements.

The rack control circuit 561 (see FIG. 17) also comprises a microprocessor or the like. A communication routine 442a as a means for communication, an ejection detecting routine 443 for detecting whether the drug is ejected or not, or whether the drug is ejected properly, a table search routine 444 for accessing a port table 444a, an attachment/detachment detecting routine 445 as a means for detecting whether the cassette is attached or detached, an information transmitting routine 446 as a transmitting means and an ejection control routine 448 as a means for motor-driven ejection control are installed in the rack control circuit 561 in order to control several to several tens of drug feeders 413 (the base units 430 of the first group) via the individual intra-rack wirings 562.

The communication routine 442a receives an instruction from the control console 590 or, in some cases, the controller 580 via the internal communication means 460 and also transmits status or data to the control console 590. Instructions received by the communication routine 442a include a drug ejection instruction and an information uploading instruction. A process involving the drug ejection instruction will be described in detail. Upon receipt of a drug ejection instruction, the communication routine 442a checks the AC flag included in the instruction. If the AC flag is turned on, the communication routine 442a disregards the instruction. If the AC flag is turned off, the communication routine 442a delivers the instruction to the table search routine 444.

The table search routine 444 retrieves a feeder storage address from the drug ejection instruction received from the communication routine 442a and searches the port table 444a using the retrieved address as a key. The number of valid records contained in the port table 444a is equal to the number of drug feeders 413 under the control of the rack control circuit 561. Each record includes items like a feeder storage address, status of cassette attachment/detachment and an I/O port number. By retrieving the I/O port number from a record in the port table 444a containing a feeder storage address that matches the address included in the drug ejection instruction, the table search routine 444 identifies the drug feeder 413 to be operated for drug ejection and, more specifically, the intra-rack wiring 562 and the microprocessor 440 at the destination of signal transmission. If the drug cassette 420 is attached to the identified drug feeder 413, the table search routine 444 delivers the drug ejection instruction to the ejection control routine 448. If not, the table search routine 444 causes the information transmitting routine 446 to notify the control console 590 of the detachment of the cassette.

The attachment/detachment detecting routine 445 monitors the status of attachment/detachment of the drug cassette 420 to the base unit 430 of the drug feeder 413. Each time the status changes, the attachment/detachment detecting routine 445 updates associated items in the port table 444a. More specifically, the attachment/detachment detecting routine 445 receives a detection output from the attachment/detachment sensor 434 of the base unit 430 of the drug feeder 413. By referring to a change in the detected value or by referring to a message signal output when the cassette is attached or detached, the attachment/detachment detecting routine 445 detects that the drug cassette 420 is attached to the base unit 430 or detached therefrom. The attachment/detachment detecting routine 445 writes associated information as an item in the port table 444a to indicate whether the cassette is attached or detached. In addition, the attachment/detachment detecting routine 445 causes the information transmitting routine 446 to notify the control console 590 of the status of cassette.

Upon receipt of the drug ejection instruction and the I/O port number from the table search routine 444, the ejection control routine 448 causes the motor 413j of the associated drug feeder 413 to be rotated via the intra-rack wiring 562 and the microprocessor 440 identified by the I/O port number. When the ejection sensor 433 detects that as many drugs 1 as designated by the drug ejection instruction have been ejected, the ejection control routine 448 suspends the rotation of the motor 413j. The result of detection by the ejection sensor 433 of the associated drug feeder 413 is input to the ejection detecting routine 443 via the microprocessor 440 provided in the base unit 430 and via the intra-rack wiring 562 connected to the microprocessor 440. The result of detection is then delivered from the ejection detecting routine 443 to the ejection control routine 448. After the ejection control routine 448 is notified by the checking routine 447 of the microprocessor 440 of the drug feeder 413 of matching failure via the intra-rack wiring 562, the ejection control routine 448 suspends the rotation of the motor 413j even if it receives the drug ejection instruction. After the ejection control routine 448 is notified by the checking routine 447 that matching is established, the ejection control routine 448 resumes the rotation of the motor 413j in accordance with the drug ejection instruction.

Like the rack control circuit 561, the rack control circuit 563 (see FIG. 17) also comprises a microprocessor or the like. A communication routine 442b as a means for communication, an ejection detecting routine 443 for detecting whether the drug is ejected or not, or whether the drug is ejected properly, a table search routine 444 for accessing a port table 444b, an attachment/detachment detecting routine 445 as a means for detecting whether the cassette is attached or detached, an information transmitting routine 446 as a transmitting means and an ejection control routine 448 as a means for motor-driven ejection control are installed in the rack control circuit 563. Another point of similarity with the rack control circuit 561 is that the rack control circuit 563 is connected to several to several tens of microprocessors 440 under its control via the individual intra-rack wirings 562 to enable signal exchange. Unlike the rack control circuit 561, however, the drug feeder 530 (the base unit 430 of the second group) is subject to the control of the rack control circuit 563 and, therefore, the communication routine 442b and the port table 444b are partly different from the communication routine 442a and the port table 444a, respectively.

To be more specific, the communication routine 442b receives an instruction from the control console 590 or, in some cases, the controller 580 via the internal communication means 460 and also transmits status or data to the control console 590. Instructions received by the communication routine 442b include a drug ejection instruction and an information uploading instruction. As such, the communication routine 442b is similar to the communication routine 442a. However, the communication routine 442b processes the drug ejection instruction differently from the communication routine 442a. That is, upon receipt of a drug ejection instruction, the communication routine 442b checks the AC flag included in the instruction. If the AC flag is turned off, the communication routine 442b disregards the instruction. If the AC flag is turned on, the communication routine 442b delivers the instruction to the table search routine 444. With this, the drug ejection instruction is forwarded from the communication routines 442a and 442b to the drug feeder 413 of the first group or the drug feeder 530 of the second group, depending on whether the AC flag is turned on or off.

In agreement with the fact that the drug ejection instruction in which the AC flag is turned off contains check data instead of a feeder storage address as a destination of the instruction, each record in the port table 444b includes items like check data, status of cassette attachment/detachment and an I/O port number. The number of valid records contained in the port table 444b is equal to the number of drug feeders 530 (more specifically, the number of base units 430 of the second group) under the control of the rack control circuit 563.

The table search routine 444 retrieves the check data from the drug ejection instruction received from the communication routine 442b and searches the port table 444b using the retrieved data as a key.

If the search is successful and the I/O port number is retrieved from a record in the port table 444b containing the check data that matches the data included in the drug ejection instruction, the table search routine 444 identifies the drug feeder 530 (more specifically, the intra-rack wiring 562 and the microprocessor 440 at the destination of signal transmission) to be operated for drug ejection. If the drug cassette 420 is attached to the identified drug feeder 530, the table search routine 444 delivers the drug ejection instruction to the ejection control routine 448. If the drug cassette 420 is not attached to the identified drug feeder 530, the table search routine 444 lights the indicator 432 provided in the base unit 430 of the identified drug feeder 530 to provide guidance on a destination base to which a cassette should be attached. When the desired drug cassette 420 is attached, the table search routine 444 turns the indicator 432 off and delivers the drug ejection instruction to the ejection control routine 448.

If the search in the port table 444b fails, the table search routine 444 selects a record with the oldest update history in the port table 444b and updates that record by overwriting the check data in the record with the check data included in the drug ejection instruction. The table search routine 444 sends the check data to the microprocessor 440 of the base unit 430 of the drug feeder 530 identified by the I/O port number included in that record so as to update the check data 451 of the microprocessor 440. The table search routine 444 then lights the indicator 432 provided in the base unit 430 of the identified drug feeder 530 for guidance on a destination base to which a cassette should be attached. When the desired drug cassette 420 is attached or when the existing drug cassette 420 is replaced by the desired drug cassette 420, the table search routine 444 turns the indicator 432 off and delivers the drug ejection instruction to the ejection control routine 448.

When lighting a desired indicator 432 provided in the base unit 430 for guidance on a destination base to which a cassette should be attached, the table search routine 444 is designed to also light several indicators 432 in the neighborhood to make the guidance more visible. A variety of lighting patterns may be available. In the illustrated example, the indicators 432 on the same rack are lighted all at once, whereupon the most distant indicator 432 is turned off, followed by the less distant indicators 432, until only the target indicator 432 is lighted. This pattern is repeated. The lighting for guidance on the destination of cassette attachment is important for the drug feeder 530 of the second drug feeder which is stored in the feeder storage with cassette interchangeability 510 and in which the interchangeability is given top priority. The guidance function is also useful in drug refilling of the drug feeder 413 of the first group which is stored in the drug feeder storage 412 and in which safety is given top priority. In prompting a user to attach or replace the drug cassette 420, the table search routine 444 not only lights the indicator 432 but also directs the information transmitting routine 446 to send an electronic message designating a request for lighting to the controller 580 or the control console 590.

The controller 580 (tablet packing machine main controller) monitors a drug ejection instruction issued from the control console 590. If the AC flag in the drug ejection instruction is turned off and the feeder storage address is included in the instruction as a destination, the controller 580, similarly to the controller 418, variably times the opening and closing of shutters in the drug collecting mechanisms 414 and 415 as well as timing the operation of the packaging apparatus 417, by estimating the time required for a drug to fall from the drug feeder 413 by referring to the column address in the drug feeder storage address. If the AC flag in the drug ejection instruction is turned on and the identification data, instead of the feeder storage address, is included in the instruction, the controller 580, unlike the controller 418, employs the longest time of drug fall from the base units 430 (i.e. the base unit 430 of the drug feeder 530 of the second group) stored in the feeder storage with cassette interchangeability 510, to estimate the time required for a drug to fall from the drug feeder 530.

The usage mode and the operation of the drug feeder and the automatic drug dispenser according to the third embodiment-1 will be described with reference to the drawings. FIGS. 18A-18G shows an example of how the indicators in the feeder storage with cassette interchangeability are lighted, illustrating time-dependant change in lighted status.

When prescription data or drug dispensing data derived therefrom related to the tablet packing machine 410 or the tablet packing machine 500 under the control of the control console 590 are input to the control console 590, the control console 590 refers to the drug master table and prepares a drug ejection instruction and transmits the instruction to the tablet packing machine 410 or the tablet packing machine 500 via the internal communication means 460. If the drug ejection instruction is addressed to the tablet packing machine 410 or to the drug feeder 413 of the first group stored in the drug feeder storage 412 of the tablet packing machine 500, the drug ejection instruction according to the third embodiment-1 is the same as the instruction according to the other embodiments except that the AC flag appended is turned off. Drugs to be packed in accordance with such an instruction are normally accommodated in the drug storage 411 so that they can be automatically ejected. Therefore, automatic drug packing is performed in the tablet packing machine 500 as in the tablet packing machine 410.

That is, when the drug ejection instruction is transmitted from the control console 590 to the tablet packing machine 500, the drug ejection instruction is received by the rack control circuit 561 since the AC flag is turned off. The instruction is then used by the table search routine 444 to search the port table 444*a*. As a result of cooperation between the microprocessor 440 of the drug feeder 413 identified as a result of the search and the ejection control routine 448 of the rack control circuit 561, a designated number of drugs 1 are caused to fall from the drug feeder 413 for ejection. The drugs 1 are input to the drug input unit 416 of the packaging apparatus 417 via the drug collecting mechanisms 414 and 415 and are packed in the packing strip 2 by the packaging apparatus 417. In this process, the drug ejection instruction is monitored by the controller 580. The timing of the fall of the drug 1 and the timing of packing by the packaging apparatus 417 are optimally adjusted by controlling the opening and closing of shutters in accordance with the feeder storage address included in the drug ejection instruction as a destination.

If the drug cassette 420 of the drug feeder 413 to be operated for drug ejection is empty or not attached, the controller 580 or the control console 590 provides an alarm display prompting a user to refill the cassette with drugs or attach the cassette, by referring to the result of detection by the attachment/detachment detecting routine 445 or the like, or the status report provided by the information transmitting routine 446. When an operator attaches the proper drug cassette 420 to the base unit 430, the reading device 431 of the base unit 430 scans the identification information bearing member 421 of the drug cassette 420. The checking routine 447 compares the identification information with the check data 451 stored in the memory 450 of the microprocessor 440. In they do not match, the ejecting operation is suspended. Therefore, improper packing due to improper attachment of the drug cassette 420 is prevented.

In contrast, if the drug ejection instruction is addressed to the drug feeder 530 of the second group stored in the feeder storage 510 with cassette interchangeability 510 of the tablet packing machine 500, the AC flag turned on is appended to the drug ejection instruction and the check data to be compared with the identification information of the drug cassette 420 is included in the instruction as a destination. In this case, when the drug ejection instruction is transmitted from the control console 590 to the tablet packing machine 500, the drug ejection instruction is received by the rack control circuit 563 since the AC flag is turned on. The instruction is then used by the table search routine 444 to search the port table 444*b*. If the drug cassette 420 bearing the identification information designated by the drug ejection instruction is attached to the base unit 430 of the drug feeder 530 identified as a result of the search, cooperation between the microprocessor 440 of the drug feeder 530 and the ejection control routine 448 of the rack control circuit 563 causes a designated number of drugs 1 to fall from the drug feeder 530 for ejection. Similarly to the case of the drug feeder 413, the drug 1 is input to the drug input unit 416 of the packing machine 417 via the drug collecting mechanisms 540 and 414 and is packed in the packing strip 2 by the packaging apparatus 417. The controller 580 adjusts the timing of fall and the timing of packing so as to be on the safer side, by using the longest time of drug fall from the drug feeders 530.

If the drug cassette 420 bearing the identification information that matches the check data included in the drug ejection instruction is not attached to any of the base units 430 in the feeder storage with cassette interchangeability 510, the controller 580 or the control console 590 provides an alarm display prompting a user to attach or replace the drug cassette 420, in accordance with the electronic message from the table search routine 444 of the rack control circuit 563. In parallel with this, the table search routine 444 of the rack control circuit 563 lights the indicator to provide guidance on the destination of cassette attachment. To describe the operation using a specific example (see FIGS. 18A through 18G), it will be assumed that eight identical drug feeders 530 are arranged on the same rack in the feeder storage with cassette interchangeability 510 and that a need arises to replace the drug cassette 420 at the fourth feeder from left (see where outlined arrow points in FIGS. 18A through 18G).

Figure 18A:
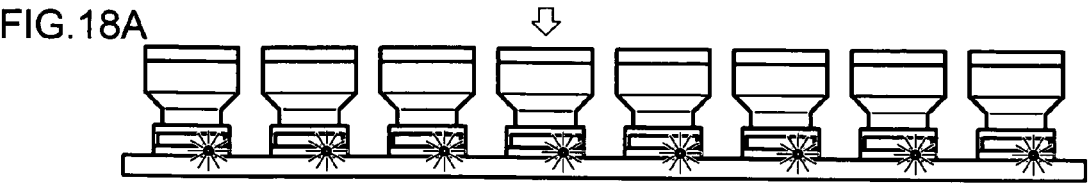
FIGS. 18A-18G show an example of how indicators in a feeder storage with cassette interchangeability are lighted.
Figure 18B:
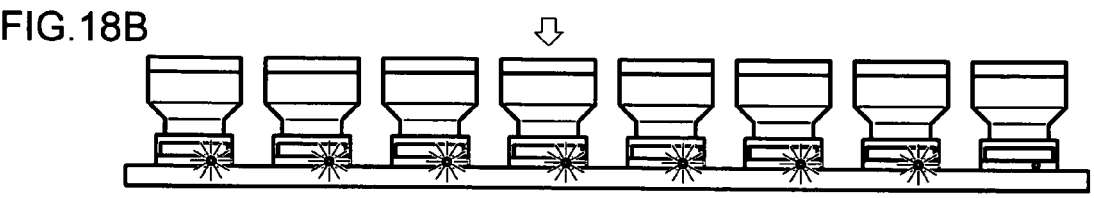
Figure 18C:
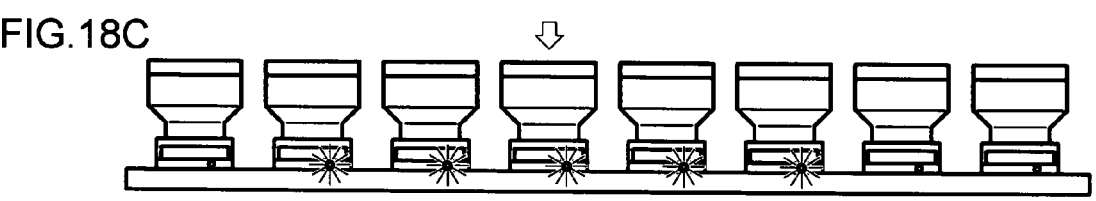
Figure 18D:
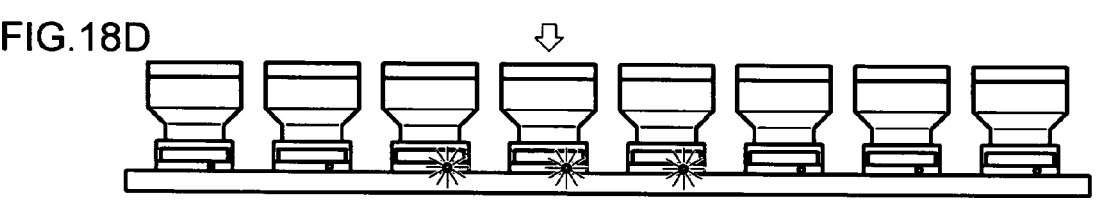
Figure 18E:
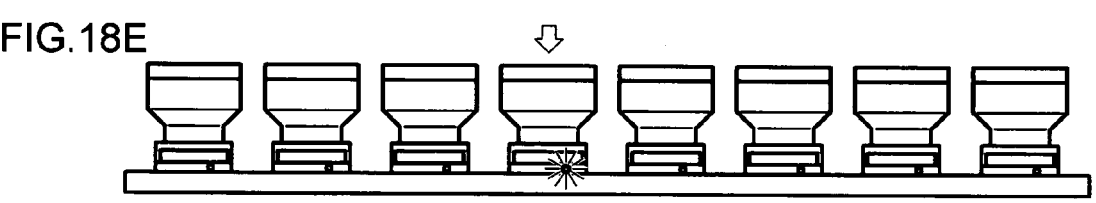
Figure 18F:
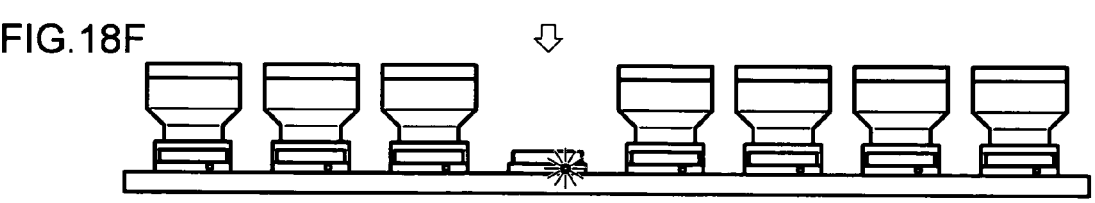

In this case, the indicators 432 of the base units 430 of the eight drug feeders 530 on the rack are lighted all at once (see FIG. 18A). After a certain interval, the indicator 432 at the right end is turned off (see FIG. 18B). After another interval, the leftmost indicator 432 and the seventh indicator 432 from left are turned off (see FIG. 18C). After yet another interval, the second and sixth indicators 432 from left are turned off (see FIG. 18D). After yet another interval, the third and fifth indicators 432 from left are turned off (see FIG. 18E). The fourth indicator 432 from left where replacement should take place continues to be lighted. Even when the undesired drug cassette 420 is removed (FIG. 18F), the lighting pattern, with a lighted range being progressively narrowed down until only the target indicator 432 is lighted, is repeated.

Figure 18G:
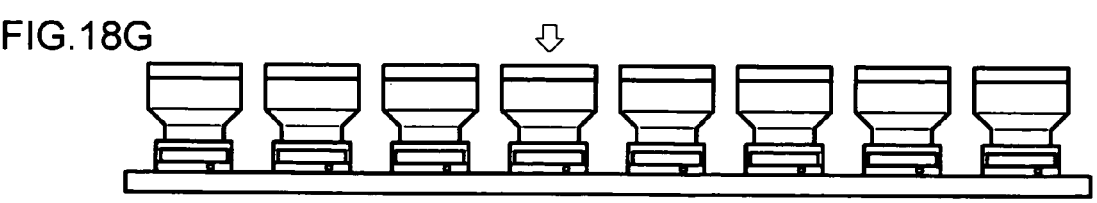

When the drug cassette 420 bearing the identification information that matches the check data included in the drug ejection instruction is taken out by operation personnel from the stock rack 520 and attached to the fourth base unit 430 from left where replacement should take place, all the indicators 432 are turned off (see FIG. 18G). When the manually-operated switch 435 at the base unit 430 is operated for confirmation, the overwriting routine 447b installed in the microprocessor 440 provided in the base unit 430 overwrites and updates the check data 451. The rack control circuit 563 updates the item of check data in a corresponding record in the port table 444b by overwriting. Thus, a large number of drug cassettes 420 stocked in the stock rack 520 are also automatically set up for drug ejection. For drugs not accommodated not only in the drug feeder storage 412 or the feeder storage with cassette interchangeability 510 but also in the drug cassettes 420 in the stock rack 520, the manual dispensing unit 410a will continue to be used as in the other embodiments. The frequency of having to use the unit 410a, however, is quite low.

Given above is an explanation of a situation where automatic packing is properly performed. There are a large number of drug feeders 413 of the first group stored in the drug feeder storage 412 and, in addition, the drug type and dosage form come in a large variety. Thus, unexpected troubles may occur in some drug feeders 413 such as delay in feeding and cracking in a drug. Such trouble in drug ejection is likely to occur when the operation of a packing machine is started or when a new drug is introduced into the system. A trouble may, however, during the operation. In such a case, the manually-operated switch 435 at the base unit 430 of the target drug feeder 413 is operated in order to manually determine whether the trouble occurred in the cassette 420 or the base unit 430, or whether the drug feeder 413 and the drug 1 are not compatible with each other.

When the manually-operated switch 435 is operated, the saving and restoring routine 447a of the microprocessor 440 saves the check data 451 as the saved data 452 and clears the check data 451 to zero. With this, the checking function of the checking routine 447 is suspended in the drug feeder 413 so that checking function in the drug cassette 420 is bypassed. The indicator 432 of the base unit 430 is lighted to indicate the source of the trouble. When the checking function in the drug cassette 420 is bypassed, the cassette 420 and the base unit 430 can be manually checked while avoiding an alarm issued by the control console 590 or incorrect data collection by the control console 590.

If it is desired that the drug cassette 420 in which the trouble occurred be temporarily attached to another base unit 430 to check its operation, the manually-operated switch 435 at the base unit 430, which is the temporary destination of attachment, is operated so that the checking function at the destination base unit 430 is bypassed. When the checking function for checking the drug cassette 420 is bypassed at the temporary destination base unit 430, the indicator 432 at the destination base unit 430 is lighted to indicate that manual operation independent of the management of the control console 590 is enabled. Similarly to the case described above, the check data 451 otherwise used in the checking at the temporary destination base unit 430 is temporarily saved as the saved data 452. The reading device 431 scans the identification information bearing member 421 of the drug cassette 420 but the checking routine 447 does not perform checking. Thus, while the indicator 432 at the temporary destination base unit 430 remains lighted, the same drug cassette 420, i.e. the drug cassette 420 in which the trouble occurred, can remain temporarily attached to the base unit 430 in which the indicator 432 is lighted.

When the manual checking is completed, the manually-operated switch 435 of the target base unit 430 is operated again. Thereupon, the values saved as the saved data 452 by the saving and restoring routine 447a of the microprocessor 440 provided in the base unit 430 are returned to the check data 451. The checking function of the checking routine 447 is restored in the drug feeder 413 so that the checking of the drug cassette 420 is resumed.

Thus, it is possible to easily and safely test replacement of drug cassettes in the drug feeder 413 of the first group in which safety is given top priority, without requiring rewriting of a drug master table.

An additional explanation will be given of a need to bypass checking in the temporary destination base unit 430 as well as in the base unit 430 in which the trouble occurs. In most cases, trouble checking involves removal of the drug cassette 420 from the base unit 430 in which a trouble occurs and attachment of it to the temporary destination base unit 430. These steps are repeated several times with different temporary destinations before settling on proper arrangement. Provision for locally bypassing checking in the temporary destination base unit 430 helps these steps to be repeated easily, accurately and promptly. That the check bypassing means comprises saving of the check data 451 as the saved data 452 and restoring the check data 451 from the saved data 452 enables the saved data at the temporary destination to be returned to the check data easily.

Examples of tablets that are likely to bounce higher in proportion to the height from which they fall include tablets with solid surfaces such as sugar-coated tablets or uncoated tablets that are compression molded to a predetermined configuration at a low pressure. For these drugs, troubles may often be prevented by attaching the drug cassette 420 at a low height. With other drugs that are opposite in characteristics, troubles are unlikely to occur even if the cassette is attached at a relatively high position. Trouble checking involving movement and replacement of the drug cassette is conducted on a trial and error basis by considering the above-described characteristics of drugs.

Types of drugs accommodated in the drug feeder 413 for automatic ejection differ from hospital to hospital. Data on drugs that are employed only in some hospitals for automatic ejection may be set in the drug master table. Manufacturers responsible for the installation of a drug dispensing system such as the tablet packing machine, however, may have to install the machine without any drug samples available. In such a case, the manufacturer may initially set up the tablet packing machine by registering the feeder storage address, the check data and the like in the drug master table, while arranging the drug feeders 413 for accommodating hospital-specific drugs in the drug feeder storage 412 in the alphabetical order. Manufacturer's personnel register the data in the drug master table once the drug feeders 413 are set and then modify the feeder arrangement as required upon reviewing dosage forms and the frequency of troubles. The personnel reconfigure the drug master in accordance with the modified feeder arrangement. As the personnel are responsible for speedy and accurate on-site fine-tuning as described above, the process has required extensive rules of thumb in the related art. With the inventive drug feeder and automatic dispenser, trouble checking can be performed easily by moving and replacing drug cassettes while ensuring that checking is bypassed.

Third Embodiment-2

A description will now be given of the specific structure of the drug feeder and automatic drug dispenser according to the third embodiment-2 with reference to the drawings. FIG. 19 is a block diagram showing the overall structure of a control system. FIGS. 20A and 20B are block diagrams showing the primary functions of the microprocessor 440 provided in each of the base units 430 in a distributed fashion, where FIG. 20A is a functional block diagram of the microprocessor 440 of the first group provided in the base unit 430 of the drug feeder 413 in the drug storage 411; and FIG. 20B is a functional block diagram of the microprocessor 440 of the second group provided in the base unit 430 of the drug feeder 530 in the feeder storage with cassette interchangeability 510.

The automatic dispenser according to the third embodiment-2 differs from that of the third embodiment-1 in that the tablet packing machine 500 is modified to result in a tablet packing machine 600 by omitting the rack control circuits 561 and 563 (see FIG. 19). Additionally, the check bypassing means in the microprocessor 440 in the base unit 430 of the drug feeder 413 of the first group is implemented as a flag updating routine 447c and a switch flag 453 instead of the saving and restoring routine 447a and the saved data 452, the flag updating routine 447c being a means with which to update a flag for switching between different operations of the checking means (see FIG. 20A).

In place of the rack control circuit 561, the communication routine 442a, the ejection detecting routine 443, the attachment/detachment routine 445, the information transmitting routine 446 and the ejection control routine 448 are transferred to the microprocessor 440 provided in the base unit 430 of the drug feeder 413 of the first group (see FIG. 20A). These routines are modified to a certain extent so as to directly control actuating members such as the motor 413j but realize the same functions in the microprocessor 440 as when these routines are installed in the rack control circuit 561. Since these routines are installed in each of the microprocessor 440, eliminating the need to select the I/O port number, the table search routine 444 and the port table 444a are not installed. The communication routine 442a only receives the drug ejection instruction addressed to the feeder storage address of the base unit 430 to which the associated microprocessor 440 is attached and delivers the instruction to the other routines.

In place of the rack control circuit 563, the communication routine 442b, the ejection detecting routine 443, the attachment/detachment routine 445, the information transmitting routine 446 and the ejection control routine 448 are transferred to the microprocessor 440 provided in the base unit 430 of the drug feeder 530 of the second group (see FIG. 20B). These routines are modified to a certain extent so as to directly control actuating members such as the motor 413j but realize the same functions in the microprocessor 440 as when these routines are installed in the rack control circuit 563. Since these routines are installed in each of the microprocessor 440, eliminating the need to select the I/O port number, the table search routine 444 and the port table 444b are not installed. The communication routine 442b only receives the drug ejection instruction that includes the check data that matches the check data 451 in the associated microprocessor 440 and delivers the instruction to the other routines.

Of those functions assumed by the table search routine 444, the function of requesting the control console 590 to provide a display that prompts the attachment or replacement of the drug cassette 420 and the function of providing guidance on the destination of cassette attachment by lighting the desired indicator 432 and the neighboring indicators 432 are transferred to the controller 580. The flag updating routine 447c installed in the microprocessor 440 of the first group is configured to reverse the switch flag 453 in the memory 450 each time the manually-operated switch 435 is operated. The checking routine 447 checks the data by comparison in accordance with the value of the switch flag 453.

The rack control circuits 561 and 563 are not provided in the tablet packing machine 600 and their functions are distributed in the microprocessor 440 and the controller 580. Therefore, the same functions as are provided in the tablet packing machine 500 are provided in the tablet packing machine 600 so that repetition of the same description is avoided. Similarly to the tablet packing machine 500, the tablet packing machine 600 is capable of automatically packing various drugs under the management of the control console 590.

According to the inventive automatic dispenser, the control console 590 is capable of integral management of a system where the tablet packing machine 410, the tablet packing machine 500 and the tablet packing machine 600 are colocated, without causing any inconvenience.

[Other Points of Note]

The microprocessor 440 may not necessarily be of a one-chip type. The memory 450 may also be externally connected to the microprocessor 440. While the memory 450 should preferably be nonvolatile, the memory 450 may alternatively be provided with a battery.

The internal communication means 460 and other means for communication (for example, means for communication between machines) may be compliant with an ordinary communication protocol such as Ethernet™ or TCP/IP, or, alternatively, a protocol unique to the machine, as long as data can be exchanged between multiple machines and units. The communication means may also be wired or wireless, or may or may not be for multidrop communication.

In the embodiment described above, the feeder storage with cassette interchangeability 510 is provided on the right side of the table packing machines 500 and 600. Alternatively, the feeder storage with cassette interchangeability 510 may be provided at other positions including the left side or the front of the machine.

While the tablet packing machines 410, 500 and 600 in the embodiment are only designed for automatic packing of tablets, the machines may pack other types of drugs such as capsules. The tablet packing machines 410, 500 and 600 may be combined with a mechanism for packing powder medicine.

Fourth Embodiment

The fourth embodiment relates to an automatic drug dispenser for accommodating various drugs and automatically ejecting a desired drug for purposes including packing, in accordance with a prescription or an instruction for dispensing and, more particularly, to an automatic drug dispenser in which it is checked if a drug cassette that ejectably stores a drug matches a base unit when the cassette is attached to or detached from the base unit.

Figure 32A:
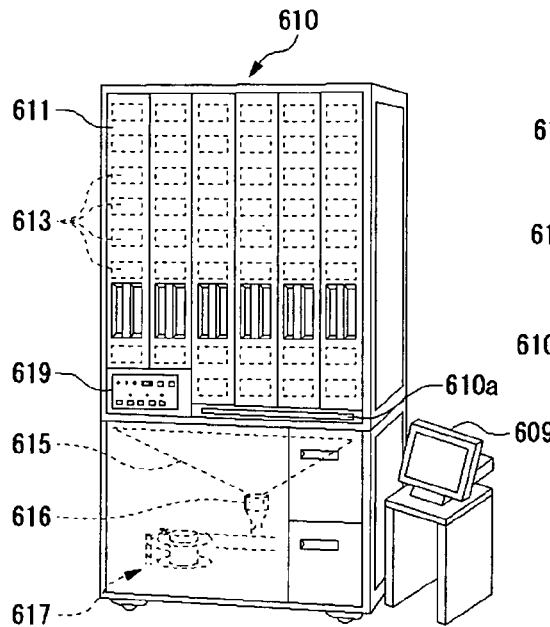
FIG. 32A is a perspective view showing the appearance of the tablet packing machine.
Figure 32B:
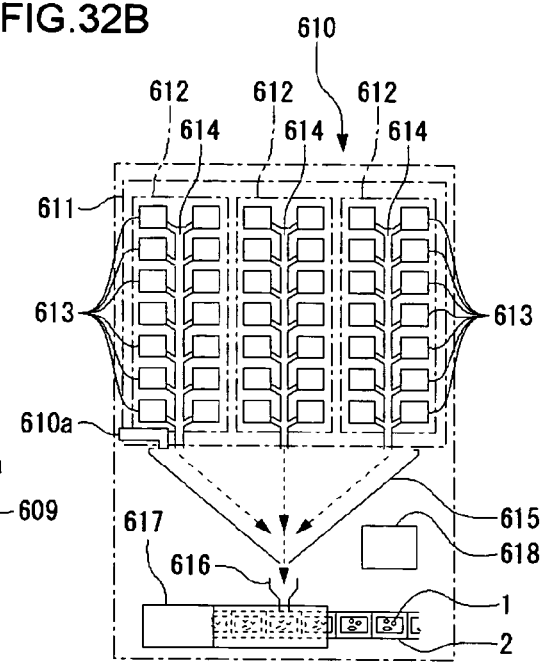
FIG. 32B is a schematic view showing the internal structure of the tablet packing machine.
Figure 32C:
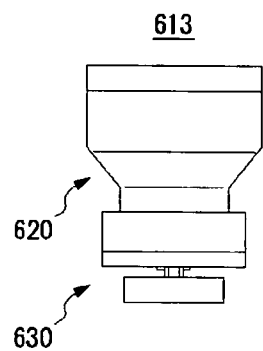
FIG. 32C is a left side view of the drug feeder.
Figure 32D:
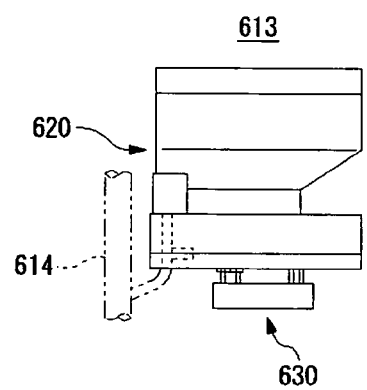
FIG. 32D is a front view of the drug feeder.
Figure 32E:
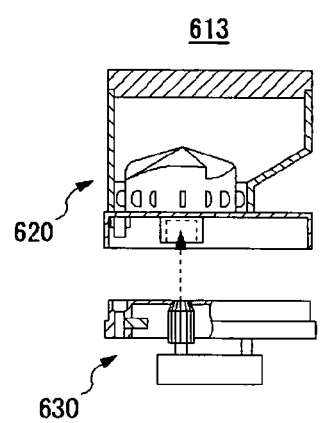
FIG. 32E is a longitudinal sectional view showing the left side of the drug feeder.
Figure 32F:
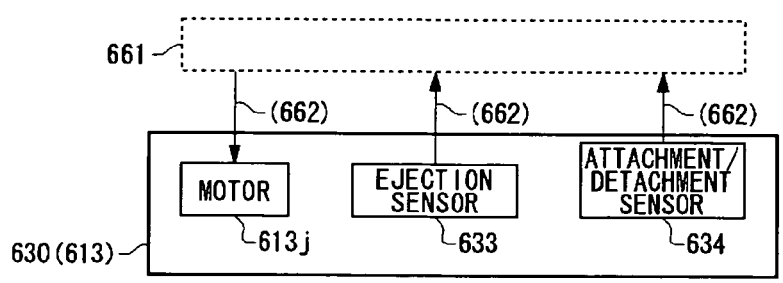
FIG. 32F is a control block diagram related to active components of the drug feeder.
Figure 33:
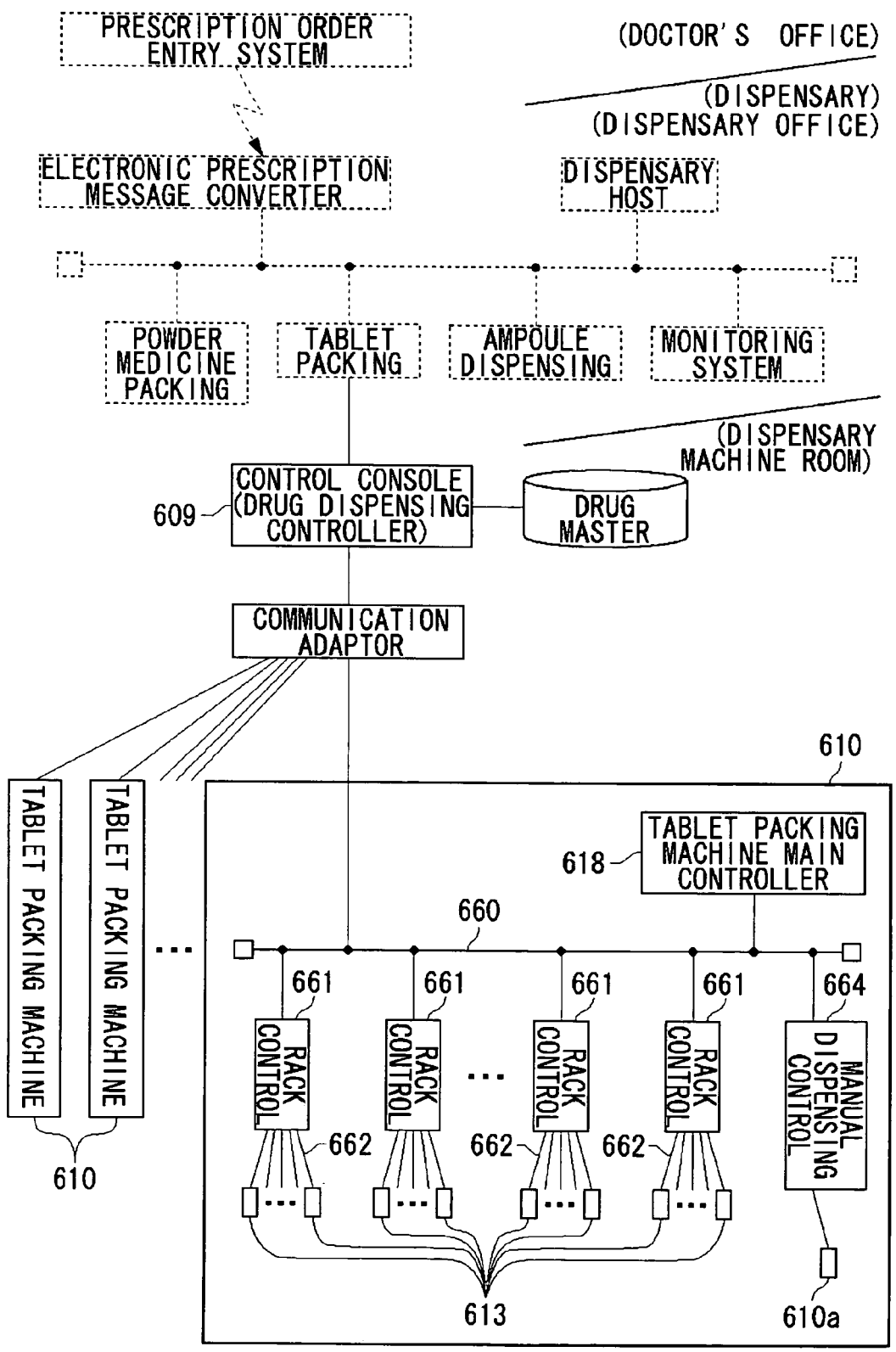
FIG. 33 is a block diagram showing the overall structure of the control system of the automatic drug dispenser.

A tablet packing machine 610, a typical embodiment of the inventive automatic drug dispenser, is illustrated. A further description will be given with reference to the illustration. FIGS. 32A-32F show a mechanical structure of the tablet packing machine 610 and a large number of drug feeders 613 built in the machine. FIG. 32A is a perspective view showing the appearance of the tablet packing machine 610; FIG. 32B is a schematic view showing the internal structure of the tablet packing machine 610; FIG. 32C is a left side view of the drug feeder 613; FIG. 32D is a front view of the drug feeder; FIG. 32E is a longitudinal sectional view showing the left side of the drug feeder; FIG. 32F is a control block diagram related to active components of the drug feeder 613. FIG. 33 is a block diagram showing the overall structure of the control system of the automatic drug dispenser; and FIGS. 34A and 34B show the structure of control data. FIG. 34A shows the structure of a record in a drug master table; and FIG. 34B shows the structure of an electronic message for an instruction for ejecting drugs.

The tablet packing machine 610 (see FIGS. 32A and 32B) comprises: a large number of drug feeders 613 accommodating various drugs 1 (disk-shaped drugs, ball-shaped drugs, capsules, cylinder-shaped drugs, tablets and the like) according to their categories; drug collecting mechanisms 614 and 615 for collecting drugs 1 ejected from the drug feeders 613; a packaging apparatus 617 for packing the drugs 1 received from the drug collecting mechanisms 614 and 615; and a controller 618 (tablet packing machine main controller, main control apparatus of the packing machine main body) embodied by a microprocessor system or the like. Under the control of the controller 618, a desired number of drugs 1 are ejected from the associated drug feeders 613 in accordance with prescription data or drug dispensing instruction data derived therefrom. The drug collecting mechanisms 614 and 615 collect the drugs 1 thus ejected and feed the drugs 1 to a drug input unit 616 (collected drug input inlet) provided downstream so that the drugs 1 are packed in the packaging apparatus 617. The drugs 1 are packed in packing strip 2 (packing paper) as they are compartmentalized according to a unit to be taken at a time or a unit to be administered at a time.

More particularly, the tablet packing machine 610 houses a drug storage 611 (a drug rack unit and a drug container storage) at the upper end of the machine and also houses the packaging apparatus 617 at the lower end thereof. Conduit pipes 614 (ducts, chutes, guide passages, upper drug collecting channels) and collecting members 615 (hopper-like members, funnel form members, lower drug collecting channels) constituting the drug collecting mechanism communicate between the drug storage 611 and the packaging apparatus 617. In the drug storage 611, multiple individually slidable drug feeder storages 612 (drug storages) are arranged horizontally. In each of the drug feeder storages 612, several to several tens of detachable drug feeders 613 are arranged vertically and horizontally. The storage position or the feeder storage address of each of the drug feeders 613 in the drug storage 611 is determined by a triplet comprising a column address, a row address and a board address. A column address indicates a position in the horizontal direction. More specifically, it indicates the ID number of the drug feeder storage 612. A row address indicates a position in the vertical direction. More specifically, it indicates the ID number of a rack board to which the drug feeder 613 is mounted. A board address indicates a position in the front-back direction or depth direction. More specifically, it indicates the order of the drug feeder 613 in the rack board. In a case where the drug feeders 613 are in a cylindrical arrangement (not shown), a feeder storage address is similarly determined if the ID number of the drug feeder storage 612 is unique.

Each drug feeder 613 (see FIGS. 32C-32E) is generally partitioned into a drug cassette 620 ejectably accommodating a large number of drugs 1, and a base unit 630 for detachably supporting the drug cassette 620 and driving a motor to eject drugs. The drug feeder 613 is designed to eject a designated number of drugs 1. Components built in the base unit 630 (see FIG. 32F) include a motor 613j provided as an actuator, an ejection sensor 633 provided as a means for detecting ejected drugs falling and an attachment/detachment sensor 634 provided as a means for detecting the attachment and detachment of a cassette. These components are connected to a rack control circuit 661 via individual intra-rack wirings 662 and are permanently fixed to the rack of the drug feeder storage 612. In contrast, the drug cassette 620 of the drug feeder 613 is detachable to facilitate refilling of the cassette with drugs.

Also built in the tablet packing machine 610 (see FIGS. 32A and 32B) are a manual dispensing unit 610a formed to be extractable from the housing in the forward direction and a manual drug dispensing apparatus provided with an actuating member (not shown) located in the housing to receive drugs from the manual dispensing unit 610a. Multiple vertically and horizontally arranged compartments are formed in the manual dispensing unit 610a. As such, the manual dispensing unit 610a is suitably used to manually dispense drugs per day multiple times, by compartmentalizing drugs so that each compartment contains drugs to be taken per day or each compartment contains drugs to be taken at each of different occasions in a day throughout a period in which drugs should be taken. The manual dispensing unit 610a is used to pack drugs not allocated to the drug feeders 613 together with the drugs allocated to the drug feeders 613. For example, intermittent driving of a conveyor inside the manual dispensing unit 610a sequentially ejects manually dispensed drugs (see, for example patent document No. 6).

A control console 609 (drug dispensing controller) is attached to the tablet packing machine 610 or provided as close as possible to it (see FIG. 32A) in order to integrally manage the automatic dispensing operation of the tablet packing machine 610. If the tablet packing machine 610 is a stand-alone, minimum system, the control console 609 and the tablet packing machine 610 are often integrally built. If the tablet packing machine 610 is a medium to large scale system comprising multiple machines, the control consol 609 manages multiple tablet packing machines 610; i.e. one-to-many or few-to-many management system is employed. Therefore, the control console 609 is often provided as an isolated, independent unit (see FIG. 33). In a stand-alone system in which the automatic drug dispenser is used in an isolated fashion, prescription data, prepared by converting the contents of prescription into electronic data, and drug dispensing data derived from the prescription data are input to the control console 609 via an input device (not shown). In a network-based system in which the control console 609 is connected to a prescription order entry system of a doctor's office or a host computer of a dispensary (see dotted lines in FIG. 33), prescription data prepared in the prescription order entry system, for example, are subject to data format conversion by an electronic prescription message converter in the middle of the network and are subject to data analysis by a dispensary host computer so as to be converted into drug dispensing data comprising data fit for automatic drug dispensing. Only the data related to the tablet packing machine 610 under the control of the control console 609 are forwarded to the control console 609.

For the purpose of preparing a drug ejection instruction on the basis of the prescription data or drug dispensing data derived therefrom, the control console 609 (see FIG. 33) comprises a computer storing a drug master table. For example, the control console 609 may comprise a laptop personal computer or a desktop personal computer. The control console 609 broadcasts the drug ejection instruction prepared in an electronic message format to the tablet packing machines 610 via a suitable communication adapter. The drug master table (see FIG. 34A) comprises a large number of records searchable using drug codes as primary keys. Each record includes drug information such as drug name and dosage form. The drug master table also includes items such as: "machine ID" for identifying the tablet packing machine 610; "check data" assigned to each base unit 630 and checked against cassette identification information attached to the drug cassette 620; "feeder storage address" described above comprising a column address, a row address and a board address; and "cassette state" indicating whether the cassette is attached and whether the cassette is operable. A free area for future expansion that remains cleared to zero and unused for future expansion of functions is reserved.

In order to cause the associated drug feeder 613 to eject associated drugs, an electronic message for a drug ejection instruction transmitted from the control console 609 to the tablet packing machine 610 (see FIG. 34B) includes the number of drugs designated by a prescription, the machine ID that identifies the tablet packing machine 610 (identified by one of integers 1-N) and the aforementioned feeder storage address (a drug feeder storage address related to the drug feeder storage) that identifies the drug feeder 613 in the tablet packing machine 610 are also included in the electronic message to designate the destination of the message.

For reception of the drug ejection instruction, an internal communication means 660 of the tablet packing machine 610 is extended outside so as to be connected to a communication adapter of the control console 609 (see FIG. 33). For example, the internal communication means 660 is a LAN conforming to the IEEE RS485 standard. The controller 618 is connected to the LAN. Also connected to the LAN via the intra-rack wiring 662 are the rack control circuit 661, which controls the drug feeders 613, and a manual dispensing control circuit 664, which controls the operation of the manual dispensing unit 610a. The rack control circuit 661 is provided for each rack inside the drug storage 611. Therefore, there are multiple rack control circuits 661 in each tablet packing machine 610.

In the related-art tablet packing machine, the manual dispensing unit is used to automatically pack drugs not accommodated in the drug storage. The manual dispensing operation should best be avoided as it is cumbersome and time-consuming. In one approach to reduce the frequency of manual dispensing operations, several drug cassettes for respective drug types may be prepared outside the drug storage so as to accommodate drugs which would have been dispensed manually in the related art. Such a drug cassette may be attached to the base unit of the tablet packing machine as the need arises to replace the existing drug cassette. Unlike the drug cassette (drug feeder) described above characterized by frequent use, such a drug cassette (drug feeder) is characterized by higher frequency of replacement at the base unit than the frequency of use. Therefore, top priority is given to a feature that enables easy and accurate replacement of the drug cassette at the base unit, or easy and accurate updating of the correspondence between the base unit and the drug cassette (hereinafter, such a feature will be referred to as interchangeability in this specification).

Accordingly, an important technical goal to be achieved is to ensure that safety and interchangeability based on drug cassette matching are achieved in a compatible manner and to facilitate automatic packing of drugs not accommodated in the drug storage in a manner that minimizes sacrifice of the performance of the machine and the compatibility of the machine with an existing system.

A summary of the fourth embodiment will be given.

(1) An automatic dispenser according to the fourth embodiment comprises: a drug cassette which ejectably accommodates drugs; a base unit which detachably supports the drug cassette and drives a motor to eject drugs; a drug feeder storage which accommodates a large number of base units; a reading device which is provided in each of the base units and reads identification information assigned to the drug cassette; a checking means which compares a result of reading with pre-stored check data; and a drug dispensing controller which prepares a drug ejection instruction by referring to prescription data or drug dispensing data derived therefrom and which uses the instruction for motor-driven ejection by the base unit, wherein the base units are classified in a first group comprising a relatively large number of base units and a second group comprising a relatively smaller number of base units, and wherein the drug dispensing controller preparing the drug ejection instruction includes, in the drug ejection instruction addressed to the first group, a drug feeder storage address related to the drug feeder storage, and includes, in the drug ejection instruction addressed to the second group, the check data.

(2) The automatic drug dispenser of (1) according to the fourth embodiment may further be characterized in that a set of a microprocessor and a memory, or a microprocessor with a built-in memory is mounted in each of the base units, and the checking means and the check data are built in each microprocessor in a distributed manner, wherein the microprocessor mounted in the base unit of the second group is provided with and activates a built-in overwriting means which overwrites the check data with the identification information read by the reading device, and the microprocessor mounted in the base unit of the first group is not provided with an overwriting means or does not activate the overwriting means.

(3) The automatic drug dispenser of (1) or (2) according to the fourth embodiment is characterized in that each base unit is provided with a lighted indicator, wherein, when lighting a desired indicator, several neighboring indicators are also lighted.

In the automatic drug dispenser of (1), the electronic message for the drug ejection instruction addressed to the base of the first group includes a drug feeder storage address as a destination, and the electronic message for the drug ejection instruction addressed to the base unit of the second group includes the check data as a destination. By categorizing those drug feeders which are frequently used and in which safety based on drug cassette matching is given top priority in the first group and categorizing the drug feeder interchangeability based on drug cassette matching is given top priority in the second group, safety based on drug cassette matching and interchangeability are achieved in a compatible manner.

Since the feeder storage address is used for ejection of a large majority of drugs, the performance of the machine is only slightly impaired. The embodiment is implemented by partially modifying or expanding the system using the feeder storage address. Therefore, compatibility with an existing system is easily ensured.

Thus, according to the embodiment, it is possible to implement an automatic drug dispenser in which automatic packing of drugs not accommodated in the drug storage is facilitated, in a manner that give top priority to safety and interchangeability based on drug cassette matching and minimizes sacrifice of the performance of the machine and the compatibility of the machine with an existing system.

In the automatic drug dispenser of (2), distributed microprocessor arrangement not only enables the base unit of each drug feeder to execute the checking function but also is functionally expanded to the overwriting means for overwriting the check data. Accordingly, the base unit of each drug feeder is not only capable of executing the checking function but also updating the identification used in checking. This will further improve the interchangeability of the drug feeder of the second group which receives an electronic message including the matching data as a destination and ejects drugs accordingly. The overwriting means is built in only those microprocessors provided in the drug feeder belonging to the second group in which interchangeability is given top priority. A large majority of drug feeders belonging to the first group in which safety is given top priority are not affected. Safety is maintained as they receive an electronic message including the feeder storage address as a destination and eject drugs accordingly.

In the automatic drug dispenser of (3), by lighting not only the indicator provided in a desired based unit but also several neighboring indicators for guidance on a destination base unit to which the drug cassette should be attached, the guidance is made more visible, helping a user to find the destination of cassette attachment easily.

Figure 30:
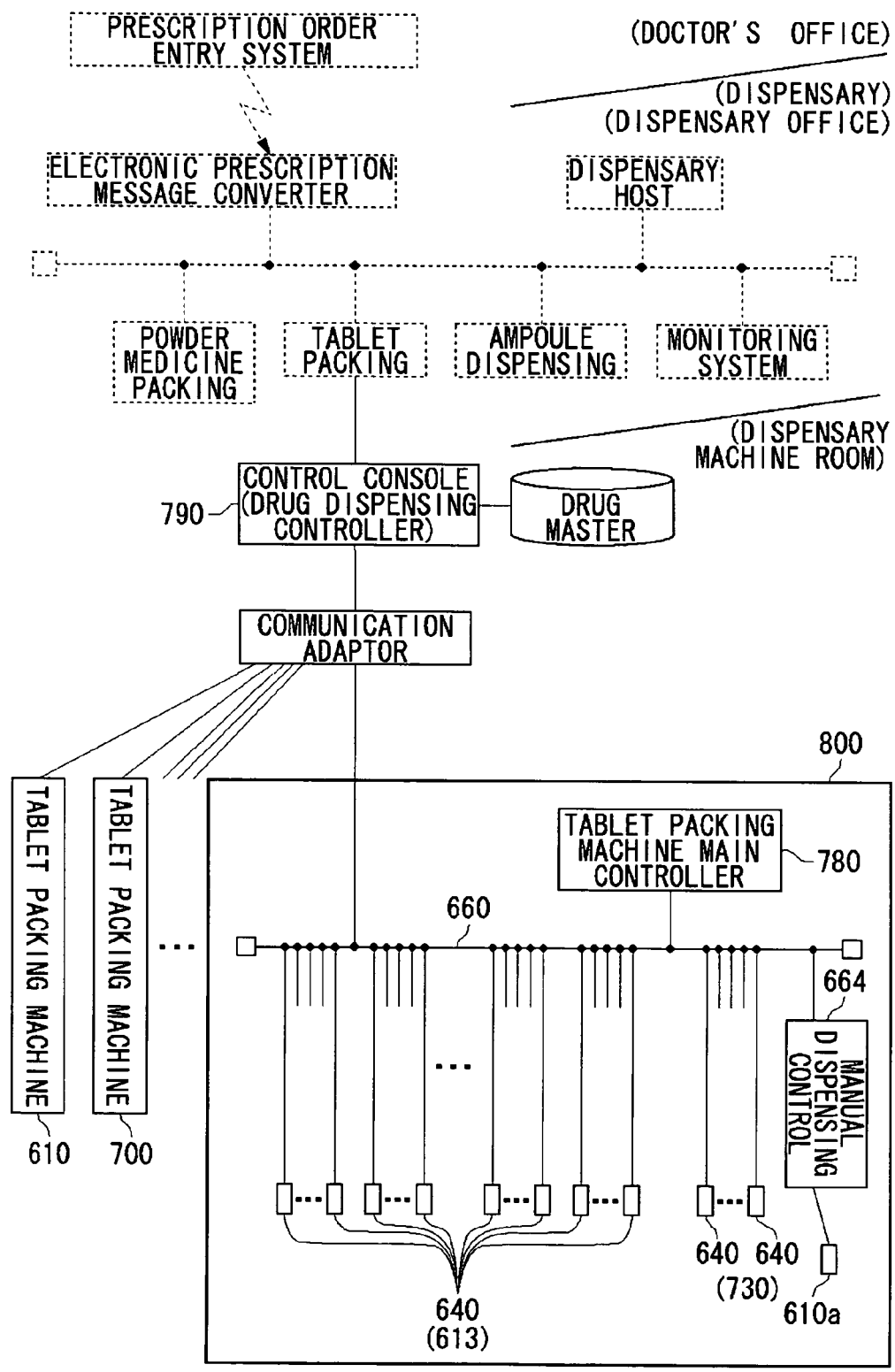
FIG. 30 is a block diagram showing the overall structure of a control system according to the fourth embodiment-2.
Figure 31A:
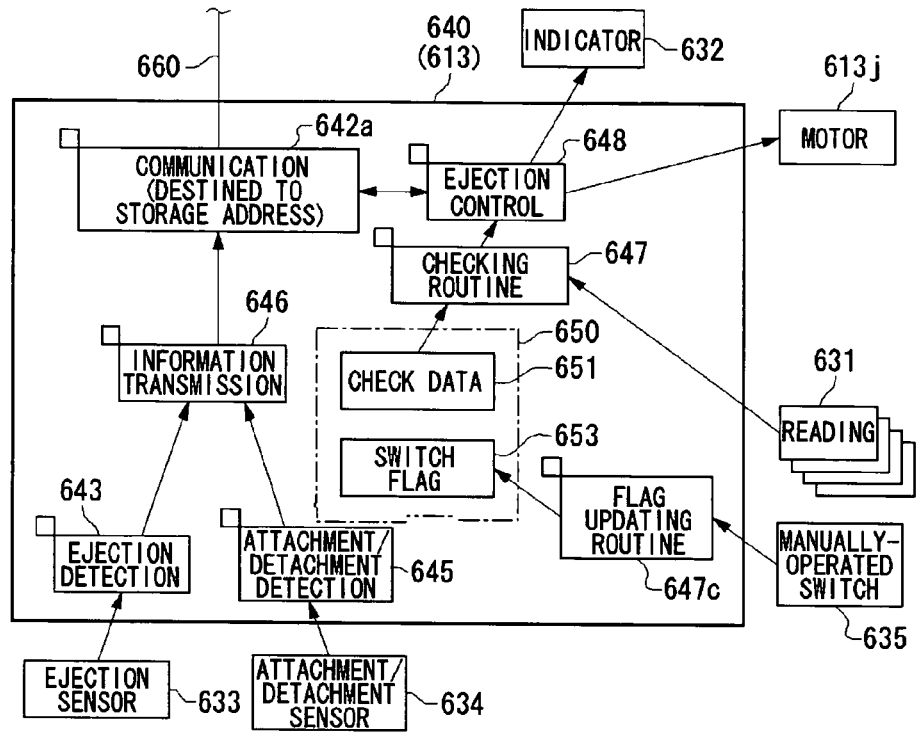
FIG. 31A is a functional block diagram of the microprocessor of the first group.
Figure 31B:
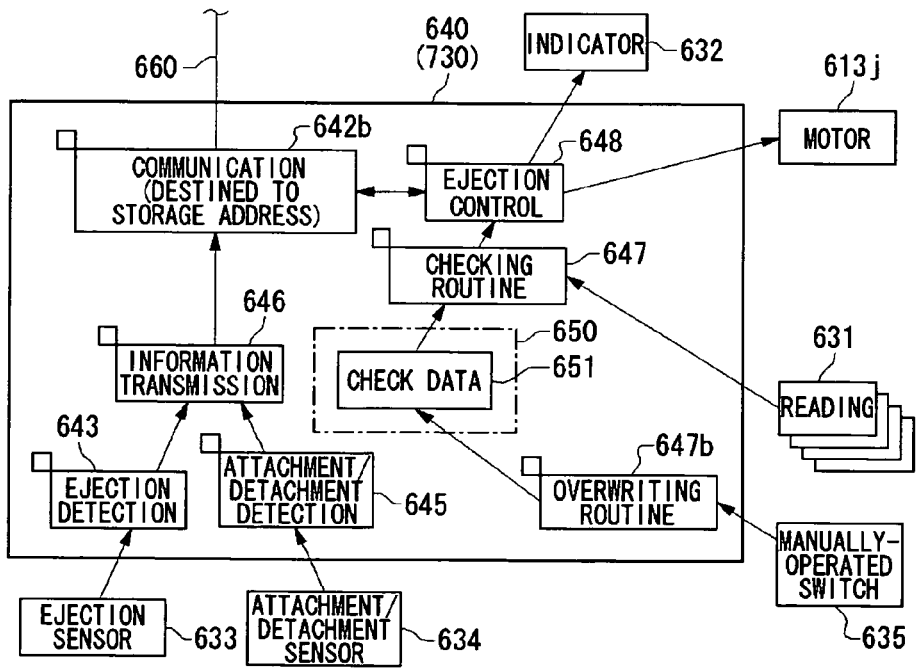
FIG. 31B is a functional block diagram of the microprocessor of the second group.

Specific embodiments of the drug feeder and automatic dispenser of the fourth embodiment will be described below by explaining the fourth embodiment-1 and the fourth embodiment-2. The fourth embodiment-1 shown in FIGS. 24A through 29G is an embodiment of all the features (1) through (3) above. The fourth embodiment-2 shown in FIGS. 30-31B is a variation thereof.

For brevity, fastening members such as bolts, joint members such as hinges, passage opening/closing members such as shutters, detailed circuit features such as motor drivers are omitted from the illustration. Those elements that are required in the invention and elements related thereto are mainly illustrated. Those constituting elements that are similar to the corresponding elements in the related art are designated by the same reference numerals. The following description mainly concerns a difference from the related art.

Fourth Embodiment-1

Figure 24A:
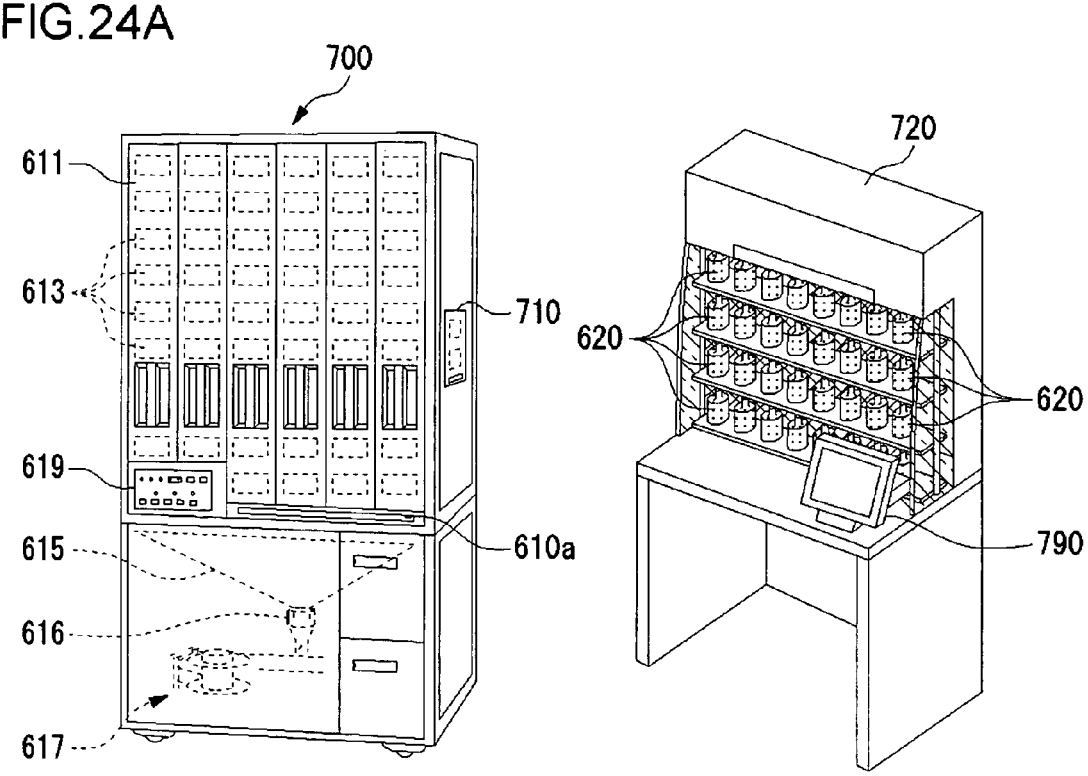
FIG. 24A is a perspective view of an automatic drug dispenser according to a fourth embodiment of the present invention.
Figure 24B:
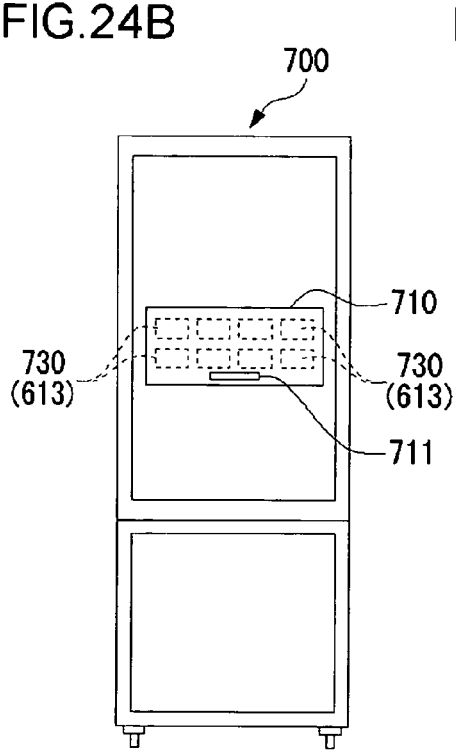
FIG. 24B is a right side view of a tablet packing machine according to the fourth embodiment.
Figure 24C:
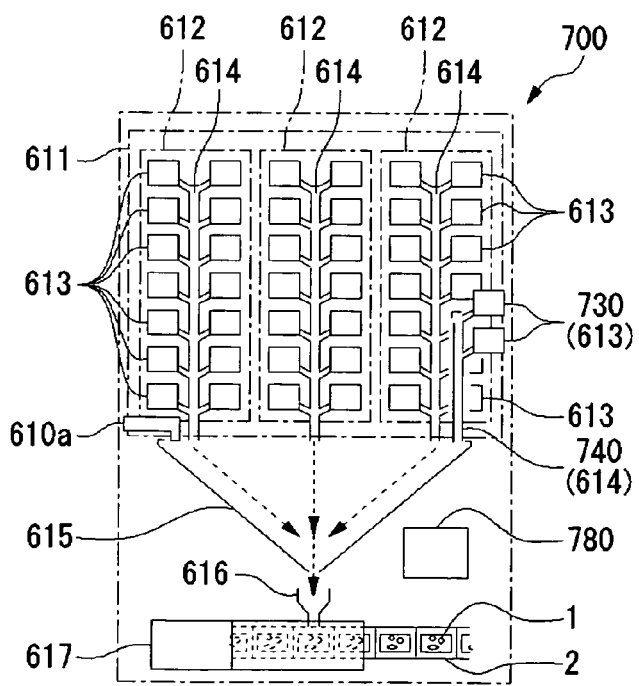
FIG. 24C shows the internal structure of the tablet packing machine according to the fourth embodiment.
Figure 25A:
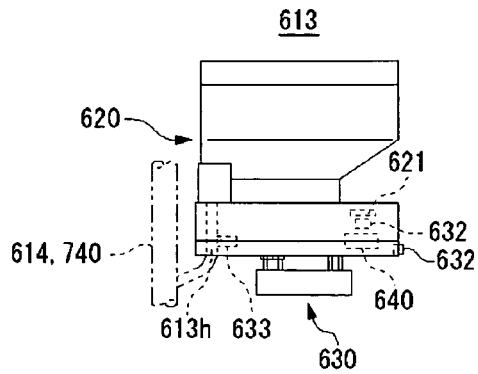
FIG. 25A is a left side view of a drug feeder according to the fourth embodiment.
Figure 25B:
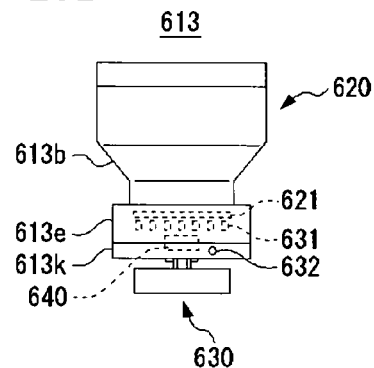
FIG. 25B is a front view of the drug feeder according to the fourth embodiment.
Figure 25C:
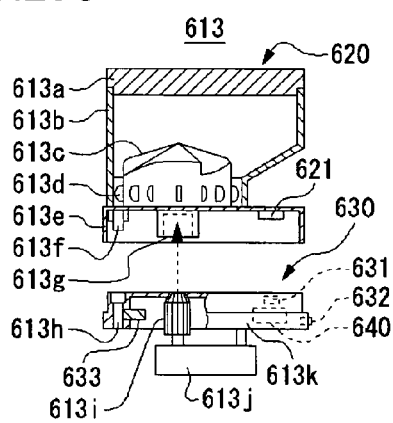
FIG. 25C is a longitudinal sectional view showing the left side of the drug feeder according to the fourth embodiment.
Figure 25D:
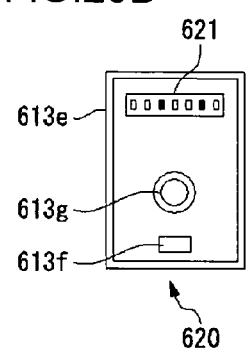
FIG. 25D is a bottom view of a drug cassette according to the fourth embodiment.
Figure 25E:
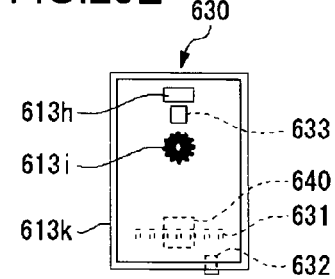
FIG. 25E is a top view of a base unit according to the fourth embodiment.
Figure 25F:
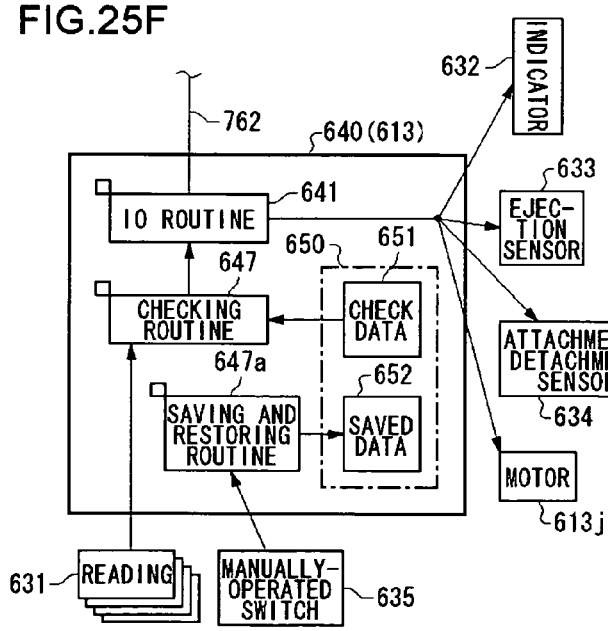
FIG. 25F is a functional block diagram of the microprocessor provided in each of a large number base units belonging to a first group.
Figure 25G:
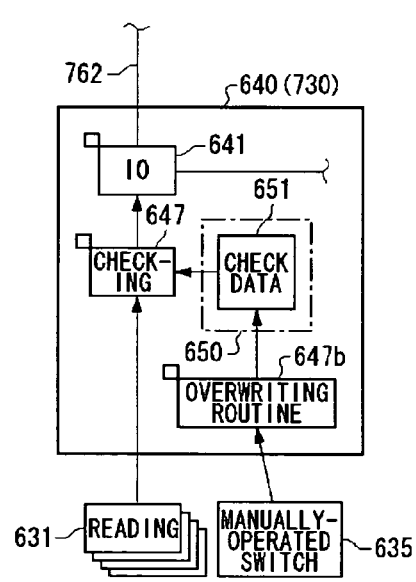
FIG. 25G is a functional block diagram of the microprocessor provided in a smaller number of base units belonging to a second group.

A description will now be given of the specific structure of the drug feeder and automatic drug dispenser according to the fourth embodiment-1 with reference to the drawings. FIGS. 24A-24C show the overall mechanical structure of the automatic drug dispenser. FIG. 24A is a perspective view; FIG. 24B is a right side view of a tablet packing machine 700; and FIG. 24C shows the internal structure of the tablet packing machine 700. FIGS. 25A-25G show the structure of each of a large number of drug feeders 613 and 730 built in the tablet packing machine 700. FIG. 25A is a left side view of the drug feeder; FIG. 25B is a front view of the drug feeder; FIG. 25C is a longitudinal sectional view showing the left side of the drug feeder; FIG. 25D is a bottom view of the drug cassette 620; FIG. 25E is a top view of the base unit 630; FIGS. 25F and 25G are block diagrams showing the primary functions of a microprocessor 640 provided in each of the base units 630 in a distributed fashion.

Figure 26:
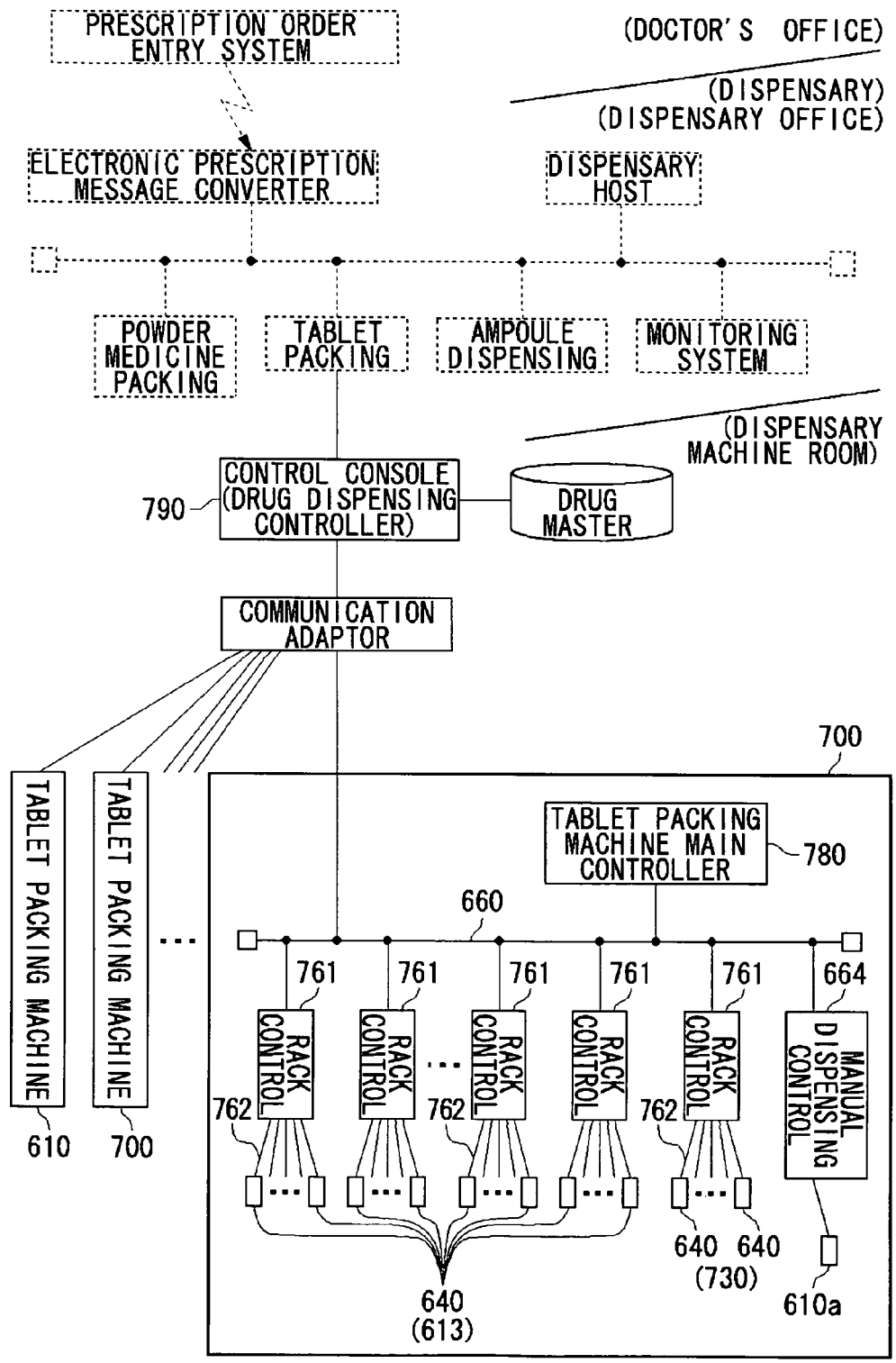
FIG. 26 is a block diagram showing the overall structure of a control system of the automatic drug dispenser.
Figure 28:
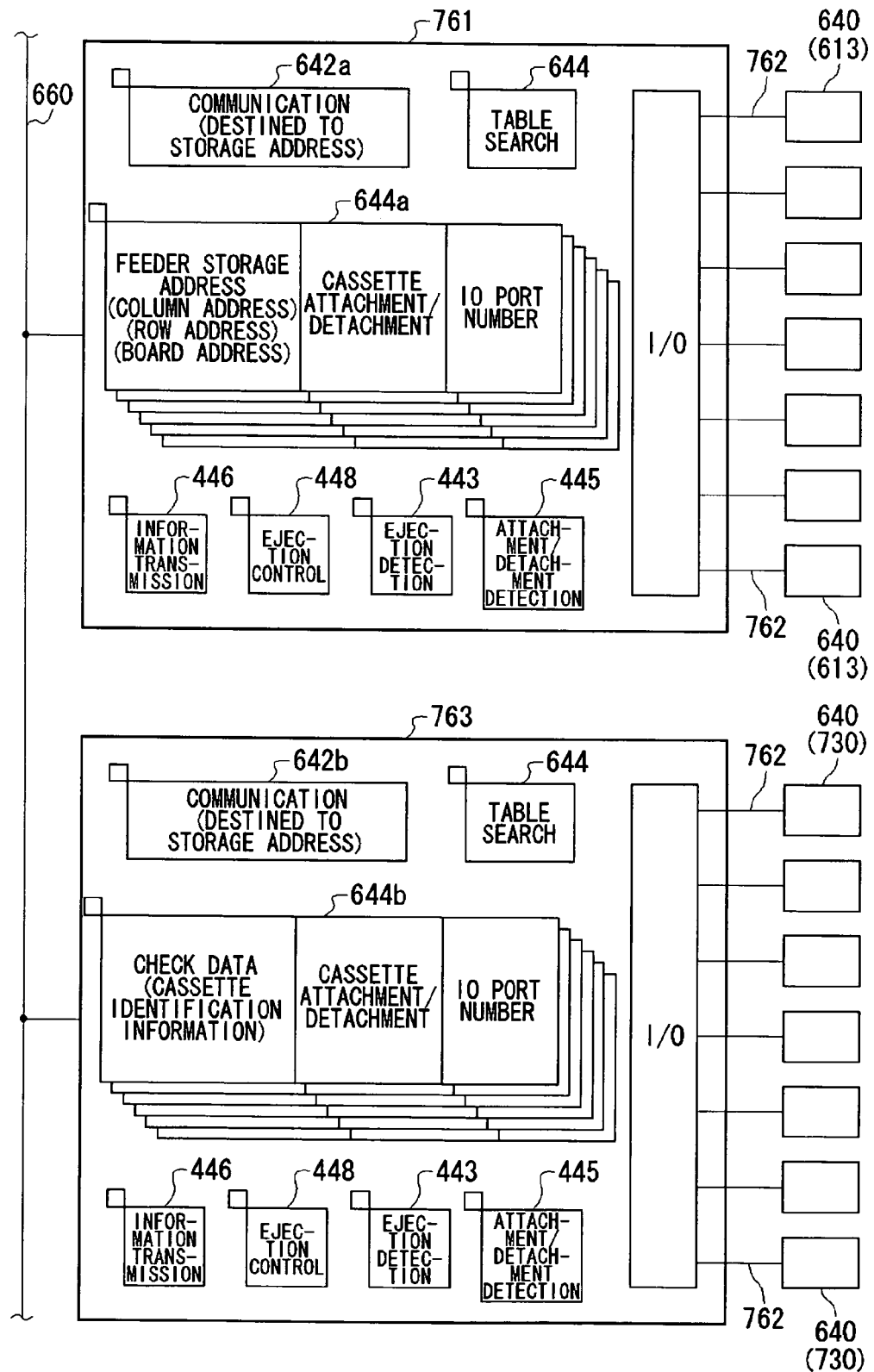
FIG. 28 is a functional block diagram of a tablet packing machine sub-controller in a control system.

More specifically, FIG. 25F is a functional block diagram of the microprocessor provided in each of a large number base units 630 belonging to the first group (i.e. the base unit 630 of the drug feeder 613 in the drug storage 611). FIG. 25G is a functional block diagram of the microprocessor 640 provided in each of a smaller number of base units 630 belonging to the second group (i.e. the base unit 630 of the drug feeder 730 in a feeder storage with cassette interchangeability 710). FIG. 26 is a block diagram showing the overall structure of the control system of the automatic drug dispenser; and FIGS. 27A through 27C show the structure of control data. FIG. 27A shows the structure of a record in a drug master table; and FIGS. 27B and 27C show the structure of an electronic message for an instruction for ejecting drugs. FIG. 27B shows an instruction addressed to the first group and includes the drug feeder storage address. FIG. 27C shows an instruction addressed to the second group and includes the check data. FIG. 28 is a functional block diagram of rack control circuits 761 and 763 (tablet packing machine sub-controller) in the control system.

Differences between the automatic drug dispenser of the fourth embodiment-1 and other automatic drug dispensers are that: a feeder storage with cassette interchangeability 710 and a stock rack 720 are added in the tablet packing machine 700, that the microprocessor 640 is mounted in the base unit 630 of each drug feeder 613, that the checking means and the check data are built in each microprocessor 640 in a distributed manner, and that a control console 790 (drug dispensing controller) is partially expanded in its functions to adapt to the grouping of the base units 630 of the drug feeders 613. In association with these features, the rack control circuit 661 is partially remodeled, resulting in the rack control circuit 761. Further, a new rack control circuit 763 is introduced. The controller 618 is partially remodeled so as to adapt to the grouping, resulting in a controller 780.

Features that are introduced in the tablet packing machine 700 will be described with reference to FIGS. 24A-24C. The feeder storage with cassette interchangeability 710 is built in an window opening formed on the right side of the drug storage 611. Normally, the opening is closed by a transparent door. As a user grips a door handle 711 to lift the transparent door, the opening is exposed so that the drug cassette 620 is introduced into or retrieved from the feeder storage with cassette interchangeability 710. The drug feeder storage 612 stores as many as several hundred drug feeders 613. In contrast, the feeder storage with cassette interchangeability 710 stores a smaller number of (for example, several tens of) drug feeders 730. The base unit 630 of each of a relatively large number of drug feeders 613 mounted in the drug feeder storage 612 is classified in the first group. The base unit 630 of each of a relatively smaller number of drug feeders 730 mounted in the feeder storage with cassette interchangeability 710 is classified in the second group.

The mechanical structure and basic function of the drug feeder 730 are the same as those of the drug feeder 613. Therefore, the drug feeder will be generically referred to using a reference numeral "613" where distinction is not necessary. Where distinction is necessary, reference numerals "613" and "730" will be used. The drug feeder 730 is provided with the drug cassette 620 which ejectably accommodates drugs and the base unit 630 which detachably supports the drug cassette 620 and drives a motor to eject the drugs. In accordance with an instruction for ejecting drugs from the control console 790, a designated number of drugs 1 are ejected from the drug cassette 620 so that the ejected drugs fall to the collecting member 615 via a conduit pipe 740 similar to the conduit pipe 614. A difference between the drug feeder 613 and the drug feeder 730 consists in an additional program related to the checking function, as described later.

The stock rack 720 is a simple rack separate from the tablet packing machine 700 and is capable of stocking a large number of (for example, several tens to several hundreds of) drug cassettes 620. The drug cassettes 620 are attached for use to the base unit 630 mounted in the feeder storage with cassette interchangeability 710. The drug cassettes 620 stocked in the stock rack 720 belong to the second group in the sense that they constitute the drug feeders 730 of the second group as they are mounted in the base unit 630. When removed from the base unit 630, the drug cassettes 620 are stocked in the stock rack 720 and are reserved for use. For this reason, the number of drug cassettes 620 in the second group is larger than the number of base units 630 if the stock rack 720 is taken into consideration in addition to the feeder storage with cassette interchangeability 710. In contrast, in the first group, the number of drug cassettes 620 accommodated in the drug storage 611 is equal to or smaller than the number of base units 630. The stock rack 720 may or may not serve as a workbench or a table on which to place the control console 790. The stock rack 720 may be provided in one-to-one relationship with the tablet packing machine 700. Alternatively, a smaller number of or a larger number of it may be provided than the number of tablet packing machines 700.

The drug feeders 613 and 730 each comprises the drug cassette 620, which is detachable, and the base unit 630, which is fixed (see FIGS. 25A through 25G). A detailed description of these components will be given, duplicating the description already given as necessary.

The drug cassette 620 is configured such that a container unit 613b with a lid 613a (a cup, a drug containing unit, a drug container) and an aligner 613c (a rotor, an aligning member, an ejection member), which has partition walls 613d (molded blades, blade-like projections, aligning members) provided at the circumference of the board, are secured to a casing board 613e (joint unit for attachment and detachment). When the aligner 613c is rotated via a cylindrical unit 613g (detachable power transmitting member), the drugs 1 inside the container unit 613b enter a space between the partition walls 613d one after another so as to be aligned. The drugs 1 then fall down one by one through an ejection outlet 613f.

The base unit 630 is provided with a base 613k (basic securing member) fitted to the drug feeder storage 612, a motor 613j (actuator) fixed to the base 613k, a spline shaft 613i (detachable power transmitting member) joined to the rotating shaft of the motor 613j. In order to facilitate the attachment and detachment of the drug cassette 620, the base unit 630 is configured such that the spline shaft 613i is engaged with the cylindrical unit 613g as the cassette is attached so that, in the engaged state, the rotation of the motor 613j is transmitted to the cylindrical unit 613g via the spline shaft 613i. A through hole 613h (drug falling passage) is formed in the base 613k so as to communicate with the ejection outlet 13f when the drug cassette 620 is attached to the base unit 630.

In the tablet packing machine 700 in which a large number of base units 630 such as described above are provided (see FIG. 24C), the conduit pipe 614 is built in the drug feeder storage 612 so as to extend vertically, and the conduit pipe 740 is built in the drug feeder storage with cassette interchangeability 710 so as to extend vertically. The ejection outlet 613f of the drug feeder 613, 730 communicates with the nearby conduit pipe 614, 740 via the through hole 613h of the base 613k and a extension pipe appropriately provided. The drug 1 ejected from the drug feeder 613, 730 is respectively led to the conduit pipe 614, 740 via the through hole 613h and then guided to the collecting member 615 after a free fall through the conduit pipe 614, 740. The collecting member 615 is built in the tablet packing machine at a location below the drug storage 611 and above the packaging apparatus 617. The upper-end opening thereof opens wide enough to cover the lower ends of all conduit pipes 614, while the lower-end opening thereof is narrowed down toward the drug input unit 616 of the packaging apparatus 617. The drugs 1 guided by the conduit pipes 614 and 740 are collected toward the lower-end opening before being forwarded to the packaging apparatus 617.

Shutter members (not shown) for temporarily retaining falling drugs are built in the conduit pipes 614 and 740, and in the drug collecting channels in the drug collecting mechanism 615. The drugs 1 to be packed together after being ejected from associated drug feeders 613 and 730 can be timed to fall to the collecting mechanism 415 simultaneously via the conduit pipes 614 and 740 or can be timed to be input to the drug input unit 616 of the packaging apparatus 617 simultaneously via an outlet at the lower end of the collecting mechanism 615. The drugs 1 passing through the drug collecting channel are packed in the packing strip 2 by the packaging apparatus 617. The packaging apparatus 617 feeds the packing strip 2 a predetermined length at a time and packs the drugs by heat sealing the strip. Thus, the drugs are automatically packed such that the drugs 1 are fed from associated drug feeders 613 to the packaging apparatus 617 via the collecting mechanisms 614 and 615 one by one or in units of multiple tablets.

Each of the drug feeders 613 and 730 is also provided with a checking means for reading and checking identification information in order to verify whether the drug cassette 620 attached to the base unit 630 is proper (see FIGS. 25A through 25G). More specifically, the drug cassette 620 is provided with an identification information bearing member 621 for holding identification information. The base unit 630 is provided with a reading device 631 for reading identification information from the identification information bearing member 621 and a microprocessor 640 of a one-chip type provided with a built-in memory. The identification information bearing member 621 is a sticker with a scanned surface on which, for example, a total of eleven white or black marks are arranged in a single row. The sticker is pasted to the underside of the drug cassette 620. The reading device 631 is configured such that as many reflective photosensors as the number of marks on the identification information bearing member 621 are also arranged in a single row. The reading device 631 is provided on top of the base unit 630. In a state in which the drug cassette 620 is attached to the base unit 630, the reading device 631 and the identification information bearing member 621 are opposite to each other to facilitate reading.

To allow each of the drug feeders 613 and 730 or, more specifically, the base unit 630, to check the identification information by using the result of reading by the reading device 631, the reading device 631 is connected to the microprocessor 640. A memory 650 in the microprocessor 640 stores check data 651. The microprocessor 640 has a checking routine 647 installed therein to check the result of reading by the reading device 631 against the check data 651 (see FIGS. 25F and 25G). Also installed in the microprocessor 640 is an I/O routine 641 for signal exchange with the rack control circuits 761 and 763 via an intra-rack wiring 662, an expansion of the intra-rack wiring 662.

Further, the base unit 630 is provided with lighted a indicator 632 (for example, a green LED) for easy visual identification (see FIG. 25E). In the base unit 630 of the drug feeder 613 of the first group, the indicator 632 is used to show a communication enabled state or drug ejection disabled state. In the base unit 630 of the drug feeder 730 of the second group, the indicator 632 is used to provide guidance on the location of attachment of the replacement drug cassette 620. In the illustration, only one indicator 632 is provided in the base unit 630. Alternatively, the base unit 630 may be provided with multiple indicators 632 of different colors that are suitably used depending on the required function. Also provided in the base unit 630 are an ejection sensor 633 for detecting the drug 1 as it passes the through hole 613h, and an attachment/detachment sensor 634, such as a mechanical switch, for detecting whether the drug cassette 620 is attached to the base unit 630. A manually-operated switch 635 operated to activate the expanded function of the checking function is also provided where it is concealed in a small hole or the like.

These components (632, 633, 634, 635) are also connected to the microprocessor 640 and are subject to its control, similar to the reading device 631 and the motor 613j. The indicator 632, the ejection sensor 633, the attachment/detachment sensor 634 and the motor 613j are connected to the rack control circuits 761 and 763 via the microprocessor 640 as well as via the intra-rack wiring 762. Signal transfer processing by the I/O routine 641 enables the indicator 432, the ejection sensor 633, the attachment/detachment sensor 634 and the motor 613j to be subject to the control of the rack control circuits 761 and 763 by allowing these components to exchange signals with the rack control circuits 761 and 763, in substantially the same manner as when the components are directly controlled by the rack control circuit 661 via the intra-rack wiring 662. The result of reading by the reading device 631 is delivered to the checking routine 647 described above. The operational status of the manually-operated switch 635 is delivered to a saving and restoring routine 647a and an overwriting routine 647b described later.

To describe the function of the microprocessor 640 in detail (see FIGS. 25F and 25G), the checking routine 647 compares the check data 651 stored in the memory with the result of reading by the reading device 631 at the time of attaching the drug cassette 620 to the base unit 630 of the drug feeder 613 or the drug feeder 530 and, optionally, at an appropriate point of time during an operation for attaching the cassette as well. The check data 651 is formed, for example, as 11-bit data, like the marks on the identification information bearing member 621, so that it is immediately known whether or not the data matches the result of reading by the reading device 631 by comparison. If the result of comparison indicates matching failure, the checking routine 647 sends out an associated signal to the rack control circuits 761 and 763 via the I/O routine 641 and the intra-wiring 762 in order to suspend motor-driven ejection by the associated base unit 630. If the result of scanning the identification information bearing member 621 and the check data 651 in the memory 650 match, the checking routine 647 sends out an associated signal to the rack control circuits 761 and 763 via the I/O routine 641 and the intra-rack wiring 762 so as to enable motor-driven ejection by the associated base unit 630.

The check data 651 is written in the memory 650 using a writing tool such as a general-purpose ROM writer or a dedicated writer. The stand-alone memory 650 may be temporarily installed in the tool to write specified data in a specified address. It is also possible to download the check data registered in the drug master table of the control console 790 to the microprocessor 640. In the case of the drug feeder 730 belonging to the second group in which top priority is given to interchangeability, it is convenient and error free to transfer to the memory 650 the identification information of the drug cassette 620 as it is attached to the base unit 630. Therefore, in addition to the checking routine 647, the overwriting routine 647b is installed in the microprocessor 640 of the base unit 630 of the drug feeder 730 (see FIG. 25G). When the manually-operated switch 635 is operated, the program allows the reading device 631 to read the identification information from the identification information bearing member 621 of the drug cassette 620 currently attached to the base unit 630 so that the check data 651 is overwritten with the identification information thus read.

In contrast, in the case of the drug feeder 613 belonging to the first group in which top priority is given to safety, the saving and restoring routine 647a for suspending the function of the checking means is installed in the microprocessor 640 of the base unit 630, in addition to the checking routine 647 (see FIG. 25F). An area used by the saving and restoring routine 647a to store saved data 652 is reserved in the memory 650. When the manually-operated switch 635 is operated, the saving and restoring routine 647a transfers current values of the check data 651 as the saved data 652 and then clears the check data 651 to zero. When the manually-operated switch 635 is operated a second time, the saving and restoring routine 647 overwrites the check data 651 with the values saved as the saved data 652. In association with this, the checking routine 647 does not perform a comparing process and a checking process while the check data 651 is cleared to zero.

Thus, in the tablet packing machine 700, in addition to the checking means, the check bypassing means is operably built in those of the microprocessors 640 respectively attached to a large number of base units 630 that are classified in the first group. The overwriting means is not built in the microprocessors 640 of this group. The overwriting means, in addition to the checking means, is operably built in those of the microprocessors 640 of the second group. The check bypassing means is not provided in the microprocessors 640 of this group. The check bypassing means includes means to save and restore the check data. The overwriting means overwrites the check data with the identification information read by the reading device.

The control console 790 (see FIG. 26) uses different drug ejection instructions depending on the grouping of the base unit 630. The functions of the control console 790 are expanded so as to be capable of integrally managing a mixed system in which the tablet packing machine 700 and the tablet packing machine 610 already described are colocated. More specifically, an "AC flag", an item of expanded functions, is assigned to a portion of the free area reserved for future expansion in each record in the drug master table. If the associated drug cassette 620 is for the drug feeder 613 of the first group, the AC flag is turned off. If the associated drug cassette 620 is for the drug feeder 730 of the second group, the AC flag is turned on (see FIG. 27A). The drug master table is expanded by a table editing program or the like as part of the initialization of the tablet packing machine 700 newly installed. The AC flag when turned off is designed to be of the same value occurring when the free area reserved for future expansion is cleared to zero so that table updating can be omitted in the existing tablet packing machine 710.

When creating a drug ejection instruction addressed to the drug feeder 613 of the first group, the control console 790 includes in the instruction the feeder storage address (the drug feeder storage address related to the drug feeder storage) retrieved from the drug master table, as is similarly done by the control console 609. The control console 790 further appends the AC flag turned off to the instruction (see FIG. 27B). A difference from the control console 609 is that, when creating a drug ejection instruction addressed to the drug feeder 730 of the second group, the control console 790 includes in the instruction the check data (data compared with the cassette identification information) retrieved from the drug master table, instead of the feeder storage address. The control console 790 further appends the AC flag turned on to the instruction.

Whether the drug cassette 620 belongs to the first group or the second group is determined by referring to the AC flag. While the contents of identification information assigned to the drug cassette 620 is not constrained by the grouping, it will be assumed here that values in the range between "1" and "500" are assigned to the first group and values in the range between "501" and "2000" are assigned to the second group, to facilitate checking of operations. The value "0" is not used as the identification information of the drug cassette 620 since it is also the value occurring when the check data 651 is cleared to zero to bypass the checking process. Although the majority of base units 630 are of the first group and there are smaller number of base units 630 of the second group, there may be a larger number of drug cassettes 620 of the second group than those of the first group because cassettes of the second group are used as replacements.

The rack control circuit 761 (see FIG. 28) also comprises a microprocessor or the like. A communication routine 642a as a means for communication, an ejection detecting routine 643 for detecting whether the drug is ejected or not, or whether the drug is ejected properly, a table search routine 644 for accessing a port table 644a, an attachment/detachment detecting routine 645 as a means for detecting whether the cassette is attached or detached, an information transmitting routine 646 as a transmitting means and an ejection control routine 648 as a means for motor-driven ejection control are installed in the rack control circuit 761 in order to control several to several tens of drug feeders 613 (the base units 630 of the first group) via the individual intra-rack wirings 762.

The communication routine 642a receives an instruction from the control console 790 or, in some cases, the controller 780 via the internal communication means 660 and also transmits status or data to the control console 790. Instructions received by the communication routine 642a include a drug ejection instruction and an information uploading instruction. A process involving the drug ejection instruction will be described in detail. Upon receipt of a drug ejection instruction, the communication routine 642a checks the AC flag included in the instruction. If the AC flag is turned on, the communication routine 642a disregards the instruction. If the AC flag is turned off, the communication routine 642a delivers the instruction to the table search routine 644.

The table search routine 644 retrieves a feeder storage address from the drug ejection instruction received from the communication routine 642a and searches the port table 644a using the retrieved address as a key. The number of valid records contained in the port table 644a is equal to the number of drug feeders 613 under the control of the rack control circuit 761. Each record includes items like a feeder storage address, status of cassette attachment/detachment and an I/O port number. By retrieving the I/O port number from a record in the port table 644a containing a feeder storage address that matches the address included in the drug ejection instruction, the table search routine 644 identifies the drug feeder 613 to be operated for drug ejection and, more specifically, the intra-rack wiring 762 and the microprocessor 640 at the destination of signal transmission. If the drug cassette 620 is attached to the identified drug feeder 613, the table search routine 644 delivers the drug ejection instruction to the ejection control routine 648. If not, the table search routine 644 causes the information transmitting routine 646 to notify the control console 790 of the detachment of the cassette.

The attachment/detachment detecting routine 645 monitors the status of attachment/detachment of the drug cassette 620 to the base unit 630 of the drug feeder 613. Each time the status changes, the attachment/detachment detecting routine 645 updates associated items in the port table 644a. More specifically, the attachment/detachment detecting routine 645 receives a detection output from the attachment/detachment sensor 634 of the base unit 630 of the drug feeder 613. By referring to a change in the detected value or by referring to a message signal output when the cassette is attached or detached, the attachment/detachment detecting routine 645 detects that the drug cassette 620 is attached to the base unit 630 or detached therefrom. The attachment/detachment detecting routine 645 writes associated information as an item in the port table 644a to indicate whether the cassette is attached or detached. In addition, the attachment/detachment detecting routine 645 causes the information transmitting routine 646 to notify the control console 790 of the status of cassette.

Upon receipt of the drug ejection instruction and the I/O port number from the table search routine 644, the ejection control routine 648 causes the motor 613j of the associated drug feeder 613 to be rotated via the intra-rack wiring 762 and the microprocessor 640 identified by the I/O port number. When the ejection sensor 633 detects that as many drugs 1 as designated by the drug ejection instruction have been ejected, the ejection control routine 648 suspends the rotation of the motor 613j. The result of detection by the ejection sensor 633 of the associated drug feeder 613 is input to the ejection detecting routine 643 via the microprocessor 640 provided in the base unit 630 and via the intra-rack wiring 762 connected to the microprocessor 640. The result of detection is then delivered from the ejection detection routine 643 to the ejection control routine 648. After the ejection control routine 648 is notified by the checking routine 647 of the microprocessor 640 of the drug feeder 613 of matching failure via the intra-rack wiring 762, the ejection control routine 648 suspends the rotation of the motor 613j even if it receives the drug ejection instruction. After the ejection control routine 648 is notified by the checking routine 647 that matching is established, the ejection control routine 648 resumes the rotation of the motor 613j in accordance with the drug ejection instruction.

Like the rack control circuit 761, the rack control circuit 763 (see FIG. 28) also comprises a microprocessor or the like. A communication routine 642b as a means for communication, an ejection detecting routine 643 for detecting whether the drug is ejected or not, or whether the drug is ejected properly, a table search routine 644 for accessing a port table 644b, an attachment/detachment detecting routine 645 as a means for detecting whether the cassette is attached or detached, an information transmitting routine 646 as a transmitting means and an ejection control routine 648 as a means for motor-driven ejection control are installed in the rack control circuit 763. Another point of similarity with the rack control circuit 761 is that the rack control circuit 763 is connected to several to several tens of microprocessors 640 under its control via the individual intra-rack wirings 762 to enable signal exchange. Unlike the rack control circuit 761, however, the drug feeder 730 (the base unit 630 of the second group) is subject to the control of the rack control circuit 763 and, therefore, the communication routine 642b and the port table 644b are partly different from the communication routine 642a and the port table 644a, respectively.

To be more specific, the communication routine 642b receives an instruction from the control console 790 or, in some cases, the controller 780 via the internal communication means 660 and also transmits status or data to the control console 790. Instructions received by the communication routine 642b include a drug ejection instruction and an information uploading instruction. As such, the communication routine 642b is similar to the communication routine 642a. However, the communication routine 642b processes the drug ejection instruction differently from the communication routine 642a. That is, upon receipt of a drug ejection instruction, the communication routine 642b checks the AC flag included in the instruction. If the AC flag is turned off, the communication routine 642b disregards the instruction. If the AC flag is turned on, the communication routine 642b delivers the instruction to the table search routine 644. With this, the drug ejection instruction is forwarded from the communication routines 642a and 642b to the drug feeder 613 of the first group or the drug feeder 630 of the second group, depending on whether the AC flag is turned on or off.

In agreement with the fact that the drug ejection instruction in which the AC flag is turned off contains check data instead of a feeder storage address as a destination of the instruction, each record in the port table 644b includes items like check data, status of cassette attachment/detachment and an I/O port number. The number of valid records contained in the port table 644b is equal to the number of drug feeders 730 (more specifically, the number of base units 630 of the second group) under the control of the rack control circuit 763.

The table search routine 644 retrieves the check data from the drug ejection instruction received from the communication routine 642b and searches the port table 644b using the retrieved data as a key.

If the search is successful and the I/O port number is retrieved from a record in the port table 644b containing the check data that matches the data included in the drug ejection instruction, the table search routine 644 identifies the drug feeder 730 (more specifically, the intra-rack wiring 762 and the microprocessor 640 at the destination of signal transmission) to be operated for drug ejection. If the drug cassette 620 is attached to the identified drug feeder 730, the table search routine 644 delivers the drug ejection instruction to the ejection control routine 648. If the drug cassette 620 is not attached to the identified drug feeder 730, the table search routine 644 lights the indicator 632 provided in the base unit 630 of the identified drug feeder 730 to provide guidance on a destination base to which a cassette should be attached. When the desired drug cassette 620 is attached, the table search routine 644 turns the indicator 632 off and delivers the drug ejection instruction to the ejection control routine 648.

If the search in the port table 644b fails, the table search routine 644 selects a record with the oldest update history in the port table 644b and updates that record by overwriting the check data in the record with the check data included in the drug ejection instruction. The table search routine 644 sends the check data to the microprocessor 640 of the base unit 630 of the drug feeder 730 identified by the I/O port number included in that record so as to update the check data 651 of the microprocessor 640. The table search routine 644 then lights the indicator 632 provided in the base unit 630 of the identified drug feeder 730 for guidance on a destination base to which a cassette should be attached. When the desired drug cassette 620 is attached or when the existing drug cassette 620 is replaced by the desired drug cassette 620, the table search routine 644 turns the indicator 632 off and delivers the drug ejection instruction to the ejection control routine 648.

When lighting a desired indicator 632 provided in the base units 630 for guidance on a destination base to which a cassette should be attached, the table search routine 644 is designed to also light several indicators 632 in the neighborhood to make the guidance more visible. A variety of lighting patterns may be available. In the illustrated example, the indicators 632 on the same rack are lighted all at once, whereupon the most distant indicator 632 is turned off, followed by the less distant indicators 632, until only the target indicator 632 is lighted. This pattern is repeated. The lighting for guidance on the destination of cassette attachment is important for the drug feeder 730 of the second drug feeder which is stored in the feeder storage with cassette interchangeability 710 and in which the interchangeability is given top priority. The guidance function is also useful in drug refilling of the drug feeder 613 of the first group which is stored in the drug feeder storage 612 and in which safety is given top priority. In prompting a user to attach or replace the drug cassette 620, the table search routine 644 not only lights the indicator 632 but also directs the information transmitting routine 646 to send an electronic message designating a request for lighting to the controller 780 or the control console 790.

The controller 780 (tablet packing machine main controller) monitors a drug ejection instruction issued from the control console 790. If the AC flag in the drug ejection instruction is turned off and the feeder storage address is included in the instruction as a destination, the controller 780, similarly to the controller 618, variably times the opening and closing of shutters in the drug collecting mechanisms 614 and 615 as well as timing the operation of the packaging apparatus 617, by estimating the time required for a drug to fall from the drug feeder 613 by referring to the column address in the drug feeder storage address. If the AC flag in the drug ejection instruction is turned on and the identification data, instead of the feeder storage address, is included in the instruction, the controller 780, unlike the controller 618, employs the longest time of drug fall from the base units 630 (i.e. the base unit 630 of the drug feeder 730 of the second group) stored in the feeder storage with cassette interchangeability 710, to estimate the time required for a drug to fall from the drug feeder 730.

The usage mode and the operation of the drug feeder and the automatic drug dispenser according to the fourth embodiment-1 will be described with reference to the drawings. FIGS. 29A-29G show an example of how the indicators in the feeder storage with cassette interchangeability are lighted, illustrating time-dependant change in lighted status.

When prescription data or drug dispensing data derived therefrom related to the tablet packing machine 610 or the tablet packing machine 700 under the control of the control console 790 are input to the control console 790, the control console 790 refers to the drug master table and prepares a drug ejection instruction and transmits the instruction to the tablet packing machine 610 or the tablet packing machine 700 via the internal communication means 660. If the drug ejection instruction is addressed to the tablet packing machine 610 or to the drug feeder 613 of the first group stored in the drug feeder storage 612 of the tablet packing machine 700, the drug ejection instruction according to the fourth embodiment-1 is the same as the instruction according to the other embodiments except that the AC flag appended is turned off. Drugs to be packed in accordance with such an instruction are normally accommodated in the drug storage 611 so that they can be automatically ejected. Therefore, automatic drug packing is performed in the tablet packing machine 700 as in the tablet packing machine 610.

That is, when the drug ejection instruction is transmitted from the control console 790 to the tablet packing machine 700, the drug ejection instruction is received by the rack control circuit 761 since the AC flag is turned off. The instruction is then used by the table search routine 644 to search the port table 644a. As a result of cooperation between the microprocessor 640 of the drug feeder 613 identified as a result of the search and the ejection control routine 648 of the rack control circuit 761, a designated number of drugs 1 are caused to fall from the drug feeder 613 for ejection. The drugs 1 are input to the drug input unit 616 of the packaging apparatus 617 via the drug collecting mechanisms 614 and 615 and are packed in the packing strip 2 by the packaging apparatus 617. In this process, the drug ejection instruction is monitored by the controller 780. The timing of the fall of the drug 1 and the timing of packing by the packaging apparatus 617 are optimally adjusted by controlling the opening and closing of shutters in accordance with the feeder storage address included in the drug ejection instruction as a destination.

If the drug cassette 620 of the drug feeder 613 to be operated for drug ejection is empty or not attached, the controller 780 or the control console 790 provides an alarm display prompting a user to refill the cassette with drugs or attach the cassette, by referring to the result of detection by the attachment/detachment detecting routine 645 or the like, or the status report provided by the information transmitting routine 646. When an operator attaches the proper drug cassette 620 to the base unit 630, the reading device 631 of the base unit 630 scans the identification information bearing member 621 of the drug cassette 620. The checking routine 647 compares the identification information with the check data 651 stored in the memory 650 of the microprocessor 640. If they do not match, the ejecting operation is suspended. Therefore, improper packing due to improper attachment of the drug cassette 620 is prevented.

In contrast, if the drug ejection instruction is addressed to the drug feeder 730 of the second group stored in the feeder storage with cassette interchangeability 710 of the tablet packing machine 700, the AC flag turned on is appended to the drug ejection instruction and the check data to be compared with the identification information of the drug cassette 620 is included in the instruction as a destination. In this case, when the drug ejection instruction is transmitted from the control console 790 to the tablet packing machine 700, the drug ejection instruction is received by the rack control circuit 763 since the AC flag is turned on. The instruction is then used by the table search routine 644 to search the port table 644b. If the drug cassette 620 bearing the identification information designated by the drug ejection instruction is attached to the base unit 630 of the drug feeder 730 identified as a result of the search, cooperation between the microprocessor 640 of the drug feeder 730 and the ejection control routine 648 of the rack control circuit 763 causes a designated number of drugs 1 to fall from the drug feeder 730 for ejection. Similarly to the case of the drug feeder 613, the drug 1 is input to the drug input unit 616 of the packing machine 617 via the drug collecting mechanisms 740 and 615 and is packed in the packing strip 2 by the packaging apparatus 617. The controller 780 adjusts the timing of fall and the timing of packing so as to be on the safer side, by using the longest time of drug fall from the drug feeders 730.

If the drug cassette 620 bearing the identification information that matches the check data included in the drug ejection instruction is not attached to any of the base units 630 in the feeder storage with cassette interchangeability 710, the controller 780 or the control console 790 provides an alarm display prompting a user to attach or replace the cassette 620, in accordance with the electronic message from the table search routine 644 of the rack control circuit 763. In parallel with this, the table search routine 644 of the rack control circuit 763 lights the indicator to provide guidance on the destination of cassette attachment. To describe the operation using a specific example (see FIGS. 29A through 29G), it will be assumed that eight identical drug feeders 730 are arranged on the same rack in the feeder storage with cassette interchangeability 710 and that a need arises to replace the drug cassette 620 at the fourth feeder from left (see where outlined arrow points in FIGS. 29A through 29G).

Figure 29A:
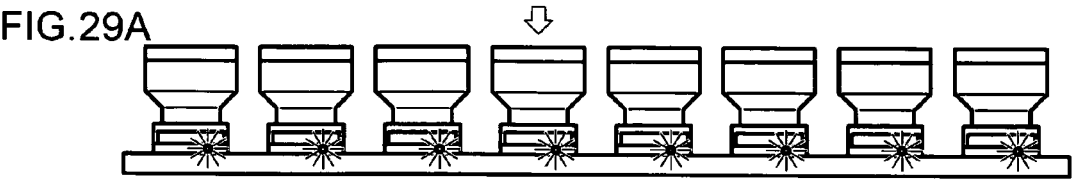
FIGS. 29A-29G show an example of how indicators in a feeder storage with cassette interchangeability are lighted.
Figure 29B:
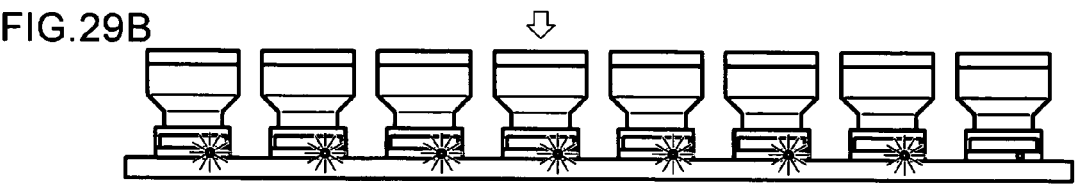
Figure 29C:
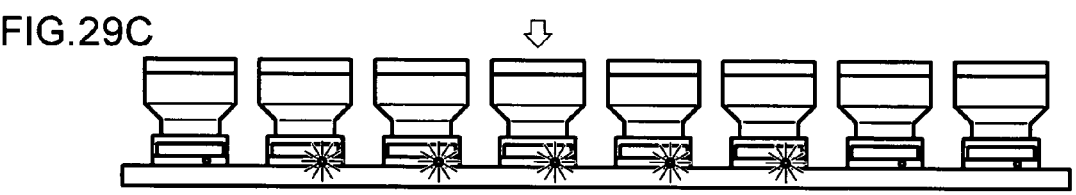
Figure 29D:
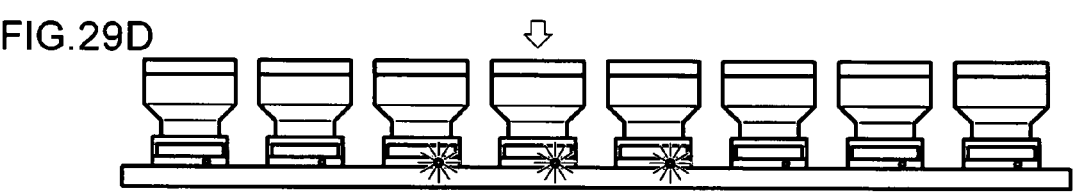
Figure 29E:
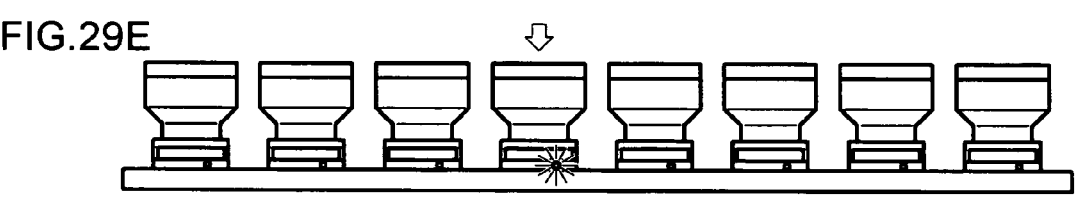
Figure 29F:
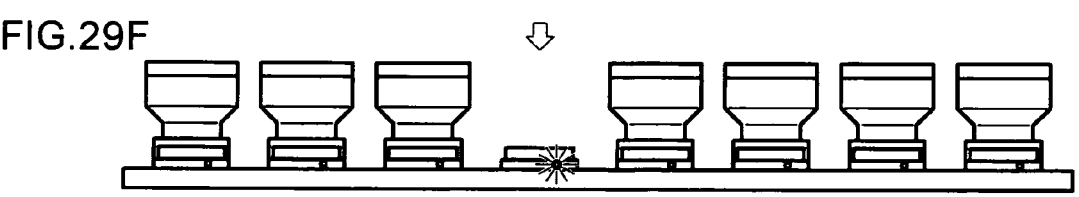

In this case, the indicators 632 of the base units 630 of the eight drug feeders 730 on the rack are lighted all at once (see FIG. 29A). After a certain interval, the indicator 632 at the right end is turned off (see FIG. 29B). After another interval, the leftmost indicator 632 and the seventh indicator 632 from left are turned off (see FIG. 29C). After yet another interval, the second and sixth indicators 632 from left are turned off (see FIG. 29D). After yet another interval, the third and fifth indicators 632 from left are turned off (see FIG. 29E). The fourth indicator 632 from left where replacement should take place continues to be lighted. Even when the undesired drug cassette 620 is removed (FIG. 29F), the lighting pattern, with a lighted range being progressively narrowed down until only the target indicator 632 is lighted, is repeated.

Figure 29G:
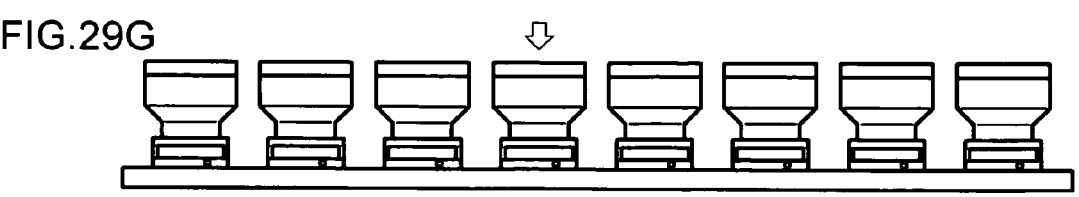

When the drug cassette 620 bearing the identification information that matches the check data included in the drug ejection instruction is taken out by operation personnel from the stock rack 720 and attached to the fourth base unit 630 from left where replacement should take place, all the indicators 632 are turned off (see FIG. 29G). When the manually-operated switch 635 at the base unit 630 is operated for confirmation, the overwriting routine 647b installed in the microprocessor 640 provided in the base unit 630 overwrites the check data 651. The rack control circuit 763 updates the item of check data in a corresponding record in the port table 644b by overwriting. Thus, a large number of drug cassettes 620 stocked in the stock rack 720 are also automatically set up for drug ejection. For drugs not accommodated not only in the drug feeder storage 612 or the feeder storage with cassette interchangeability 710 but also in the drug cassettes 620 in the stock rack 720, the manual dispensing unit 610a will continue to be used as in the other embodiments. The frequency of having to use the unit 610a, however, is quite low.

Given above is an explanation of a situation where automatic packing is properly performed. There are a large number of drug feeders 613 of the first group stored in the drug feeder storage 612 and, in addition, the drug type and dosage form come in a large variety. Thus, unexpected troubles may occur in some drug feeders 613 such as delay in feeding and cracking in a drug. Such trouble in drug ejection is likely to occur when the operation of a packing machine is initially started or when a new drug is introduced into the system. A trouble may occur during the operation. In such a case, the manually-operated switch 635 at the base unit 630 of the target drug feeder 613 is operated in order to manually determine whether the trouble occurred in the cassette 620 or the base unit 630, or whether the drug feeder 613 and the drug 1 are not compatible with each other.

When the manually-operated switch 635 is operated, the saving and restoring routine 647a of the microprocessor 640 saves the check data 651 as the saved data 652 and clears the check data 651 to zero. With this, the checking function of the checking routine 647 is suspended in the drug feeder 613 so that checking function in the drug cassette 620 is bypassed. The indicator 632 of the base unit 630 is lighted to indicate the source of the trouble. When the checking function in the drug cassette 620 is bypassed, the cassette 620 and the base unit 630 can be manually checked while avoiding an alarm issued by the control console 790 or incorrect data collection by the control console 790.

If it is desired that the drug cassette 620 in which the trouble occurred be temporarily attached to another base unit 630 to check its operation, the manually-operated switch 635 at the base unit 630, which is the temporary destination of attachment, is operated so that the checking function at the destination base unit 630 is bypassed. When the checking function for checking the drug cassette 620 is bypassed at the temporary destination base unit 630, the indicator 632 at the destination base unit 630 is lighted to indicate that manual operation independent of the management of the control console 790 is enabled. Similarly to the case described above, the check data 651 otherwise used in the checking at the temporary destination base unit 630 is temporarily saved as the saved data 652. The reading device 631 scans the identification information bearing member 621 of the drug cassette 620 but the checking routine 647 does not perform checking. Thus, while the indicator 632 at the temporary destination base unit 630 remains lighted, the same drug cassette 620, i.e. the drug cassette 620 in which the trouble occurred, can remain temporarily attached to the base unit 630 in which the indicator 632 is lighted.

When the manual checking is completed, the manually-operated switch 635 of the target base unit 630 is operated again. Thereupon, the values saved as the saved data 652 by the saving and restoring routine 647a of the microprocessor 640 provided in the base unit 630 are returned to the check data 651. The checking function of the checking routine 647 is restored in the drug feeder 613 so that the checking of the drug cassette 620 is resumed.

Thus, it is possible to easily and safely test replacement of drug cassettes in the drug feeder 613 of the first group in which safety is given top priority, without requiring rewriting of a drug master table.

An additional explanation will be given of a need to bypass checking in the temporary destination base unit 630 as well as in the base unit 630 in which the trouble occurs. In most cases, trouble checking involves removal of the drug cassette 620 from the base unit 630 in which a trouble occurs and attachment of it to the temporary destination base unit 630. These steps are repeated several times with different temporary destinations before settling on proper arrangement. Provision for locally bypassing checking in the temporary destination base unit 630 helps these steps to be repeated easily, accurately and promptly. That the check bypassing means comprises saving of the check data 651 as the saved data 652 and restoring the check data 651 from the saved data 652 enables the saved data at the temporary destination to be returned to the check data easily.

Examples of tablets that are likely to bounce higher in proportion to the height from which they fall include tablets with solid surfaces such as sugar-coated tablets or uncoated tablets that are compression molded to a predetermined configuration at a low pressure. For these drugs, troubles may often be prevented by attaching the drug cassette 620 at a low height. With other drugs that are opposite in characteristics, troubles are unlikely to occur even if the cassette is attached at a relatively high position. Trouble checking involving movement and replacement of the drug cassette is conducted on a trial and error basis by considering the above-described characteristics of drugs.

Types of drugs accommodated in the drug feeder 613 for automatic ejection differ from hospital to hospital. Data on drugs that are employed only in some hospitals for automatic ejection may be set in the drug master table. Manufacturers responsible for the installation of a drug dispensing system such as the tablet packing machine, however, may have to install the machine without any drug samples available. In such a case, the manufacturer may initially set up the tablet packing machine by registering the feeder storage address, the check data and the like in the drug master table, while arranging the drug feeders 613 for accommodating hospital-specific drugs in the drug feeder storage 612 in the alphabetical order. Manufacturer's personnel register the data in the drug master table once the drug feeders 613 are set and then modify the feeder arrangement as required upon reviewing dosage forms and the frequency of troubles. The personnel reconfigure the drug master in accordance with the modified feeder arrangement. As the personnel are responsible for speedy and accurate on-site fine-tuning as described above, the process has required extensive rules of thumb in the related art. With the inventive drug feeder and automatic dispenser, trouble checking can be performed easily by replacing drug cassettes while ensuring that checking is bypassed.

Fourth Embodiment-2

A description will now be given of the specific structure of the drug feeder and the automatic drug dispenser according to the fourth embodiment-2 with reference to the drawings. FIG. 30 is a block diagram showing the overall structure of a control system. FIGS. 31A and 31B are block diagrams showing the primary functions of the microprocessor 640 provided in each of the base units 630 in a distributed fashion, where FIG. 31A is a functional block diagram of the microprocessor 640 of the first group provided in the base unit 630 of the drug feeder 613 in the drug storage 611; and FIG. 31B is a functional block diagram of the microprocessor 640 of the second group provided in the base unit 630 of the drug feeder 730 in the feeder storage with cassette interchangeability 710.

The automatic dispenser according to the fourth embodiment-2 differs from that of the fourth embodiment-1 in that the tablet packing machine 700 is modified to result in a tablet packing machine 800 by omitting the rack control circuits 761 and 763 (see FIG. 30). Additionally, the check bypassing means in the microprocessor 640 in the base unit 630 of the drug feeder 613 of the first group is implemented as a flag updating routine 647c and a switch flag 653 instead of the saving and restoring routine 647a and the saved data 652, the flag updating routine 647c being a means with which to update a flag for switching between different operations of the checking means (see FIG. 31A).

In place of the rack control circuit 761, the communication routine 642a, the ejection detecting routine 643, the attachment/detachment routine 645, the information transmitting routine 646 and the ejection control routine 648 are transferred to the microprocessor 640 provided in the base unit 630 of the drug feeder 613 of the first group (see FIG. 31A). These routines are modified to a certain extent so as to directly control actuating members such as the motor 613j but realize the same functions in the microprocessor 640 as when these routines are installed in the rack control circuit 761. Since these routines are installed in each of the microprocessor 640, eliminating the need to select the I/O port number, the table search routine 644 and the port table 644a are not installed. The communication routine 642a only receives the drug ejection instruction addressed to the feeder storage address of the base unit 630 to which the associated microprocessor 640 is attached and delivers the instruction to the other routines.

In place of the rack control circuit 763, the communication routine 642b, the ejection detecting routine 643, the attachment/detachment routine 645, the information transmitting routine 646 and the ejection control routine 648 are transferred to the microprocessor 640 provided in the base unit 630 of the drug feeder 730 of the second group (see FIG. 31B). These routines are modified to a certain extent so as to directly control actuating members such as the motor 613j but realize the same functions in the microprocessor 640 as when these routines are installed in the rack control circuit 763. Since these routines are installed in each of the microprocessor 640, eliminating the need to select the I/O port number, the table search routine 644 and the port table 644b are not installed. The communication routine 642b only receives the drug ejection instruction that includes the check data that matches the check data 651 in the associated microprocessor 640 and delivers the instruction to the other routines.

Of those functions assumed by the table search routine 644, the function of requesting the control console 790 to provide a display that prompts the attachment or replacement of the drug cassette 620 and the function of providing guidance on the destination of cassette attachment by lighting the desired indicator 632 and the neighboring indicators 632 are transferred to the controller 780.

The flag updating routine 647c installed in the microprocessor 640 of the first group is configured to reverse the switch flag 653 in the memory 650 each time the manually-operated switch 635 is operated. The checking routine 647 checks the data by comparison in accordance with the value of the switch flag 653.

The rack control circuits 761 and 763 are not provided in the tablet packing machine 800 and their functions are distributed in the microprocessor 640 and the controller 780. Therefore, the same functions as are provided in the tablet packing machine 700 are provided in the tablet packing machine 800 so that repetition of the same description is avoided. Similarly to the tablet packing machine 700, the tablet packing machine 800 is capable of automatically packing various drugs under the management of the control console 790.

According to the inventive automatic dispenser, the control console 790 is capable of integral management of a system where the tablet packing matching 610, the tablet packing machine 700 and the tablet packing machine 800 are colocated, without causing any inconvenience.

[Other Points of Note]

The microprocessor 640 may not necessarily be of a one-chip type. The memory 650 may also be externally connected to the microprocessor 640. While the memory 650 should preferably be nonvolatile, the memory 650 may alternatively be provided with a battery.

The internal communication means 660 and other means for communication (for example, means for communication between machines) may be compliant with an ordinary communication protocol such as Ethernet™ or TCP/IP, or, alternatively, a protocol unique to the machine, as long as data can be exchanged between multiple machines and units. The communication means may also be wired or wireless, or may or may not be for multidrop communication.

In the embodiment described above, the feeder storage with cassette interchangeability 710 is provided on the right side of the table packing machines 700 and 800. Alternatively, the feeder storage with cassette interchangeability 710 may be provided at other positions including the left side or the front of the machine.

While the tablet packing machines 610, 700 and 800 are only designed for automatic packing of tablets, the machines may pack other types of drugs such as capsules. The tablet packing machines 610, 700 and 800 may be combined with a mechanism for packing powder medicine.

Fifth Embodiment

The fifth embodiment relates to a tablet counting and monitoring apparatus for capturing images of packed tablets so as to count tablets without unpacking. More particularly, the fifth embodiment relates to a tablet counting and monitoring apparatus for transporting strip-like packing paper comprising a series of packs and successively counting tablets.

A tablet counting and monitoring apparatus is known (see, for example, patent document No. 7) which is provided adjacent to a tablet packing machine which compartmentalizes tablets and seals the tablets in packing paper one after another so as to successively form packs of tablets (individual packs) in accordance with prescription information. The tablet counting and monitoring apparatus receives the packing paper comprising the packs and automatically determines the number of tablets in the packs by successively capturing images of the packs. In addition to automatically counting and monitoring the number of tablets in the packs, the tablet counting and monitoring apparatus automatically checks the count against the prescription information so as to determine whether excess or deficiency of drugs occurs.

According to imaging-based tablet counting as described above, images may differ depending on the condition in which tablets are accommodated in packs and the difference affects accuracy of counting. More specifically, if tablets are piled up on one another such that they are hardly distinguishable, some tablets may be excluded from the count. Therefore, the apparatus is designed to allow visual examination by monitoring personnel by providing image display. For example, if the number of tablets prescribed differs from the count, an alarm is sounded to prompt visual examination of a displayed image.

However, if the frequency of visual examination is high, it detracts from the advantage of automation enabled by the tablet counting and monitoring apparatus. Suspension in an automatic process lowers throughput and imposes a burden on the personnel. Therefore, it is desired to take decisive measures to prevent tablets from being piled on one another in the pack. Since increase in maintenance cost as well as in fabrication cost is unfavorable, introduction of complex mechanisms or measures should best be avoided. In this respect, there have been developed tablet counting and monitoring apparatuses designed to disentangle tablets accommodated in packs before capturing an image thereof.

More specifically, a clamp mechanism and a shaking mechanism implement a pre-processing measure in a simple fashion, whereby tablets accommodated in packs are placed, before imaging, in an disentangled state (a state in which piling-up or aggregation does not occur) in which the tablets are distinguishable from each other, without tearing the packing paper. A clamp mechanism for temporarily holding an end of the pack, a shaking mechanism for shaking the pack thus held and a transporting mechanism for transporting the pack to a position at which the clamp mechanism and the shaking mechanism can operably act on the pack are built in the tablet counting and monitoring apparatus for automatically determining the number of tablets in the pack by capturing an image of the pack (see for example, patent document No. 8.

The capability of the tablet counting and monitoring apparatus as described above for image-based counting and monitoring of tablets is improved from that of the apparatus in the related art. In association with this, the apparatus is capable of automatic counting and monitoring for an extended period of time, while transporting the packing paper, ensuring improved processing efficiency.

As the distance of continuous transportation of packing paper is extended or the speed of transportation is increased, however, the characteristics of paper packing the drugs will exercise increasingly serious undesirable effects on transportation, requiring additional countermeasures in order to further improve efficiency and availability.

More specifically, the way a swollen pack is produced as a result of introducing drugs in packing paper differs from pack to pack since the way drugs are accommodated in the packing paper differs from pack to pack. Packs are variably deformed in the direction of thickness, width or length, resulting in the packing paper being twisted and undulating. Even if a twist occurs only locally and on a small scale, adverse effects from the twist may be built up and amplified depending on the distance of transportation or speed of transportation, causing improper transportation or failure in transportation such as jamming or displacement. In order to reduce the frequency of occurrence of such troubles and improve efficiency and availability, it is essential to introduce countermeasures to stabilize the transporting condition. One specific approach is to introduce a means for eliminating the twist of packing paper transported past an imaging position.

As described above, the way packing paper is twisted is irregular and so the mere provision of a stationary guiding means such as a mechanical guide is not sufficient to eliminate the twist of packing paper. It is therefore desirable that the status of twist of paper be detected to eliminate twist in a decisive and definitive manner. The provision of a detecting member capable of accurately detecting various statuses of soft and easily deformable packing paper may allow easy customization but would incur unbearably high cost.

Accordingly, one of the technical goals to be achieved would be to achieve detection and elimination of twist of packing paper, while avoiding an increase in the cost by effectively utilizing existing components in accordance with the characteristics of packing paper.

A summary of the fifth embodiment will be given.

(1) A tablet counting and monitoring apparatus according to the fifth embodiment for capturing images of a series of packs comprising perforated compartments in packing paper and automatically counting tablets in the packs, comprises: a tilt detecting means which detects the tilt of the perforation or an equivalent thereof, in accordance with captured image data; and a transporting mechanism which varies the direction of transportation of the packing paper such that the tilt (i.e. the tilt of the perforation or the equivalent thereof) is eliminated, in accordance with the tilt thus detected.

The term "equivalent of the perforation" refers to something that is tilted together with the perforation in association with the twist of the packing paper and that is subject to image-based tilt detection, similar to the perforation. Examples of equivalent include a marking line printed in parallel with the perforation, a marking line printed in the neighborhood of both ends of the perforation or a boundary which is between areas characterized by different colors or shades and which is parallel with the perforation. The tilt is measured with reference to a state in which the packing paper is transported straight in a stable manner without undergoing any twist.

(2) The tablet counting and monitoring apparatus of (1) according to the fifth embodiment may be characterized in that a disentangling mechanism for applying mechanical action on the pack and disentangling the drugs inside is provided upstream of an imaging position, and the transporting mechanism is capable of transporting the packing paper in a reverse direction as well as in a forward direction.

The tablet counting and monitoring apparatus of (1) takes advantage of the fact that a perforation, which is usually provided in a packing paper, is tilted as the packing paper is twisted and the fact that the perforation is captured at the end of an image of the pack. The tilt of a perforation or an equivalent thereof is detected by referring to an image data of the pack. The tablet counting and monitoring apparatus of (1) is also designed to vary the direction of transportation of the packing paper in accordance with the tilt, so as to eliminate the tilt. With this, tilt that is required to eliminate twist is detected by means of software modification without adding any hardware for detection. Accordingly, detection and elimination of twist are achieved while avoiding an increase in cost.

According to the embodiment, an inexpensive tablet counting and monitoring apparatus which is superior in efficiency and availability is provided.

In the tablet counting and monitoring apparatus of (2), the disentangling mechanism is provided upstream of the imaging position and the transporting mechanism is capable of transporting the packing paper in a reverse direction. When the tablets in a pack cannot be distinguished from each other in an image, the pack is returned to the position of the disentangling mechanism to resume the preprocessing and the subsequent steps. Accordingly, capabilities for distinguishing, counting and monitoring tablets are improved.

It will be noted that, by repeating forward and reverse transportation, the packing paper will undergo serious deformation. This will in itself increase the frequency of occurrence of improper transportation or failure in transportation such as jamming or displacement. The fifth embodiment is capable of increasing the accuracy of counting without decreasing efficiency and availability, by combining bidirectional transportation with countermeasures for detecting and eliminating the twist of the packing paper.

According to the embodiment, an inexpensive tablet counting and monitoring apparatus which is superior in efficiency and availability is provided.

Specific embodiments of the tablet counting and monitoring apparatus of the fifth embodiment will be described below by explaining the fifth embodiment-1 and the fifth embodiment-2.

The fifth embodiment-1 shown in FIGS. 35A through 39H is an embodiment of all the features (1) and (2) above. The fifth embodiment-2 shown in FIGS. 40A-40B is a variation thereof.

For brevity, support members such as frames, fastening members such as bolts, joint members such as hinges, actuators such as an electric motor, transmission mechanisms such as cams, electric circuits such as motor drivers and detailed circuit features in an electronic circuit such as controllers are omitted from the illustration. Those elements that are required in the invention and elements related thereto are mainly illustrated.

Fifth Embodiment-1

Figure 35A:
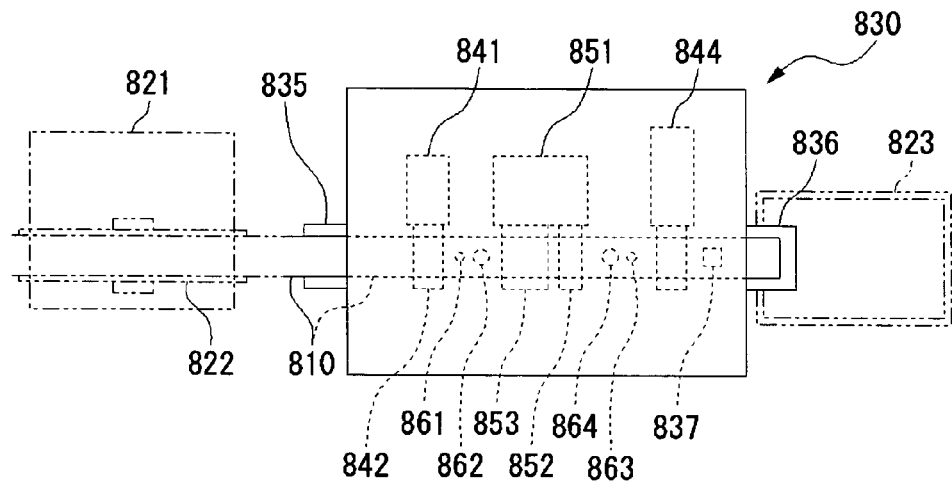
FIG. 35A is a top view of a tablet counting and monitoring apparatus.
Figure 35B:
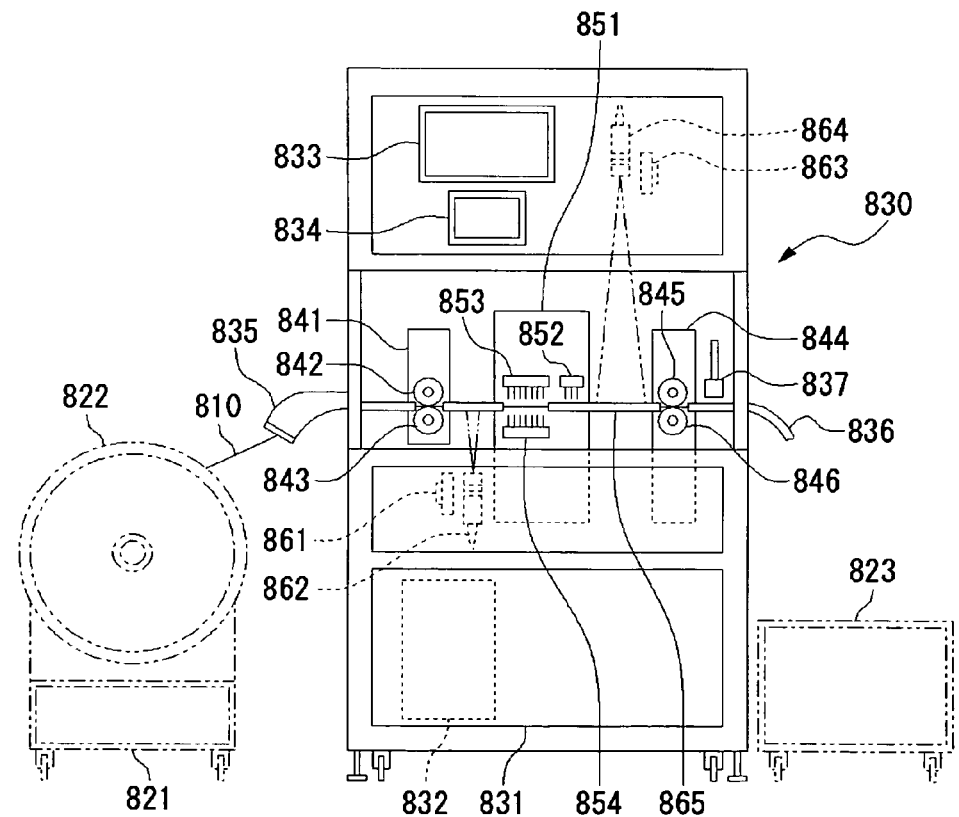
FIG. 35B is a front view of the tablet counting and monitoring apparatus.
Figure 36A:
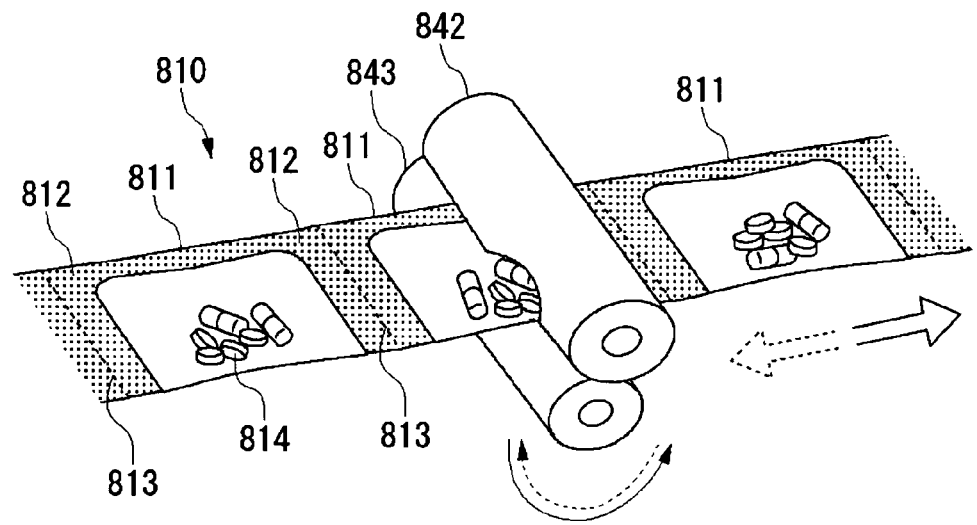
FIGS. 36A and 36B are perspective views showing the main part of a transporting mechanism.
Figure 36B:
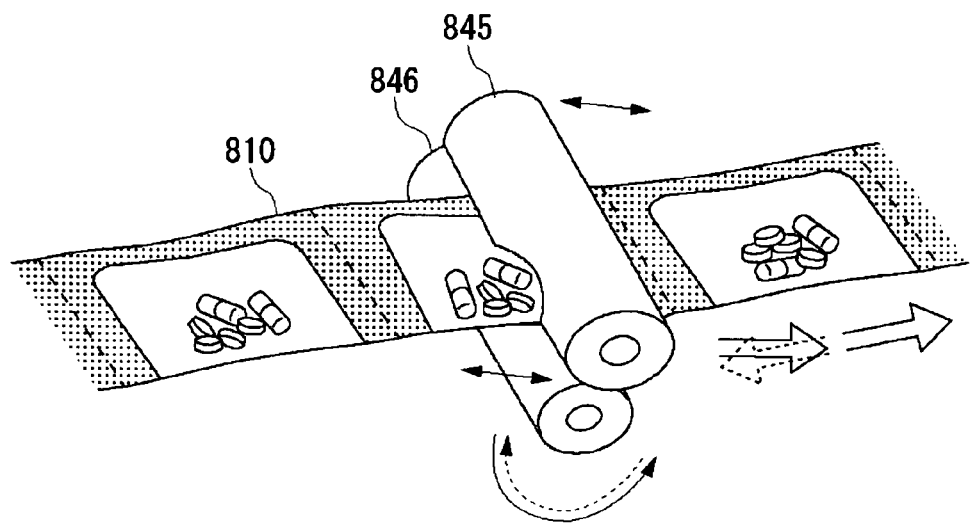
Figure 37:
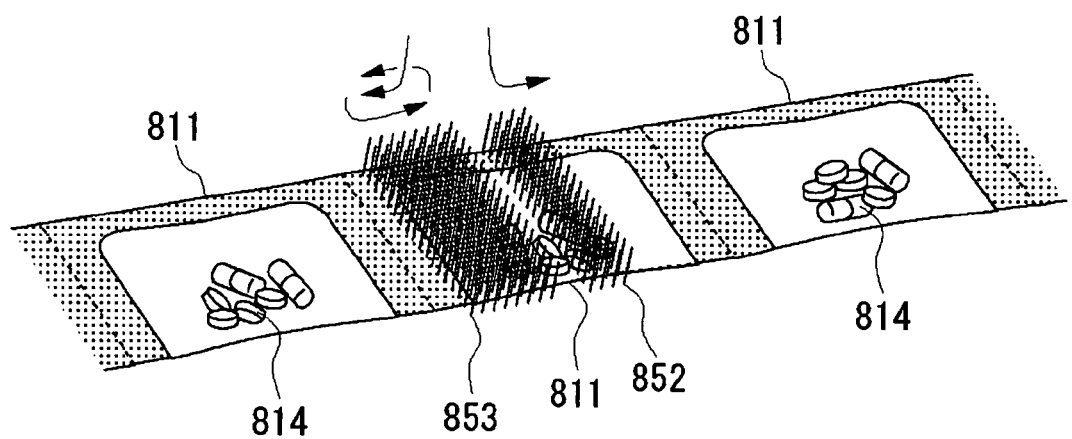
FIG. 37 is a perspective view showing the main part of a disentangling mechanism.
Figure 38:
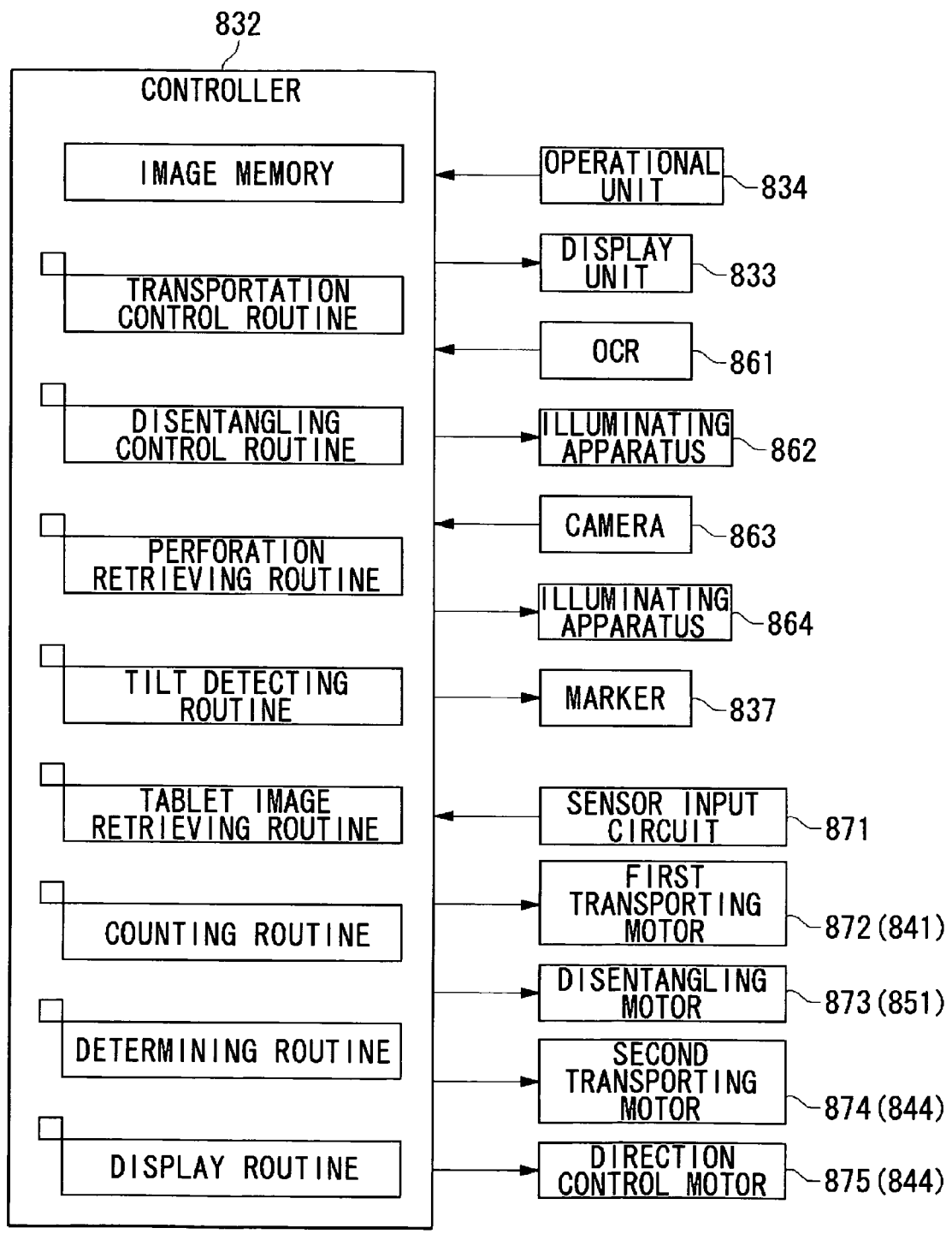
FIG. 38 is a block diagram of an electronic circuit unit.

A specific structure of the tablet counting and monitoring apparatus according to the fifth embodiment-1 will be described with reference to the associated drawings. FIGS. 35A and 35B show the mechanical structure of the tablet counting and monitoring apparatus, wherein FIG. 35A is a top view and FIG. 35B is a front view. FIGS. 36A and 36B show the main part of a transporting mechanism, wherein FIGS. 36A and 36B are both perspective views. FIG. 37 is a perspective view showing the main part of a disentangling mechanism. FIG. 38 is a block diagram of an electronic circuit unit.

Figure 39A:
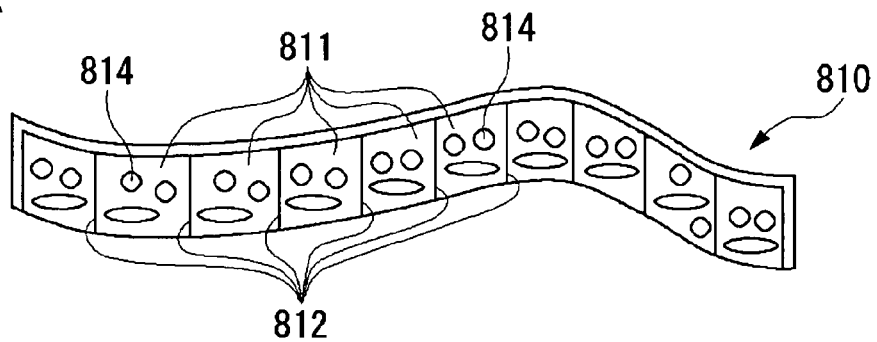
FIG. 39A shows packing paper containing a large number of packs as a series of compartments in the packing paper.
Figure 40A:
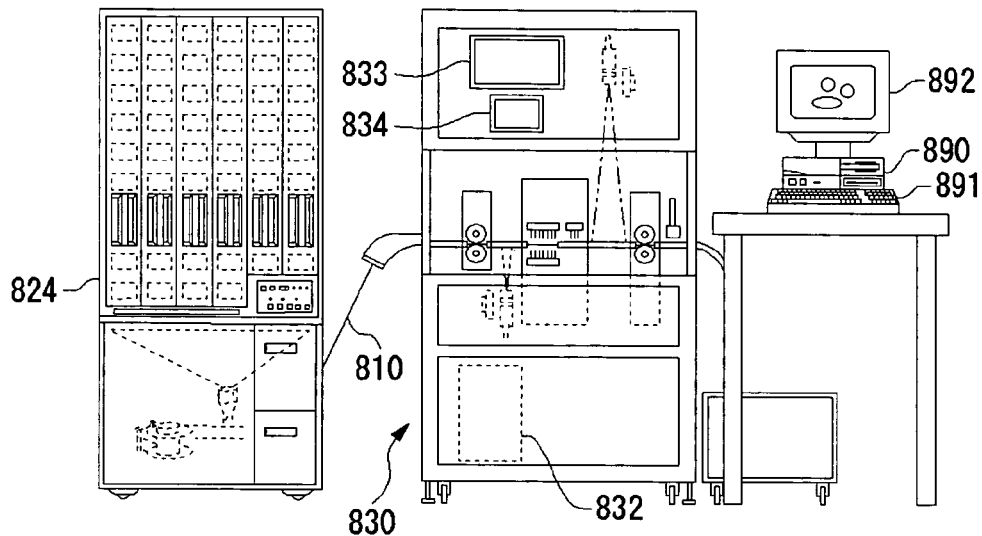
FIG. 40A is a front view showing the mechanical structure of the tablet counting and monitoring apparatus according to the fifth embodiment-2.
Figure 40B:
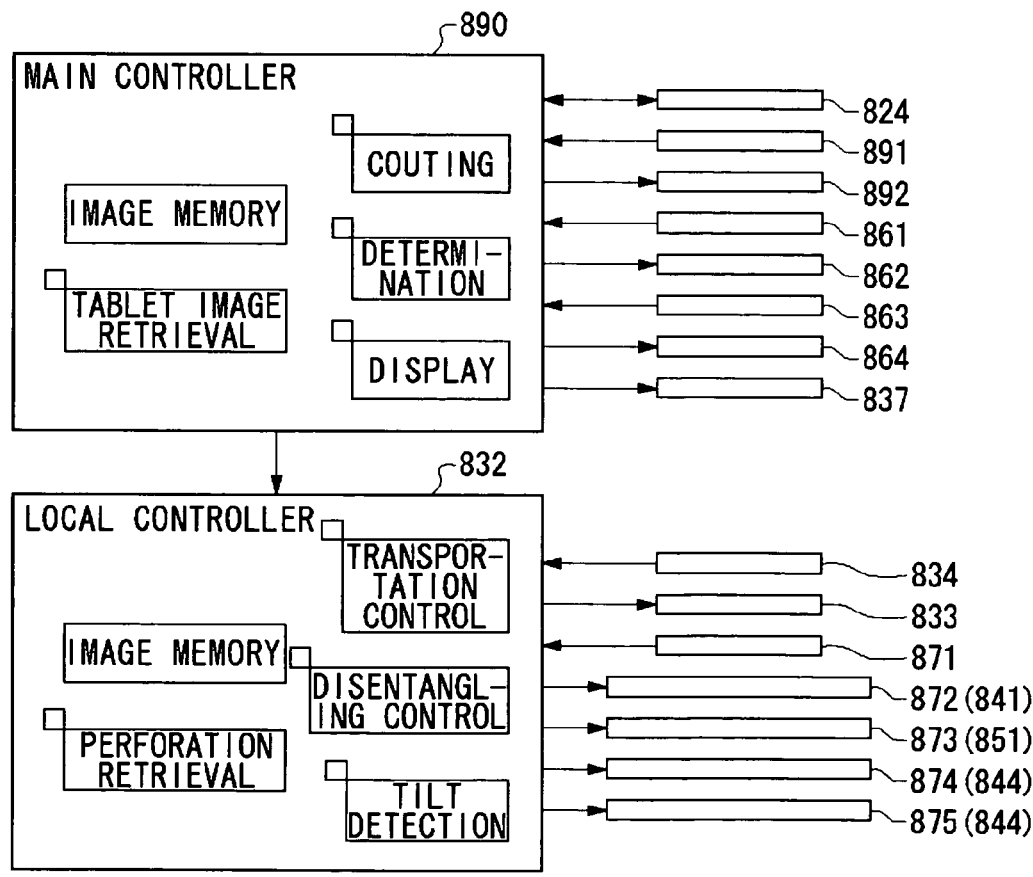
FIG. 40B is a functional block diagram of an electronic circuit unit according to the fifth embodiment-2.

A tablet counting and monitoring apparatus 830 (see FIGS. 35A and 35B) is for counting and monitoring packs 811 (individual packs) provided as a longitudinal series of packs comprising compartments in packing paper 810 (see FIG. 39A). The tablet counting and monitoring apparatus 830 roughly comprises: a transporting/disentangling/imaging mechanism (see FIGS. 35A-37) for pulling in the packing paper 810 so as to capture an image of the pack 811; and an electronic circuit unit (see FIGS. 35A-38) for controlling the operation of the mechanism and automatically checking the number of tablets in the pack.

In the illustrated example (see FIGS. 35A and 35B), the transporting/disentangling/imaging mechanism is provided along a route in which the packing paper is transported inside a housing. The transporting/disentangling/imaging mechanism pulls in the packing paper 810 at an entry guide 835 and ejects the same via an exit guide 836 on the right side.

A programmable arithmetic and control unit such as a microprocessor is employed to formulate the electronic circuit unit (see FIGS. 35A and 35B). A controller 832, which constitutes a main part of the unit, is stored in an electric unit 831 inside the housing together with a power supply unit (not shown). An operational unit 834 such as an operation panel provided with switches and keys, and a display unit 833 such as a liquid crystal panel are provided at positions that ensure ease of use (for example, on the front of the upper part of the housing).

Perforations 813 separate between the packs 811 longitudinally (in the illustration, in the left-right direction) (see FIGS. 39A-39C) at respective end portions 812 of the packs 811. The two end portions 812 of each pack and one of the remaining sides are heat sealed. The remaining side is bent so as to accommodate a tablet 814 inside.

To describe the transporting/disentangling/imaging mechanism in further detail, the mechanism (see FIGS. 35A and 35B) comprises: front transportation units 841-843; printed information reading units 861-862; disentangling units 851-854; imaging units 863-864; back transportation units 844-846; and a marker 837. The units are arranged in the stated order from upstream to downstream (from left to right in FIGS. 35A and 35B) along a packing paper transportation route extending horizontally from the entry guide 835 to the exit guide 836. The units are supported at predetermined positions by appropriate posts or frames (not shown).

An area in the packing paper transportation route which lies between the disentangling units 851-854 and the back transportation units 844-846 and which is faced by the imaging units 863-864 is an imaging stage 865. The imaging units 863-864 comprise an imaging apparatus 863 such as a CCD camera and an illuminating apparatus 864 such as a halogen lamp. The illuminating apparatus 864 illuminates the imaging stage 865 so that the imaging apparatus 863 captures an image of the pack 811 in the packing paper 810 transported to the imaging stage 865. The imaging units 863-864 as illustrated are of a reflecting type but may alternatively be of transmission type.

An area in the packing paper transportation route which lies between the front transportation units 841-843 and the disentangling units 851-854 and which is faced by the printed information reading units 861-862 is a reading stage. Information indicating the number of tablets and the like is usually printed on the back of the packing paper 810. More specifically, information may be printed on each pack 811 or on each empty pack 811 not accommodating any tablets. Information is printed using a font prescribed for optical character recognition (OCR). The printed information reading units 861-862 comprise an optical character reader (OCR) 861 compatible with the prescribed font and an illuminating apparatus 862 such as a halogen lamp. The illuminating apparatus 862 illuminates the reading stage so that the OCR 861 reads information printed on the pack 811 in the packing paper 810 transported to the stage.

The front transportation units 841-843 (see FIGS. 35A-35B and FIG. 36A) and the back transportation units 844-846 constitute a transporting mechanism. The front transportation units 841-843 comprise: a first transporting mechanism 841 provided beside the packing paper transportation route (toward the back end in FIGS. 35A and 35B); a roller 842 projecting from the first transporting mechanism 841 into a space above the packing paper transportation route; and a roller 843 projecting from the first transporting mechanism 841 into a space below the packing paper transportation route. By driving the pair of rollers 842 and 843 into axial rotation by a motor and a driving mechanism of the first transporting mechanism 841, the packing paper 810 is sandwiched between the pair of rollers 842 and 842 for transportation. The first transporting mechanism 841 is capable of rotating the pair of rollers 842 and 843 in both directions so as to enable forward transportation for transporting the packing paper 810 from the entry guide 835 to the exit guide 836 and reverse transportation in a reverse direction. Each of the rollers 842 and 843 is formed of an easily deformable material such as sponge so as not to be affected by variation in thickness of the packing paper 810.

Similarly, the back transportation units 844-846 (see FIGS. 35A and 35B and FIG. 36B) comprise: a second transporting mechanism 844 provided beside the packing paper transportation route (toward the back end in FIGS. 35A and 35B); a roller 845 projecting from the second transporting mechanism 844 into a space above the packing paper transportation route; and a roller 846 projecting from the second transporting mechanism 844 into a space below the packing paper transportation route. By driving the pair of rollers 845 and 846 into axial rotation by a motor and a driving mechanism of the second transporting mechanism 844, the packing paper 810 is sandwiched between the pair of rollers 845 and 846 for transportation. Similarly to the rollers of the front transportation units 841-843, the rollers 845 and 846 are formed of a material such as soft sponge and enable forward transportation and reverse transportation by bidirectional axial rotation. A difference is that the direction of transporting the packing paper 810 is variable.

More specifically, the pair of rollers 845 and 846 are configured to make rocking motion (bidirectional rotation) around a plumb line through the packing paper transportation route. That is, the pair of rollers 845 and 846 can make propeller-like motion together around a virtual plumb line through a horizontal plane as well as rotating around the horizontal axis. Since it is desired that the plumb line around which the rollers rock be at the center of the packing paper transportation route, the entirety of the second transporting mechanism 844 or those parts thereof supporting the rollers 845 and 846 are made to make rocking motion in conjunction with the pair of rollers 845 and 846.

The disentangling units 851-854 (see FIGS. 35A, 35B and FIG. 37) is provided with a disentangling mechanism 851 provided beside the packing paper transportation route (toward the back end in FIGS. 35A and 35B), brushes 852 and 853 projecting from the disentangling mechanism 851 into a space above the packing paper transportation route, and a brush 854 projecting from the disentangling mechanism 851 into a space below the packing paper transportation route. A motor and a driving mechanism of the disentangling mechanism 851 allow the brushes 852-854 to cooperate with each other to apply mechanical action on the pack 811 in the packing paper 810. The motion of the brushes 852-854 is for disentangling the tablets 814 in the pack 811 efficiently. For example, the brush 852 is lowered to make a sweeping motion in the direction of transportation. The brush 853 is lowered to provide a stirring action by making a spiral motion.

A detailed description will now be given of an electronic circuit unit and a driving unit controlled by the electronic circuit unit (see FIG. 38). The controller 832 comprises a microprocessor or the like as described above. In addition to the operational unit 834 and the display unit 833 described above, the OCR 861 and the imaging unit 863 are also connected to the controller 832 by signal cables. The controller 832 receives printed information read from the packing paper 810 as well as controlling the timing of illumination and reading. The imaging apparatus 863 and the illuminating apparatus 864 are also connected to the controller 832 by signal cables. The controller 832 imports image data in an image memory as well as controlling the timing of illumination and imaging. The marker 837 to write a bad mark on the packing paper 810 is also connected to the controller 832 and is under its control.

Further, the controller 32 comprises: a sensor input circuit 871 for receiving results of detection by various sensors (for example, information on the pack 811) over cable lines; a circuit which is provided in the first transporting mechanism 841 and which controls and drives a first transporting motor 872 for driving the roller pairs 842 and 843 into rotation; a circuit which is provided in the disentangling mechanism 851 and which drives an disentangling motor 873 for moving the brushes 852-854 to disentangle tablets; a circuit which is provided in the second transporting mechanism 844 and controls and drives a second transporting motor 874 for driving the roller pairs 845 and 846 into axial rotation; and a circuit which is also provided in the second transporting mechanism 844 and which controls and drives a direction control motor 875 for placing the roller pairs 845 and 846 into rocking motion instead of axial rotation.

The controller 832 is provided with an image memory for temporarily storing image data imported from the imaging apparatus 863. Several programs are installed in the controller 832 to execute tablet counting and monitoring using the image memory and the peripheral circuits described above. More specifically, installed in the controller 132 are a transportation control routine which controls the first transporting motor 872 and the second transporting motor 874 for transporting the packing paper 810; a disentangling control routine which controls the disentangling motor 873 for disentangling the tablets 814 in the pack 811; a perforation retrieving routine which retrieves a sub-image containing the perforation 813 by referring to the image data in the image memory; a tilt detecting routine which calculates the tilt of the perforation 813 by referring to the result of retrieval; a tablet image retrieving routine which retrieves a sub-image containing the tablets 814 in the pack by referring to the image data in the image memory; a counting routine which counts the number of tablets 814 in the pack by referring to the result of retrieval; a determining routine which determines whether the count matches a prescribed value; and a display routine which displays a result of imaging, a result of determination, etc. Characteristic processes performed by the routines will be described below in connection with the operation.

Figure 39B:
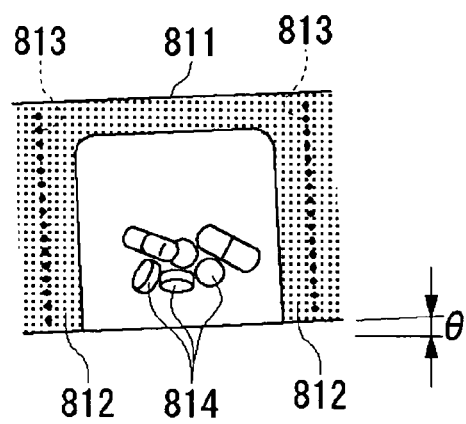
FIG. 39B shows a pack containing tablets before disentangling.
Figure 39C:
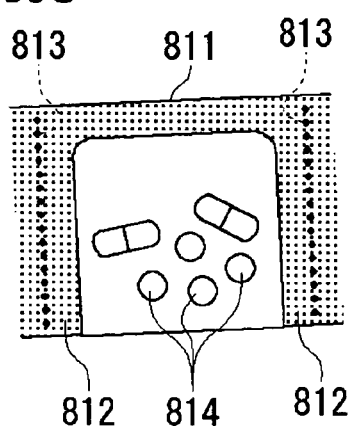
FIG. 39C shows the tablets and the pack after disentangling.
Figure 39D:
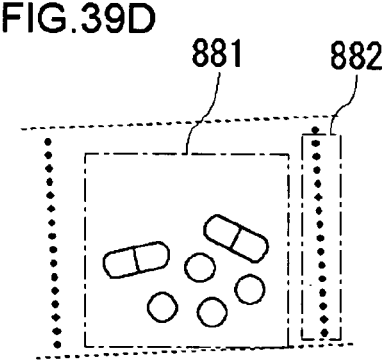
FIG. 39D shows an example of image data.
Figure 39E:
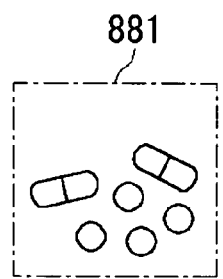
FIG. 39E shows an example of data of a tablet image area.
Figure 39F:
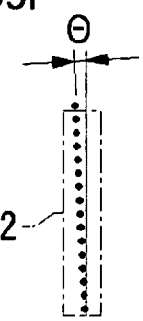
FIG. 39F shows an example of data of a perforation area.
Figure 39G:
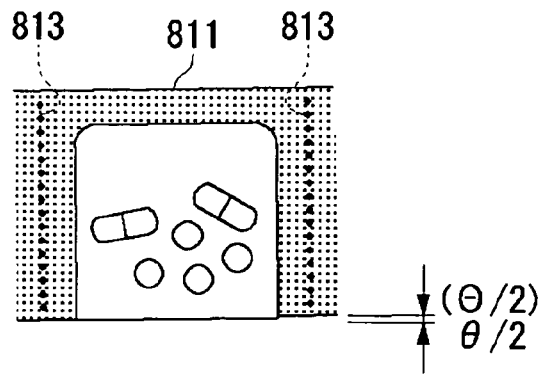
FIG. 39G shows a pack halfway adjusted for its direction.
Figure 39H:
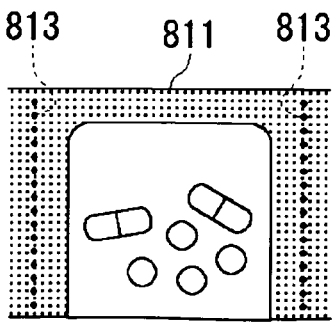
FIG. 39H shows a pack in which twist is eliminated.

The usage mode and the operation of the tablet counting and monitoring apparatus according to the fifth embodiment-1 will be described with reference to the drawings. FIGS. 35A and 35B are a top view and a front view of the tablet counting and monitoring apparatus 830 to which a supplying unit 821 for supplying the packing paper 810 and a storage basket 823 are attached. FIGS. 39A-39H are top views illustrating the operation. FIG. 39A shows packing paper containing a large number of packs as a series of compartments in the packing paper; FIG. 39B shows a pack containing tablets before disentangling; FIG. 39C shows the tablets and the pack after disentangling; FIG. 39D shows an example of image data; FIG. 39E shows an example of data of a tablet image area; FIG. 39F shows an example of data of a perforation area; FIG. 39G shows a pack halfway adjusted for its direction; and FIG. 39H shows a pack in which twist is eliminated.

The packing paper 810 subject to counting and monitoring (see FIG. 39A) comprises a series of packs 811. Each pack 811 is partitioned by the end portions 812 and contains at least one tablet 814. A typical size of the pack 11 (see FIGS. 39A and 39C) is such that the width thereof shown vertically in the figure is approximately 70 mm and the length thereof shown horizontally in the figure is approximately 80 mm. The width of the end portion 812 (an interval between the horizontally adjacent packs 811 in the figure) is approximately 10 mm. A straight, interrupted perforation 813 is formed in the end portion 812. Typically, the tablet 814 is a ball-shaped drug with a diameter of about several mm, an elongated capsule or a mixture of them.

The tablet counting and monitoring apparatus 830 is a stand alone apparatus (see FIGS. 35A and 35B). In order to supply the packing paper 810 to the tablet counting and monitoring apparatus 830, the supplying unit 821 is attached to the entry guide 835 and the packing paper 810 comprising packs of tablets is wrapped around a reel 822 of the supplying unit 821. The storage basket 823 for receiving the packing paper 810 ejected from the tablet counting and monitoring apparatus 830 is placed beside the exit guide 836. When the leading edge of the packing paper 810 is set in the entry guide 835 and the transporting mechanisms 841-846, the packing paper 810 is intermittently transmitted by the transporting mechanisms 841-846 under the control of the transportation control routine.

During the intermittent transportation, the OCR 861 and the illuminating apparatus 862 of the reading stage upstream are used to read information printed on the pack 811. The disentangling units 851-854 in the disentangling stage midstream apply a disentangling process (preprocessing) to the pack 811 arriving at the stage, under the control of the disentangling control routine. The imaging apparatus 863 and the illuminating apparatus 864 in the imaging stage 865 downstream capture an image of the pack 811. Accordingly, even when the tablets 814 are piled up on one another in the pack 811 before disentangling (see FIG. 39B), the tablets 814 are disentangled in the pack 811 after disentangling so that they are no longer piled up on one another (see FIG. 39C).

The image data captured by the imaging apparatus 863 (see FIG. 39D) is displayed on the display unit 833 and stored in the image memory of the controller 832. The image is subject to image processing by the perforation retrieving routine and the tablet image retrieving routine. The tablet image retrieving routine retrieves a tablet image area 881 that will include an image of the tablet 814 (see FIG. 39A). Noise rejection process or tablet image dividing process are applied to the area. The tablet image area 881 is retrieved from a subarea of a fixed range, unless the twist of the packing paper 810, i.e. the tilt θ of the pack 811 with respect to the direction of transportation, is extremely large (see FIG. 39B). The number of tablet image blocks contained in the tablet image area 881 is counted by the counting routine and the count is made to represent the number of tablets in the pack 811.

The number of tablets is compared with a prescribed value known as a result of reading by the OCR 861. If the count matches the value, it is determined that the count is proper. If there is matching failure, it is determined that the count is improper. The result of determination is displayed on the display unit 833 by the display routine. If it is determined that the count is proper, the transportation control routine transports the packing paper 810 in a forward direction. If it is determined that the count is improper, the transportation control routine transports the packing paper 810 in a reverse direction so that the disentangling process and the subsequent steps are resumed. If it is determined that the count is still improper upon resumption, associated display of the monitoring result is provided on the display unit 833. A bad mark is written in the associated pack 811 with the marker 837.

In parallel with tablet counting, the twist of the packing paper is detected and eliminated. That is, the perforation retrieving routine retrieves a perforation area 882 that includes an image of the perforation 813, by referring to the image data in the image memory (see FIG. 39F). Noise rejection is applied to the retrieved area. The perforation area 882 is retrieved from a subarea of a fixed range, unless the twist of the packing paper 810, i.e. the tilt θ of the pack 811 with respect to the direction of transportation, is extremely large. A line approximating the perforation is determined by referring to the perforation area 882, using a known method such as the least square method. The tilt component of the approximating line is made to represent the tilt Θ of the perforation.

The tilt Θ represents the twist of the packing paper 810 quite well and is almost equal to the tilt θ. Therefore, the tilt Θ is delivered to the transportation control routine so that the direction control motor 875 is driven in a direction that eliminates the tilt Θ. Theoretically, the amount of directional control may be equal to Θ. In the illustrated example, however, the amount of control applied while a single pack is being fed is restricted to half of the tilt Θ(=Θ/2) with an emphasis on stability. Accordingly, the twist of the packing paper 810 is reduced to θ/2 (see FIG. 39G). Unless a new factor that causes twist is introduced, the twist of the packing paper 810 gradually disappears (see FIG. 394H). In actuality, factors that cause twist are added one after another. They are, however, prevented from accumulating to grow to a large scale. The twist of the packing paper 810 converges to a range that does not affect high-speed transportation for a prolonged period of time.

Fifth Embodiment-2

A description will now be given of the specific structure of the tablet counting and monitoring apparatus according to the fifth embodiment-2 with reference to the drawings. FIG. 40A is a front view showing the mechanical structure of the tablet counting and monitoring apparatus according to the fifth embodiment-2, and FIG. 40B is a functional block diagram of an electronic circuit unit thereof.

A difference between this tablet counting and monitoring apparatus from that of the fifth embodiment-1 is that a tablet packing machine 824 is introduced instead of the supplying unit 821 and that a main controller 890 is added.

The main controller 890 comprises a personal computer or the like to which are attached an operational unit 891 such as a key board, and a display unit 892 and the like. The main controller 890 is placed on desk beside the tablet counting and monitoring apparatus 830 for ease of use. The controller 832 serves as a local controller. The tablet image retrieving routine, the counting routine, the determining routine, the display routine, interfaces for the printed information reading units 861-862 and the imaging units 863-864, and a circuit for controlling and driving the marker 837 are transferred tom the controller 832 to the main controller 890.

The controllers 890 and 832 are communicably connected to each other by signal cables for transmitting instructions for operation and results of operation. The main controller 890 is also communicably connected to the controller of the tablet packing machine 824 by signal cables.

Under the integral control of the main controller 890, the packing paper 810 accommodating the tablets 814 in the tablet packing machine 824 is fed to the tablet counting and monitoring apparatus 830 and subject to automatic counting and monitoring.

[Other Points of Note]

In the fifth embodiment-1, the disentangling mechanism is implemented by brushes. Other structures of the disentangling mechanism are possible as long as the mechanism is capable of applying mechanical action on the pack 811 and disentangling the tablets 814 inside. For example, an oscillating member may oscillate the pack 811, a clamp member may hold the ends of the pack 811 to deform (expand) the pack 811, or vacuum may be used to swell the pack 811 temporarily. A combination of these measures may also be used.

In the fifth embodiment-2, the main controller 890 (counting and monitoring unit) and the tablet counting and monitoring apparatus 830 (transporting/disentangling/imaging mechanism) are in a one-to-one relation. If the processing capability of the main controller 890 is sufficient, multiple tablet counting and monitoring apparatuses 830 may be connected to a single main controller 890.

The following technical ideas are encompassed by the embodiments described above and variations thereof.

(1) An automatic drug dispenser comprising: a drug cassette which ejectably accommodates drugs; a base unit which detachably supports the drug cassette and drives a motor to eject drugs; a drug feeder storage which is designed to store a large number of base units; a reading device which is provided in each of the base units and reads identification information assigned to the drug cassette; and a checking means which compares a result of reading with pre-stored check data, wherein a set of a microprocessor and a memory, or a microprocessor with a built-in memory is mounted in each of the base units, and the checking means and the check data are built in each microprocessor in a distributed manner.

(2) The automatic drug dispenser of (1) may further be characterized in that, if the result of comparison indicates matching failure, the same information as output when the associated drug cassette is empty is caused to be output, by suspending motor-driven ejection by the associated base unit.

(3) The automatic drug dispenser of (1) or (2) may further comprise an overwriting means which overwrites the check data with the identification information read by the reading device.

(4) The automatic drug dispenser of any one of (1) through (3) may be characterized in that the microprocessor is provided with a communication means, each of the base units is provided with a plurality of indicators of different colors such that at least one of the indicators displays a drug ejection enabled state and at least one other of the indicators displays a communication enabled state indicating that communication is enabled in the microprocessor.

(5) The automatic drug dispenser of any one of (1) through (4) may be characterized in that the microprocessor stores, in a memory, drug dispensing history information related to the operating condition of drug ejection by the associated base unit.

(6) The automatic drug dispenser of any one of (1) through (5) may be characterized in that the microprocessor stores, in a memory, attachment/detachment history information related to the attachment and detachment of a drug cassette to the associated base unit.

(7) The automatic drug dispenser of any of (5) or (6) may be characterized in that the microprocessor ranks, for storage, history information according to whether the information is related to normal operation or abnormal operation.

(8) The automatic drug dispenser of any of (1) through (7) may be characterized in that the microprocessor stores, in a memory, selection history information related to the selection of specification of the associated drug cassette.

(9) The automatic drug dispenser of any one of (1) through (8) may be characterized in that the microprocessor stores, in a memory, fabrication history information related to the fabrication process of the associated drug cassette.

(10) The automatic drug dispenser of any of (5) or (6) may be characterized in that the microprocessor comprises a transmitting means which transmits the history information stored in the memory outside the dispenser.

(11) A drug feeder for containing and feeding a drug, comprising: a container main body and an aligner, wherein the container main body comprises: a cell unit which contains a drug; and an aligner housing unit which is adjacent to the bottom of the cell unit and which rotatably accommodates a main body of the aligner, at least one gutter into which a drug enters via the cell unit is provided at the periphery of the aligner, the gutter extends in a direction having a vertical component, and the depth and width of the gutter are determined such that the longest dimension of a drug is aligned with the direction of extension of the gutter, a partition plate projects from the interior wall of the aligner housing unit so as to partition the gutter into a preparatory aligning unit in the top half and an aligning unit in the bottom half, a drug outlet is provided in the aligner housing unit at a position below the partition plate so as to allow a drug in the aligning unit to fall, designating the longest dimension of a drug as its total length L, the gutter length of the aligning unit is substantially equal to the total length L, and the gutter length of the preparatory aligning unit is smaller than the total length L.

(12) The drug feeder as described in (11) above, in which the aligner is generally of a cylindrical form, and a space inside the aligner housing unit is of a cylindrical form having an inner diameter sufficiently large to rotatably accommodate the aligner.

(13) The drug feeder as described in (11) above, in which the drug is as described below in (A) or (B).

(A) A drug of a form with different dimensions in all three mutually perpendicular directions (x, y, z), in which, designating the largest dimension as a total length L and the remaining two dimensions as a total width W and a total thickness T, the total length L is at least twice the larger of the total width W and total thickness T.

(B) A drug of a form in which one of the dimensions in the three mutually perpendicular directions (x, y, z) is longer than the other two dimensions and the remaining two dimensions are equal to each other, and in which, designating the longest dimension as a total length L and the remaining two dimensions as a total width W and a total thickness T, the total length L is at least twice the total width W.

(14) An assembly of drug feeders which contain and feed a drug, wherein each drug feeder comprises a container main body and an aligner, each drug feeder is dedicated to a particular one of drug types that differ in dimensions so that each feeder contains and feeds only one type of drug, the container main body comprises: a cell unit which contains a drug; and an aligner housing unit which is adjacent to the bottom of the cell unit and which rotatably accommodates a main body of the aligner, at least one gutter into which a drug enter via the cell unit is provided at the periphery of the aligner, the gutter extends in a direction having a vertical component, and the depth and width of the gutter are determined such that the longest dimension of a drug is aligned with the direction of extension of the gutter, a partition plate projects from the interior wall of the aligner housing unit so as to partition the gutter into a preparatory aligning unit in the top half and an aligning unit in the bottom half, a drug outlet is provided in the aligner housing unit at a position below the partition plate so as to allow a drug in the aligning unit to fall, designating the longest dimension of a drug as its total length L, and given a drug Px having a total length Lx, which is equal to a maximum total length L of drugs of a variety of dimensions, the gutter of the aligning unit is of a length Ax, which is practically equal to the total length Lx, and the gutter of the preparatory aligning unit is of a length Bx, which is smaller than the total length Lx, and given a drug P other than the drug Px, the gutter of the aligning unit is of a length which is practically equal to the total length L of the drug P, and the gutter of the preparatory aligning unit is equal to or smaller than (Ax+Bx−L).

(15) The assembly of drug feeders as described in (14) above, in which the aligner is generally of a cylindrical form, and a space inside the aligner housing unit is of a cylindrical form having an inner diameter sufficiently large to rotatably accommodate the aligner.

(16) The assembly of drug feeders as described in (15) above, in which the container main body of the same form is used for drugs with different dimensions, and the height H of the cylinder of the aligner housing unit is less than twice the total length Lx of the drug Px.

(17) The assembly of drug feeders as described in (14) above, in which the drug Px is as described below in (A) or (B).

(A) A drug of a form with different dimensions in all three mutually perpendicular directions (x, y, z), in which, designating the largest dimension as a total length L and the remaining two dimensions as a total width W and a total thickness T, the total length L is at least twice the larger of the total width W and total thickness T.

(B) A drug of a form in which one of the dimensions in the three mutually perpendicular directions (x, y, z) is longer than the other two dimensions and the remaining two dimensions are equal to each other, and in which, designating the longest dimension as a total length L and the remaining two dimensions as a total width W and a total thickness T, the total length L is at least twice the total width W.

(18) The assembly of drug feeders as described in (14) above, in which the partition plate is formed as a component separate from the container main body and inserted into the cylindrical space from outside the container main body so as to be detachably secured in the container main body.

(19) A drug feeder comprising: a drug cassette which ejectably accommodates drugs; a base unit which detachably supports the drug cassette and drives a motor to eject the drugs, wherein a reading device which reads identification information assigned to the drug cassette is provided in the base unit, a set of a microprocessor and a memory, or a microprocessor with a built-in memory is mounted in the base unit, wherein a checking means which compares check data stored in the memory with a result of reading by the reading device is built in the microprocessor, and wherein a check bypassing means which temporarily suspends checking function is built in the microprocessor.

(20) The drug feeder of (19) further characterized in that the check bypassing means includes a means for saving the check data and a means for restoring the check data or includes a means for updating a flag for switching between different operations of the check bypassing means.

(21) An automatic dispenser comprising: a drug cassette which ejectably accommodates drugs; a base unit which detachably supports the drug cassette and drives a motor to eject drugs; a drug feeder storage which accommodates a large number of base units; a reading device which is provided in each of the base units and reads identification information assigned to the drug cassette; and a checking means which compares a result of reading with pre-stored check data, wherein a set of a microprocessor and a memory, or a microprocessor with a built-in memory is mounted in each of the base units, the checking means and the check data are built in each microprocessor in a distributed manner, and wherein a check bypassing means which temporarily suspends the checking function of the checking means is built in all or some of the microprocessors.

(22) The automatic drug dispenser of (21) further characterized in that an overwriting means which overwrites the check data with the identification information read by the reading device is built in all or some of the microprocessors.

(23) The automatic drug dispenser of (22) further characterized in that the base units are classified in a first group comprising a relatively large number of base units and a second group comprising a relatively smaller number of base units, wherein the microprocessor mounted in the base unit of the first group activates the check bypassing means instead of activating the overwriting means, and the microprocessor mounted in the base unit of the second group activates the overwriting means instead of activating the check bypassing means.

(24) The automatic drug dispenser of (21) through (23) further characterized in that the check bypassing means may include a means for saving the check data and a means for restoring the check data, or include a means for updating a flag for switching between different operations of the check bypassing means.

(25) An automatic dispenser comprising: a drug cassette which ejectably accommodates drugs; a base unit which detachably supports the drug cassette and drives a motor to eject drugs; a drug feeder storage which accommodates a large number of base units; a reading device which is provided in each of the base units and reads identification information assigned to the drug cassette; a checking means which compares a result of reading with pre-stored check data; and a drug dispensing controller which prepares a drug ejection instruction by referring to prescription data or drug dispensing data derived therefrom and which uses the instruction for motor-driven ejection by the base unit, wherein the drug dispensing controller preparing the drug ejection instruction classifies the base units into a first group comprising a relatively large number of base units and a second group comprising a relatively smaller number of base units, and includes, in the drug ejection instruction addressed to the first group, a drug feeder storage address related to the drug feeder storage, and includes, in the drug ejection instruction addressed to the second group, the check data.

(26) The automatic drug dispenser of (25) further characterized in that a set of a microprocessor and a memory, or a microprocessor with a built-in memory is mounted in each of the base units, and the checking means and the check data are built in each microprocessor in a distributed manner, wherein the microprocessor mounted in the base unit of the second group is provided with and activates a built-in overwriting means which overwrites the check data with the identification information read by the reading device, and the microprocessor mounted in the base unit of the first group is not provided with an overwriting means or does not activate the overwriting means.

(27) The automatic drug dispenser of (25) or (26) further characterized in that each base unit is provided with a lighted indicator, wherein, when lighting a desired indicator, several neighboring indicators are also lighted.

(28) A tablet counting and monitoring apparatus for capturing images of a series of packs comprising perforated compartments in packing paper and automatically counting tablets in the packs, comprising: a tilt detecting means which detects the tilt of the perforation or an equivalent thereof, in accordance with captured image data; and a transporting mechanism which varies the direction of transportation of the packing paper such that the tilt is eliminated, in accordance with the tilt thus detected.

(29) The tablet counting and monitoring apparatus of (28) further characterized in that a disentangling mechanism for applying mechanical action on the pack and disentangling the drugs inside is provided upstream of an imaging position, and the transporting mechanism is capable of transporting the packing paper in a reverse direction as well as in a forward direction.

While the preferred embodiments of the present invention have been described using specific terms, such description is for illustrative purposes only, and it is to be understood that changes and variations may be made without departing from the spirit or scope of the appended claims.

What is claimed is:

1. An automatic drug dispenser comprising:
a drug cassette which ejectably accommodates drugs;
a base unit which detachably supports the drug cassette and drives a motor to eject drugs;
a drug feeder storage which stores a plurality of base units;
a reading device which is provided in each of the base units and reads identification information assigned to the drug cassette;
a checking means which compares a result of reading with pre-stored check data;
an overwriting means which overwrites the check data with the identification information read by the reading device; and
a microprocessor with a built-in memory mounted in each of the base units, the checking means is built in each microprocessor in a distributed manner, the check data is built in the built-in memory in a distributed manner, and a determination as to whether the drug cassette is properly attached is made exclusively by the base unit.

2. The automatic drug dispenser according to claim 1, wherein, if the result of comparison indicates matching failure, the base unit suspends motor-driven ejection and causes associated information to be output.

3. The automatic drug dispenser according to claim 1, wherein the base unit is provided with a plurality of indicators, the microprocessor is provided with a communication means, and at least one of the indicators displays a drug ejection enabled state and at least one other of the indicators displays a communication enabled state indicating that communication is enabled in the microprocessor.

4. The automatic drug dispenser according to claim 2, wherein the base unit is provided with a plurality of indicators, the microprocessor is provided with a communication means, and at least one of the indicators displays a drug ejection enabled state and at least one other of the indicators displays a communication enabled state indicating that communication is enabled in the microprocessor.

5. A drug feeder comprising:
a drug cassette which ejectably accommodates drugs; and
a base unit which detachably supports the drug cassette and drives a motor to eject the drugs, wherein the base unit comprises:
a reading device which reads identification information assigned to the drug cassette;
a set of a microprocessor and a memory, or a microprocessor with a built-in memory; and
a manually-operated switch, wherein
a checking means which compares check data stored in the memory with a result of reading by the reading device is built in the microprocessor, and wherein
a check bypassing means which temporarily suspends checking function in accordance with the manipulation of the manually-operated switch is built in the microprocessor, and
the checking means is built in each microprocessor of the base unit in a distributed manner, the check data is built in the built-in memory in a distributed manner, and a determination as to whether the drug cassette is properly attached is made exclusively by the base unit.

6. The drug feeder according to claim 5, wherein the check bypassing means includes a means for saving the check data and a means for restoring the check data or includes a means for updating a flag for switching between different operations of the check bypassing means.

7. An automatic dispenser comprising:
a drug cassette which ejectably accommodates drugs;
a base unit which detachably supports the drug cassette and drives a motor to eject drugs;
a drug feeder storage which accommodates a plurality of base units;
a reading device which is provided in each of the base units and reads identification information assigned to the drug cassette; and
a checking means which compares a result of reading with pre-stored check data, wherein
a set of a microprocessor and a memory, or a microprocessor with a built-in memory is mounted in and a manually-operated switch is provided in each of the base units, and wherein,
in addition to the checking means which compares check data stored in the memory with a result of reading by the reading device, a check bypassing means which temporarily suspends checking function in accordance with the manipulation of the manually-operated switch is built in the microprocessor, and
the checking means is built in each microprocessor of the base unit in a distributed manner, the check data is built in the built-in memory in a distributed manner, and a determination as to whether the drug cassette is properly attached is made exclusively by the base unit.

8. The automatic drug dispenser according to claim 7, wherein an overwriting means which overwrites the check data with the identification information read by the reading device is built in the microprocessor.

9. The automatic drug dispenser according to claim 8, wherein the microprocessor mounted in the base unit of a first group activates the check bypassing means instead of activating the overwriting means, and the microprocessor mounted in the base unit of a second group activates the overwriting means instead of activating the check bypassing means.

10. The automatic drug dispenser according to claim 7, wherein the check bypassing means includes a means for saving the check data and a means for restoring the check data or includes a means for updating a flag for switching between different operations of the check bypassing means.

11. The automatic drug dispenser according to claim 8, wherein the check bypassing means includes a means for saving the check data and a means for restoring the check data or includes a means for updating a flag for switching between different operations of the check bypassing means.

12. The automatic drug dispenser according to claim 9, wherein the check bypassing means includes a means for saving the check data and a means for restoring the check data or includes a means for updating a flag for switching between different operations of the check bypassing means.

13. An automatic dispenser comprising:
a drug cassette which ejectably accommodates drugs;
a base unit which detachably supports the drug cassette and drives a motor to eject drugs;
a drug feeder storage which accommodates a plurality of base units;
a reading device which is provided in each of the base units and reads identification information assigned to the drug cassette;
a checking means which compares a result of reading with pre-stored check data; and
a drug dispensing controller which prepares a drug ejection instruction by referring to prescription data or drug dispensing data derived therefrom and which uses the instruction for motor-driven ejection by the base unit, wherein
a set of a microprocessor and a memory, or a microprocessor with a built-in memory is mounted in each of the base units, the checking means is built in each microprocessor in a distributed manner, the check data is built in the built-in memory in a distributed manner, and a determination as to whether the drug cassette is properly attached is made exclusively by the base unit,
the base units are classified in a first group comprising a plurality of base units and a second group comprising a relatively smaller number of base units, and wherein
the drug dispensing controller preparing the drug ejection instruction includes, in the drug ejection instruction addressed to the first group, a drug feeder storage address related to the drug feeder storage, and includes, in the drug ejection instruction addressed to the second group, the check data.

14. The automatic drug dispenser according to claim 13, wherein a set of a microprocessor and a memory, or a microprocessor with a built-in memory is mounted in each of the base units, and the checking means and the check data are built in each microprocessor in a distributed manner, and wherein the microprocessor mounted in the base unit of the second group is provided with and activates an operably built-in overwriting means which overwrites the check data with the identification information read by the reading device, and the microprocessor mounted in the base unit of the first group is not provided with an overwriting means or does not activate the overwriting means.

* * * * *